US008735552B2

(12) United States Patent
Kumar et al.

(10) Patent No.: US 8,735,552 B2
(45) Date of Patent: May 27, 2014

(54) GENERATION, EXPRESSION AND CHARACTERIZATION OF THE HUMANIZED K33N MONOCLONAL ANTIBODY

(75) Inventors: Shankar Kumar, Pleasanton, CA (US); J. Yun Tso, Menlo Park, CA (US); Naoya Tsurushita, Palo Alto, CA (US); Tatsuhiro Harada, Kyoto (JP)

(73) Assignees: Gene Techno Science Co., Ltd., Hokkaido (JP); Kaken Pharmaceutical Co., Tokyo (JP)

( * ) Notice: Subject to any disclaimer, the term of this patent is extended or adjusted under 35 U.S.C. 154(b) by 155 days.

(21) Appl. No.: 13/201,847

(22) PCT Filed: Mar. 10, 2010

(86) PCT No.: PCT/JP2010/054483
§ 371 (c)(1),
(2), (4) Date: Aug. 16, 2011

(87) PCT Pub. No.: WO2010/104208
PCT Pub. Date: Sep. 16, 2010

(65) Prior Publication Data
US 2011/0300139 A1    Dec. 8, 2011

Related U.S. Application Data

(60) Provisional application No. 61/158,885, filed on Mar. 10, 2009, provisional application No. 61/251,072, filed on Oct. 13, 2009.

(51) Int. Cl.
*C07K 16/28* (2006.01)

(52) U.S. Cl.
USPC ............... 530/388.22; 530/350; 530/387.1; 530/387.3; 530/387.7; 530/388.8

(58) Field of Classification Search
USPC ........... 530/350, 387.1, 387.3, 387.7, 388.22, 530/388.8
See application file for complete search history.

(56) References Cited

U.S. PATENT DOCUMENTS

| | | | |
|---|---|---|---|
| 7,572,640 B2 * | 8/2009 | Goix et al. ................ | 436/172 |
| 8,372,639 B2 * | 2/2013 | Kon et al. ................ | 435/326 |
| 2004/0234524 A1 | 11/2004 | Uede et al. | |
| 2008/0152653 A1 | 6/2008 | Kurotaki et al. | |
| 2009/0252734 A1 | 10/2009 | Kanayama et al. | |
| 2011/0318368 A1 * | 12/2011 | Kon et al. ................ | 424/172.1 |
| 2013/0122019 A1 * | 5/2013 | Kon et al. ................ | 424/172.1 |

FOREIGN PATENT DOCUMENTS

| EP | 2 399 937 | | 12/2011 |
|---|---|---|---|
| JP | 2009-167115 | | 7/2009 |
| JP | 2009167115 A | * | 7/2009 |
| WO | WO-02/081522 | | 10/2002 |
| WO | WO-2006/075784 | | 7/2006 |
| WO | WO-2008/007804 | | 1/2008 |
| WO | WO-2009/088064 | | 7/2009 |
| WO | WO-2009/088065 | | 7/2009 |
| WO | WO-2009/088105 | | 7/2009 |

OTHER PUBLICATIONS

Rao et al. (J. Bone Miner Res. Oct. 2006; 21 (10): 1657-65).*
Rudikoff et al (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Winkler et al. (J. Immunol. Oct. 15, 2000; 165 (8): 4505-4514).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Genbank Public DNA Database, Accession No. X07979, updated Dec. 26, 2011.
Office Action for Chinese Application No. 201080009550.X, issued Apr. 24, 2013, 13 pages (including English translation).
Almagro et al., "Humanization of Antibodies," Frontiers in Bioscience (2008) 13:1619-1633.
Queen et al., "A Humanized Antibody that Binds to the Interleukin 2 Receptor," Proceedings of the National Acadamy of Sciences (1989) 86(24):10029-10033.
Weiner, "Fully Human Therapeutic Monoclonal Antibodies," Journal of Immunotherapy (2006) 29(1):1-9.
Miyasaka (ed.), New Edition of Adhesion Molecule Handbook, Shujunsya (2000) (translation).
Barry et al., "Analysis of the α4β1 Integrin-Osteopontin Interaction", Experimental Cell Res. (2000) 258:342-351.
GenBank Pubulic DNA Database, Accession No. NM_002207, Jul. 31, 2011.
GenBank Pubulic DNA Database, Accession No. NM_133721 Jul. 16, 2011.
GenBank Pubulic DNA Database, Accession No. NM_000885 Jul. 29, 2011.

(Continued)

*Primary Examiner* — Stephen Rawlings
(74) *Attorney, Agent, or Firm* — Morrison & Foerster LLP

(57) ABSTRACT

The present invention provides humanized antibodies that immunospecifically recognize human 9 integrin. Some of these antibodies inhibit the biological functions of the 9 integrin, thereby exhibiting therapeutic effects on various disorders or diseases that are associated with 9 integrin, including cancer, e.g., the growth and metastasis of a cancer cell, and inflammatory diseases, e.g., rheumatoid arthritis, osteoarthritis, hepatitis, bronchial asthma, fibrosis, diabetes, arteriosclerosis, multiple sclerosis, granuloma, an inflammatory bowel disease (ulcerative colitis and Crohn's disease), an autoimmune disease, and so forth.

2 Claims, 23 Drawing Sheets

(56) References Cited

OTHER PUBLICATIONS

GenBank Pubulic DNA Database, Accession No. NM_010576 Jul. 23, 2011.

GenBank Pubulic DNA Database, Accession No. NM_010578 Jul. 31, 2011.

Green et al., "Structual elements of the osteopontin SVVYGLR motif important for the interaction with $\alpha_4$ integrins," FEBS Letters (2001) 503:75-79.

Hynes, "Integrins: Bidirectional, Allosteric Signaling Machines," Cell (2002) 110:673-687.

Palmer et al., "Sequence and Tissue Distribution of the Integrin $\alpha 9$ Subunit, a Novel Partner of $\beta 1$ That is Widely Distributed in Epithelia and Muscle," J. Cell Biol. (1993) 123:1289-1297.

Wang et al., "Differential regulation of airway epithelial integrins by growth factors," Am. J. Respir. Cell Mol. Biol. (1996) 15:664-672.

Yokosaki et al., "The Integrin $\alpha_9\beta_1$ Binds to a Novel Recognition Sequence (SVVYGLR) in the Thrombin-cleaved Amino-terminal Fragment of Osteopontin", J. Biol. Chem. (1999) 274:36328-36334.

Second Office Action, issued Dec. 4, 2013, in CN 201080009550.X, 11 pages (translation included).

\* cited by examiner

Figure 3

```
ATGGGATGGAGCTGGATCTTTCTCTTCCTCCTGTCAGGAACTGCAGGTGTCCATTGCCAG
 M   G   W   S   W   I   F   L   F   L   L   S   G   T   A   G   V   H   C   Q

GTCCAACTGCAGCAGTCTGGACCTGAGCTGGTGAAGCCTGGGGCTTCAGTGAAGATATCC
 V   Q   L   Q   Q   S   G   P   E   L   V   K   P   G   A   S   V   K   I   S

TGCAAGGCTTCTGGCTACAGCTTTACAAGTTACTATATGAATTGGGTGAAGAAGAGGCCT
 C   K   A   S   G   Y   S   F   T   S   Y   Y   M   N   W   V   K   K   R   P

GGACAGGGACTTGAGTGGATTGGTTGGATCTTTCCTGGAAGTGGTAATACTAAGTACAAT
 G   Q   G   L   E   W   I   G   W   I   F   P   G   S   G   N   T   K   Y   N

GAGAAGTTCAAGGGCAAGGCCACACTGACGGCAGACACATCCTCCAGTACAGCCTACATG
 E   K   F   K   G   K   A   T   L   T   A   D   T   S   S   S   T   A   Y   M

CAGGTCAGCAGCCTGACATCTGAGGACTCTGCAGTCTATTTCTGTGCAAGATCGTGGGTT
 Q   V   S   S   L   T   S   E   D   S   A   V   Y   F   C   A   R   S   W   V

AGCTACGAGAGGGGGTATTATTTTGACTACTGGGGTCAAGGCACCAGTCTCACAGTCTCC
 S   Y   E   R   G   Y   Y   F   D   Y   W   G   Q   G   T   S   L   T   V   S

TCA
 S
```

Figure 4

ATGAGTGTGCCCACTCAACTCCTGGGGTTGCTGCTGCTGTGGCTTACAGACGCAGGATGT
 M   S   V   P   T   Q   L   L   G   L   L   L   W   L   T   D   A   G   C

GACATCCAGATGACTCAGTCTCCAGCCTCCCTGGCTGCATCTGTGGGAGAAACTGTCACC
 <u>D</u>   I   Q   M   T   Q   S   P   A   S   L   A   A   S   V   G   E   T   V   T

CTCACATGTCGAGCAAGTGAGAACATTTACTACAGTTTAGCATGGTATCAGCAGAAGCAA
 L   T   C   <u>R   A   S   E   N   I   Y   Y   S   L   A</u>   W   Y   Q   Q   K   Q

GGGAAATCTCCTCAGCTCCTGATCTATAATGCAAACAGCTTGGAAGATGGTGTCCCATCG
 G   K   S   P   Q   L   L   I   Y   <u>N   A   N   S   L   E   D</u>   G   V   P   S

AGGTTCAGTGGCAGTGGATCTGGGACACAGTATTCTATGAAGATCAACAGCATGCAGCCT
 R   F   S   G   S   G   S   G   T   Q   Y   S   M   K   I   N   S   M   Q   P

GAAGATACCGCAACTTATTTCTGTAAACAGGCTTATGACGTTCCGTACACGTTCGGAGGG
 E   D   T   A   T   Y   F   C   <u>K   Q   A   Y   D   V   P   Y   T</u>   F   G   G

GGGACCAAGCTGGAAATAAAA
 G   T   K   L   E   I   K

Figure 5

```
SpeI
ACTAGTACCACCATGGGATGGAGCTGGATCTTTCTCTTCCTCCTGTCAGGAACTGCAGGT
         M  G  W  S  W  I  F  L  F  L  L  S  G  T  A  G

GTCCATTGCCAGGTCCAACTGCAGCAGTCTGGACCTGAGCTGGTGAAGCCTGGGGCTTCA
 V  H  C  Q  V  Q  L  Q  Q  S  G  P  E  L  V  K  P  G  A  S

GTGAAGATATCCTGCAAGGCTTCTGGCTACAGCTTTACAAGTTACTATATGAATTGGGTG
 V  K  I  S  C  K  A  S  G  Y  S  F  T  S  Y  Y  M  N  W  V

AAGAAGAGGCCTGGACAGGGACTTGAGTGGATTGGTTGGATCTTTCCTGGAAGTGGTAAT
 K  K  R  P  G  Q  G  L  E  W  I  G  W  I  F  P  G  S  G  N

ACTAAGTACAATGAGAAGTTCAAGGGCAAGGCCACACTGACGGCAGACACATCCTCCAGT
 T  K  Y  N  E  K  F  K  G  K  A  T  L  T  A  D  T  S  S  S

ACAGCCTACATGCAGGTCAGCAGCCTGACATCTGAGGACTCTGCAGTCTATTTCTGTGCA
 T  A  Y  M  Q  V  S  S  L  T  S  E  D  S  A  V  Y  F  C  A

AGATCGTGGGTTAGCTACgAGAGGGGGTATTATTTTGACTACTGGGGTCaAGGCACCAGT
 R  S  W  V  S  Y  E  R  G  Y  Y  F  D  Y  W  G  Q  G  T  S

HindIII
CTCACAGTCTCCTCAGGTGAGTCCTTAAAACAAGCTT
 L  T  V  S  S
```

Figure 6

```
NheI
GCTAGCACCACCATGAGTGTGCCCACTCAACTCCTGGGGTTGCTGCTGCTGTGGCTTACA
         M  S  V  P  T  Q  L  L  G  L  L  L  L  W  L  T

GACGCAGGATGTGACATCCAGATGACTCAGTCTCCAGCCTCCCTGGCTGCATCTGTGGGA
 D  A  G  C  D  I  Q  M  T  Q  S  P  A  S  L  A  A  S  V  G

GAAACTGTCACCCTCACATGTCGAGCAAGTGAGAACATTTACTACAGTTTAGCATGGTAT
 E  T  V  T  L  T  C  R  A  S  E  N  I  Y  Y  S  L  A  W  Y

CAGCAGAAGCAAGGGAAATCTCCTCAGCTCCTGATCTATAATGCAAACAGCTTGGAAGAT
 Q  Q  K  Q  G  K  S  P  Q  L  L  I  Y  N  A  N  S  L  E  D

GGTGTCCCATCGAGGTTCAGTGGCAGTGGATCTGGGACACAGTATTCTATGAAGATCAAC
 G  V  P  S  R  F  S  G  S  G  S  G  T  Q  Y  S  M  K  I  N

AGCATGCAGCCTGAAGATACCGCAACTTATTTCTGTAAACAGGCTTATGACGTTCCGTAC
 S  M  Q  P  E  D  T  A  T  Y  F  C  K  Q  A  Y  D  V  P  Y

EcoRI
ACGTTCGGAGGGGGGACCAAGCTGGAAATAAAACGTAAGTAGTCTTCTCAGAATTC
 T  F  G  G  G  T  K  L  E  I  K
```

Figure 8

```
                      1          2          3          4
          123456789 0123456789 0123456789 0123456789 0123456789
K33N      QVQLQQSGP ELVKPGASVK ISCKASGYSF TSYYMNWVKK RPGQGLEWIG
HuK33N    QVQLVQSGA EVKKPGASVK VSCKASGYSF TSYYMNWVRQ APGQRLEWIG
DA980102  QVQLVQSGA EVKKPGASVK VSCKASGYTF T-----WVRQ APGQRLEWMG 5          6          7          8
          01223456789 0123456789 0123456789 0122223456789
            a                               abc
K33N      WIFPGSGNTKY NEKFKGKATL TADTSSSTAY MQVSSLTSEDSAV
HuK33N    WIFPGSGNTKY NEKFKGKATL TADTSASTAY MELSSLRSEDTAV
DA980102  ----------- ------RVTL TSDTSASTAY MEMSSLRSEDTAV 1          1
            9           0          1
          0123456789 000000123456789 0123
                     abcde
K33N      YFCARSWVSY ERGYYFDYWGQGTSL  TVSS
HuK33N    YYCARSWVSY ERGYYFDYWGQGTLV  TVSS
DA980102  YYCAR----- -------WGQGTLV   TVSS
```

Figure 9

```
                  1          2          3
         123456789 0123456789 0123456789 0123456789
K33N VL  DIQMTQSPA SLAASVGETV TLTCRASENI YYSLAWYQQK
HuK33N VL DIQMTQSPS SLSASVGDRV TITCRASENI YYSLAWYQQK
X72441   DIQMTQSPS SLSASVGDRV TITC------ -----WYQQK 4          5          6          7
         0123456789 0123456789 0123456789 0123456789
K33N VL  QGKSPQLLIY NANSLEDGVP SRFSGSGSGT QYSMKINSMQ
HuK33N VL PGKAPKLLIY NANSLEDGVP SRFSGSGSGT QYTLTISSLQ
X72441   PGKAPKLLIY -------GVP SRFSGSGSGT DFTLTISSLQ 1
         8          9          0
         0123456789 0123456789 01234567
K33N VL  PEDTATYFCK QAYDVPYTFG GGTKLEIK
HuK33N VL PEDFATYYCK QAYDVPYTFG QGTKVEIK
X72441   PEDFATYYC- --------FG QGTKVEIK
```

Figure 10

```
JNJ120   GGGACTAGTACCACCATGAAATGCAGC
JNJ137   GGGACTAGTACCACCATGAAATGCAGCTGGGTTATCTTCTTCCTGATGGCAGTGGTT
JNJ145   TCCGCGAGCACAGCCTACATGGAGCTCAGCAGCCTGAGATCTGAGGACACTGCCGTC
JNJ148   GGGAAGCTTTTGTGAGGACTCACCTGAGGAGACGGTGACCAGGGTTCCTTGACC
JNJ149   GGGAAGCTTTTGTGAGGACTC
JNJ151   AGACTGCACCAGTTGGACCTGTGAATTGACCCCTGTAACCACTGCCATCAGGAAGAA
JNJ152   CAGGTCCAACTGGTGCAGTCTGGAGCTGAGGTTAAGAAGCCTGGGGCTTCAGTGAAG
JNJ153   ACTTGTAAAGCTGTAGCCAGAAGCCTTGCAGGAAACCTTCACTGAAGCCCCAGGCTT
JNJ154   TCTGGCTACAGCTTTACAAGTTACTATATGAATTGGGTGCGCCAGGCCCCTGGACAGAGG
JNJ155   ACCACTTCCAGGAAAGATCCAACCAATCCACTCAAGCCTCTGTCCAGGGGCCTGGCG
JNJ156   TGGATCTTTCCTGGAAGTGGTAATACTAAGTACAATGAGAAGTTCAAGGGCAAGGCCACA
JNJ157   CATGTAGGCTGTACTGGCGGATGTGTCTGCCGTCAGTGTGGCCTTGCCCTTGAACTT
JNJ158   CCTCTCGTAGCTAACCCACGATCTTGCACAGTAATAGACTGCAGTGTCCTCAGATCT
JNJ159   TCGTGGGTTAGCTACGAGAGGGGGTATTATTTTGACTACTGGGGTCAAGGAACCCTGGTC
```

Figure 11

```
JNJ150    GGGGCTAGCACCACCATGAGT
JNJ126    GGGGCTAGCACCACCATGAGTGTGCCCACTCAACTCCTGGGGTTGCTGCTGCTGTGG
JNJ127    AGACTGAGTCATCTGGATGTCACATCGTGCGTCTGTAAGCCACAGCAGCAGCAACCCCAG
JNJ128    GACATCCAGATGACTCAGTCTCCATCCTCCCTGTCTGCATCTGTGGGAGACAGA
JNJ129    GTAAATGTTCTCACTTGCTCGACATGTGATGGTGACTCTGTCTCCCACAGATGCAGA
JNJ130    CGAGCAAGTGAGAACATTTACTACAGTTTAGCATGGTATCAGCAGAAGCCAGGGAAA
JNJ131    CAAGCTGTTTGCATTATAGATCAGGAGCTTAGGGGCTTTCCCTGGCTTCTGCTGATA
JNJ132    ATCTATAATGCAAACAGCTTGGAAGATGGTGTCCCATCGAGGTTCAGTGGCAGTGGA
JNJ133    CAGGCTGCTGATGGTGAGAGTATACTGTGTCCCAGATCCACTGCCACTGAACCTCGA
JNJ134    ACTCTCACCATCAGCAGCCTGCAGCCTGAAGATTTTGCAACTTATTACTGTAAACAG
JNJ135    GGTCCCTTGTCCGAACGTGTACGGAACGTCATAAGCCTGTTTACAGTAATAAGTTGC
JNJ136    TACACGTTCGGACAAGGGACCAAGGTGGAAATCAAACGTGAGTAG
JNJ101    GGGGAATTCTTTAAATTCTACTCACGTTTGATTTCCA
JNJ117    GGGGAATTCTTTAAATTCTA
```

Figure 12

```
    SpeI
GGGACTAGTACCACC ATG AAA TGC AGC TGG GTT ATC TTC TTC CTG ATG GCA GTG GTT ACA GGG
                 M   K   C   S   W   V   I   F   F   L   M   A   V   V   T   G
                                    JNJ137
           JNJ120

GTC AAT TCA CAG GTC CAA CTG GTG CAG TCT GGA GCT GAG GTT AAG AAG CCT GGG GCT TCA
 V   N   S   Q   V   Q   L   V   Q   S   G   A   E   V   K   K   P   G   A   S
                                                    JNJ152
  JNJ151

GTG AAG GTT TCC TGC AAG GCT TCT GGC TAC AGC TTT ACA AGT TAC TAT ATG AAT TGG GTG
 V   K   V   S   C   K   A   S   G   Y   S   F   T   S   Y   Y   M   N   W   V
                                                                 JNJ154
            JNJ153

CGC CAG GCC CCT GGA CAG AGG CTT GAG TGG ATT GGT TGG ATC TTT CCT GGA AGT GGT AAT
 R   Q   A   P   G   Q   R   L   E   W   I   G   W   I   F   P   G   S   G   N
                            JNJ155

ACT AAG TAC AAT GAG AAG TTC AAG GGC AAG GCC ACA CTG ACG GCA GAC ACA TCC GCC AGT
 T   K   Y   N   E   K   F   K   G   K   A   T   L   T   A   D   T   S   A   S
   JNJ156
                                                    JNJ157

ACA GCC TAC ATG GAG CTC AGC AGC CTG AGA TCT GAG GAC ACT GCC GTC TAT TAC TGT GCA
 T   A   Y   M   E   L   S   S   L   R   S   E   D   T   A   V   Y   Y   C   A
                JNJ145
                                                                    JNJ158

AGA TCG TGG GTT AGC TAC GAG AGG GGG TAT TAT TTT GAC TAC TGG GGT CAA GGA ACC CTG
 R   S   W   V   S   Y   E   R   G   Y   Y   F   D   Y   W   G   Q   G   T   L
                                    JNJ159

HindIII
GTC ACC GTC TCC TCA GGTGAGTCCTCACAAAAGCTTCCC
 V   T   V   S   S                  JNJ149
            JNJ148
```

Figure 13

```
     NheI
GGGGCTAGCACCACC ATG AGT GTG CCC ACT CAA CTC CTG GGG TTG CTG CTG CTG TGG CTT ACA
              ▶ M   S   V   P   T   Q   L   L   G   L   L   L   L   W   L   T
                           JNJ126
        JNJ150

GAC GCA CGA TGT GAC ATC CAG ATG ACT CAG TCT CCA TCC TCC CTG TCT GCA TCT GTG GGA
▶  D   A   R   C   D   I   Q   M   T   Q   S   P   S   S   L   S   A   S   V   G
                                                       JNJ128
           JNJ127

GAC AGA GTC ACC ATC ACA TGT CGA GCA AGT GAG AAC ATT TAC TAC AGT TTA GCA TGG TAT
▶  D   R   V   T   I   T   C   R   A   S   E   N   I   Y   Y   S   L   A   W   Y
                                                                   JNJ130
                  JNJ129

CAG CAG AAG CCA GGG AAA GCC CCT AAG CTC CTG ATC TAT AAT GCA AAC AGC TTG GAA GAT
▶  Q   Q   K   P   G   K   A   P   K   L   L   I   Y   N   A   N   S   L   E   D

JNJ131

GGT GTC CCA TCG AGG TTC AGT GGC AGT GGA TCT GGG ACA CAG TAT ACT CTC ACC ATC AGC
▶  G   V   P   S   R   F   S   G   S   G   S   G   T   Q   Y   T   L   T   I   S
    JNJ132                              JNJ133

PstI
  AGC CTG CAG CCT GAA GAT TTT GCA ACT TAT TAC TGT AAA CAG GCT TAT GAC GTT CCG TAC
▶  S   L   Q   P   E   D   F   A   T   Y   Y   C   K   Q   A   Y   D   V   P   Y
            JNJ134                           JNJ135

EcoRI
  ACG TTC GGA CAA GGG ACC AAG GTG GAA ATC AAA CGTGAGTAGAATTTAAAGAATTCCCC
▶  T   F   G   Q   G   T   K   V   E   I   K                    JNJ117
                       JNJ136
                                             JNJ101
```

Figure 14

```
SpeI
ACTAGTACCACCATGAAATGCAGCTGGGTTATCTTCTTCCTGATGGCAGTGGTTACAGGG
            M   K   C   S   W   V   I   F   F   L   M   A   V   V   T   G

GTCAATTCACAGGTCCAACTGGTGCAGTCTGGAGCTGAGGTTAAGAAGCCTGGGGCTTCA
 V   N   S   Q   V   Q   L   V   Q   S   G   A   E   V   K   K   P   G   A   S

GTGAAGGTTTCCTGCAAGGCTTCTGGCTACAGCTTTACAAGTTACTATATGAATTGGGTG
 V   K   V   S   C   K   A   S   G   Y   S   F   T   S   Y   Y   M   N   W   V

CGCCAGGCCCCTGGACAGAGGCTTGAGTGGATTGGTTGGATCTTTCCTGGAAGTGGTAAT
 R   Q   A   P   G   Q   R   L   E   W   I   G   W   I   F   P   G   S   G   N

ACTAAGTACAATGAGAAGTTCAAGGGCAAGGCCACACTGACGGCAGACACATCCGCCAGT
 T   K   Y   N   E   K   F   K   G   K   A   T   L   T   A   D   T   S   A   S

ACAGCCTACATGGAGCTCAGCAGCCTGAGATCTGAGGACACTGCCGTCTATTACTGTGCA
 T   A   Y   M   E   L   S   S   L   R   S   E   D   T   A   V   Y   Y   C   A

AGATCGTGGGTTAGCTACGAGAGGGGGTATTATTTTGACTACTGGGGTCAAGGAACCCTG
 R   S   W   V   S   Y   E   R   G   Y   Y   F   D   Y   W   G   Q   G   T   L

HindIII
GTCACCGTCTCCTCAGGTGAGTCCTCACAAAAGCTT
 V   T   V   S   S
```

Figure 15

```
NheI
GCTAGCACCACCATGAGTGTGCCCACTCAACTCCTGGGGTTGCTGCTGCTGTGGCTTACA
          M  S  V  P  T  Q  L  L  G  L  L  L  L  W  L  T

GACGCACGATGTGACATCCAGATGACTCAGTCTCCATCCTCCCTGTCTGCATCTGTGGGA
 D  A  R  C  D  I  Q  M  T  Q  S  P  S  S  L  S  A  S  V  G

GACAGAGTCACCATCACATGTCGAGCAAGTGAGAACATTTACTACAGTTTAGCATGGTAT
 D  R  V  T  I  T  C  R  A  S  E  N  I  Y  Y  S  L  A  W  Y

CAGCAGAAGCCAGGGAAAGCCCCTAAGCTCCTGATCTATAATGCAAACAGCTTGGAAGAT
 Q  Q  K  P  G  K  A  P  K  L  L  I  Y  N  A  N  S  L  E  D

GGTGTCCCATCGAGGTTCAGTGGCAGTGGATCTGGGACACAGTATACTCTCACCATCAGC
 G  V  P  S  R  F  S  G  S  G  S  G  T  Q  Y  T  L  T  I  S

AGCCTGCAGCCTGAAGATTTTGCAACTTATTACTGTAAACAGGCTTATGACGTTCCGTAC
 S  L  Q  P  E  D  F  A  T  Y  Y  C  K  Q  A  Y  D  V  P  Y

EcoRI
ACGTTCGGACAAGGGACCAAGGTGGAAATCAAACGTGAGTAGAATTTAAAGAATTC
 T  F  G  Q  G  T  K  V  E  I  K
```

Figure 17

| | |
|---|---|
| CMV2 | GAACCGTCAGATCGCCTGGAGACG |
| JNT026 | TGAAAGATGAGCTGGAGGAC |
| JNT080 | GAACTGTGGCTGCACCATC |
| JNT082 | CTTTCTTGTCCACCTTGGTG |
| JNT084 | GTTGAAGCTCTTTGTGACGG |
| JNT097 | GCTGTCCTACAGTCCTCAG |
| JNT098 | ACGTGCCAAGCATCCTCG |

Figure 18

```
ATGAAATGCAGCTGGGTTATCTTCTTCCTGATGGCAGTGGTTACAGGGGTCAATTCACAG
 M   K   C   S   W   V   I   F   F   L   M   A   V   V   T   G   V   N   S   Q
GTCCAACTGGTGCAGTCTGGAGCTGAGGTTAAGAAGCCTGGGGCTTCAGTGAAGGTTTCC
 V   Q   L   V   Q   S   G   A   E   V   K   K   P   G   A   S   V   K   V   S
TGCAAGGCTTCTGGCTACAGCTTTACAAGTTACTATATGAATTGGGTGCGCCAGGCCCCT
 C   K   A   S   G   Y   S   F   T   S   Y   Y   M   N   W   V   R   Q   A   P
GGACAGAGGCTTGAGTGGATTGGTTGGATCTTTCCTGGAAGTGGTAATACTAAGTACAAT
 G   Q   R   L   E   W   I   G   W   I   F   P   G   S   G   N   T   K   Y   N
GAGAAGTTCAAGGGCAAGGCCACACTGACGGCAGACACATCCGCCAGTACAGCCTACATG
 E   K   F   K   G   K   A   T   L   T   A   D   T   S   A   S   T   A   Y   M
GAGCTCAGCAGCCTGAGATCTGAGGACACTGCCGTCTATTACTGTGCAAGATCGTGGGTT
 E   L   S   S   L   R   S   E   D   T   A   V   Y   Y   C   A   R   S   W   V
AGCTACGAGAGGGGGTATTATTTTGACTACTGGGGTCAAGGAACCCTGGTCACCGTCTCC
 S   Y   E   R   G   Y   Y   F   D   Y   W   G   Q   G   T   L   V   T   V   S
TCAGCCTCCACCAAGGGCCCATCGGTCTTCCCCCTGGCACCCTCCTCCAAGAGCACCTCT
 S   A   S   T   K   G   P   S   V   F   P   L   A   P   S   S   K   S   T   S
GGGGGCACAGCGGCCCTGGGCTGCCTGGTCAAGGACTACTTCCCCGAACCGGTGACGGTG
 G   G   T   A   A   L   G   C   L   V   K   D   Y   F   P   E   P   V   T   V
TCGTGGAACTCAGGCGCCCTGACCAGCGGCGTGCACACCTTCCCGGCTGTCCTACAGTCC
 S   W   N   S   G   A   L   T   S   G   V   H   T   F   P   A   V   L   Q   S
TCAGGACTCTACTCCCTCAGCAGCGTGGTGACCGTGCCCTCCAGCAGCTTGGGCACCCAG
 S   G   L   Y   S   L   S   S   V   V   T   V   P   S   S   S   L   G   T   Q
ACCTACATCTGCAACGTGAATCACAAGCCCAGCAACACCAAGGTGGACAAGAAAGTTGAG
 T   Y   I   C   N   V   N   H   K   P   S   N   T   K   V   D   K   K   V   E
CCCAAATCTTGTGACAAAACTCACACATGCCCACCGTGCCCAGCACCTGAACTCCTGGGG
 P   K   S   C   D   K   T   H   T   C   P   P   C   P   A   P   E   L   L   G
GGACCGTCAGTCTTCCTCTTCCCCCCAAAACCCAAGGACACCCTCATGATCTCCCGGACC
 G   P   S   V   F   L   F   P   P   K   P   K   D   T   L   M   I   S   R   T
CCTGAGGTCACATGCGTGGTGGTGGACGTGAGCCACGAAGACCCTGAGGTCAAGTTCAAC
 P   E   V   T   C   V   V   V   D   V   S   H   E   D   P   E   V   K   F   N
TGGTACGTGGACGGCGTGGAGGTGCATAATGCCAAGACAAAGCCGCGGGAGGAGCAGTAC
 W   Y   V   D   G   V   E   V   H   N   A   K   T   K   P   R   E   E   Q   Y
AACAGCACGTACCGTGTGGTCAGCGTCCTCACCGTCCTGCACCAGGACTGGCTGAATGGC
 N   S   T   Y   R   V   V   S   V   L   T   V   L   H   Q   D   W   L   N   G
AAGGAGTACAAGTGCAAGGTCTCCAACAAAGCCCTCCCAGCCCCCATCGAGAAAACCATC
 K   E   Y   K   C   K   V   S   N   K   A   L   P   A   P   I   E   K   T   I
TCCAAAGCCAAAGGGCAGCCCCGAGAACCACAGGTGTACACCCTGCCCCCATCCCGGGAT
 S   K   A   K   G   Q   P   R   E   P   Q   V   Y   T   L   P   P   S   R   D
GAGCTGACCAAGAACCAGGTCAGCCTGACCTGCCTGGTCAAAGGCTTCTATCCCAGCGAC
 E   L   T   K   N   Q   V   S   L   T   C   L   V   K   G   F   Y   P   S   D
ATCGCCGTGGAGTGGGAGAGCAATGGGCAGCCGGAGAACAACTACAAGACCACGCCTCCC
 I   A   V   E   W   E   S   N   G   Q   P   E   N   N   Y   K   T   T   P   P
GTGCTGGACTCCGACGGCTCCTTCTTCCTCTACAGCAAGCTCACCGTGGACAAGAGCAGG
 V   L   D   S   D   G   S   F   F   L   Y   S   K   L   T   V   D   K   S   R
TGGCAGCAGGGGAACGTCTTCTCATGCTCCGTGATGCATGAGGCTCTGCACAACCACTAC
 W   Q   Q   G   N   V   F   S   C   S   V   M   H   E   A   L   H   N   H   Y
ACGCAGAAGAGCCTCTCCCTGTCTCCGGGTAAATGA
 T   Q   K   S   L   S   L   S   P   G   K   •
```

Figure 19

```
ATGAGTGTGCCCACTCAACTCCTGGGGTTGCTGCTGCTGTGGCTTACAGACGCACGATGT
 M  S  V  P  T  Q  L  L  G  L  L  L  L  W  L  T  D  A  R  C
GACATCCAGATGACTCAGTCTCCATCCTCCCTGTCTGCATCTGTGGGAGACAGAGTCACC
 D  I  Q  M  T  Q  S  P  S  S  L  S  A  S  V  G  D  R  V  T
ATCACATGTCGAGCAAGTGAGAACATTTACTACAGTTTAGCATGGTATCAGCAGAAGCCA
 I  T  C  R  A  S  E  N  I  Y  Y  S  L  A  W  Y  Q  Q  K  P
GGGAAAGCCCCTAAGCTCCTGATCTATAATGCAAACAGCTTGGAAGATGGTGTCCCATCG
 G  K  A  P  K  L  L  I  Y  N  A  N  S  L  E  D  G  V  P  S
AGGTTCAGTGGCAGTGGATCTGGGACACAGTATACTCTCACCATCAGCAGCCTGCAGCCT
 R  F  S  G  S  G  S  G  T  Q  Y  T  L  T  I  S  S  L  Q  P
GAAGATTTTGCAACTTATTACTGTAAACAGGCTTATGACGTTCCGTACACGTTCGGACAA
 E  D  F  A  T  Y  Y  C  K  Q  A  Y  D  V  P  Y  T  F  G  Q
GGGACCAAGGTGGAAATCAAACGAACTGTGGCTGCACCATCTGTCTTCATCTTCCCGCCA
 G  T  K  V  E  I  K  R  T  V  A  A  P  S  V  F  I  F  P  P
TCTGATGAGCAGTTGAAATCTGGAACTGCCTCTGTTGTGTGCCTGCTGAATAACTTCTAT
 S  D  E  Q  L  K  S  G  T  A  S  V  V  C  L  L  N  N  F  Y
CCCAGAGAGGCCAAAGTACAGTGGAAGGTGGATAACGCCCTCCAATCGGGTAACTCCCAG
 P  R  E  A  K  V  Q  W  K  V  D  N  A  L  Q  S  G  N  S  Q
GAGAGTGTCACAGAGCAGGACAGCAAGGACAGCACCTACAGCCTCAGCAGCACCCTGACG
 E  S  V  T  E  Q  D  S  K  D  S  T  Y  S  L  S  S  T  L  T
CTGAGCAAAGCAGACTACGAGAAACACAAAGTCTACGCCTGCGAAGTCACCCATCAGGGC
 L  S  K  A  D  Y  E  K  H  K  V  Y  A  C  E  V  T  H  Q  G
CTGAGCTCGCCCGTCACAAAGAGCTTCAACAGGGGAGAGTGTTAG
 L  S  S  P  V  T  K  S  F  N  R  G  E  C  •
```

GENERATION, EXPRESSION AND CHARACTERIZATION OF THE HUMANIZED K33N MONOCLONAL ANTIBODY

CROSS-REFERENCE TO RELATED APPLICATIONS

This application is the national phase of PCT application PCT/JP2010/054483 having an international filing date of 10 Mar. 2010, which claims benefit of U.S. provisional application Nos. 61/158,885 filed 10 Mar. 2009 and 61/251,072 filed 13 Oct. 2009. The contents of the above patent applications are incorporated by reference herein in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 643102001400SeqList.txt, date recorded: Dec. 11, 2013, size: 44,527 bytes).

1. TECHNICAL FIELD

The present invention relates to humanized antibodies that immunospecifically recognize human α9 integrin and to their therapeutic and diagnostic uses for various diseases or disorders that are associated with or involve α9 integrin, including cancer, inflammatory diseases, autoimmune diseases, disease conditions induced by α9 integrin, and the like.

2. BACKGROUND ART

Cells adhere to extracellular matrix (hereinafter abbreviated as ECM) mediated by a group of cell surface receptors which are termed integrins. Integrins perform their functions by forming 1:1 heterodimers of α and β chains. At least 18 types of α chain, 8 types of β chain and 24 types of αβ heterodimer have been identified and confirmed so far. It is known that each integrin recognizes a specific ligand. Integrins are classified into subfamilies depending upon their ligand specificities or functions, and divided into collagen receptors, laminin receptors, RGD receptors recognizing an Arg-Gly-Asp (RGD) sequence present in fibronectin, vitronectin, etc., and leukocyte-specific receptors present only in leukocytes (Hynes, R. O., 2002, Integrins: Bidirectional, Allosteric Signaling Machines. *Cell* 110: 673-87; Miyasaka, M., 2000, New edition of *Adhesion Molecule Handbook*, Shujunsya). The α4 and α9 integrins are members of a subfamily that does not belong to any of these types and called the α4 integrin subfamily (Elise L. Palmer, Curzio Rfiegg, Ronald Ferrando, Robert Pytela, Sheppard D., 1993, Sequence and Tissue Distribution of the Integrin α9 Subunit, a Novel Partner of β1 That Is Widely Distributed in Epithelia and Muscle. *The Journal of Cell Biology*, 123: 1289-97). Meanwhile, ECM used to be considered so far to serve as a mere cementing substance between cells. It has now become clear that the integrin-mediated ECM-cell interaction is significantly involved in regulating the growth, adhesion, movement, etc. of cells and associated with the onset of diseases including a progression of cancer, an exacerbation of inflammation, and the like.

For example, osteopontin (hereinafter abbreviated as OPN) which is one of the ECMs is a secreted, acidic phosphorylated glycoprotein with a molecular weight of about 41 kDa and is a molecule, whose expression is widely observed in breast milk, urine, renal tubules, osteoclasts, osteoblasts, macrophages, activated T cells, tumor tissues, and so forth. OPN has the adhesion sequences, GRGDS (SEQ ID NO:1) at the center of its molecule, the SVVYGLR (SEQ ID NO:2) sequence in human OPN or the SLAYGLR (SEQ ID NO:3) sequence in mouse OPN, and a thrombin-cleavage site in close proximity thereto, and binds through the GRGDS (SEQ ID NO:1) sequence to the RGD integrin or to the α4 (α4β1) and α9 (α9β1) integrins through the SVVYGLR (SEQ ID NO:2) sequence or the SLAYGLR (SEQ ID NO:3) sequence.

WO 02/081522 discloses a therapeutic effect on rheumatoid arthritis or hepatitis by inhibiting the OPN functions using OPN knockout mice or neutralizing antibodies against OPN. Moreover, this publication discloses that the SVVYGLR (SEQ ID NO:2) sequence is essential as recognizing the α9 and α4 integrins for pathogenesis of an inflammatory disease and that receptors for OPN are expressed in immunocompetent cells or the like and associated with an inflammatory disease.

Differences in binding profile have been found in that α4β1 binds both to OPN not cleaved with thrombin (uncleaved OPN) and to the N-terminal fragment of thrombin-cleaved OPN (cleaved OPN), whereas α9β1 binds only to the cleaved OPN (Y. Yokosaki, et al., (1999) *The Journal of Biological Chemistry* 274: 36328-36334; P. M. Green, et al., (2001) *FEBS Letters*, 503: 75-79; S. T. Barry, et al., (2000) *Experimental Cell Research*, 258: 342-351).

The α4 and α9 integrins share many common ligands other than OPN. Known ligands are the EDA domain of fibronectin, propeptide-von Willebrand factor (pp-vWF), tissue transglutaminase (tTG), blood coagulation factor XIII, vascular cell adhesion molecule-1 (VCAM-1), etc. In addition, the CS-1 domain of fibronectin, MadCAM-1 (α4β7), etc. are known as the ligands specifically recognized by the α4 integrin. Tenascin-C, plasmin, etc. are known as the ligands specifically recognized by the α9 integrin.

The amino acid sequences for the integrin subunits α9, α4 and β1 are publicly known. For instance, human α9 is registered as NM_002207, mouse α9 as NM_133721, human α4 as NM_000885, mouse α4 as NM_010576, human β1 as X07979, and mouse 131 as NM_010578, at the GenBank™. These integrins are also known to have high similarities between species in amino acid sequence.

3. SUMMARY OF THE INVENTION

While a variety of drugs are known at present for the treatment of cancer, inflammatory diseases and autoimmune diseases, it has been desired to develop a preventive and/or therapeutic agent, etc. having more improved therapeutic effects on cancer, inflammatory diseases and autoimmune diseases. The present invention is based, in part, on the discovery by the present inventors that a specific inhibitory antibody against the α9 integrin has cancer-suppressing and anti-inflammatory effects.

Previously, the present inventors isolated mouse monoclonal antibody that immunospecifically recognizes human α9 integrin and is produced by hybridoma clones, K33N (Depository Accession No. FERM BP-10830). Herein, the hybridoma clone designation is interchangeably used as the designation of the monoclonal antibody produced by the clone. The mouse anti-human α9 integrin antibody was of IgG1 isotype. The monoclonal antibody inhibits the binding between human and/or mouse α9 integrin and a ligand of α9 integrin, such as osteopontin. Thus, the anti-α9 integrin antibody inhibits the α9 integrin functions and exhibits therapeutic effects on cancer, e.g., the growth or metastasis of cancer cells, and on inflammatory diseases, e.g., rheumatoid arthritis, osteoarthritis, hepatitis, bronchial asthma, fibrosis, diabetes mellitus, arteriosclerosis, multiple sclerosis, granuloma, an inflammatory bowel disease (ulcerative colitis and Crohn's disease), an autoimmune disease, disease conditions induced by α9 integrin, and the like.

Furthermore, the anti-α9 integrin antibody of the present invention can be used as an in vivo diagnostic agent to detect the presence and the level of α9 integrin expression in a subject, thereby diagnosing a disorder or a disease involving α9 integrin.

However, since the monoclonal antibody is of mouse origin, possible adverse effects due to its immunogenicity in humans have hampered its direct applications to diagnostic or therapeutic uses in humans. In order to reduce the immunogenicity, the present inventors have prepared a humanized antibody that have biological activities corresponding to those exhibited by the original mouse anti-α9 integrin antibody from which said humanized antibody was derived.

Accordingly, the present invention provides a humanized antibody or an antigen-binding fragment thereof, which immunospecifically recognizes human α9 integrin, said antibody comprising an antigen-binding region partially derived from a non-human origin and partially derived from a human origin. In a specific embodiment, the humanized antibody or an antigen-binding fragment thereof of the present invention comprises a complementarity determining region (CDR) derived from a non-human source (donor), such as K33N monoclonal antibody, and a framework region (FR) derived from a human source (acceptor). In one embodiment, said humanized antibody or an antigen-binding fragment thereof inhibits the binding between human α9 integrin and a ligand of human α9 integrin.

In a specific embodiment, said humanized antibody or an antigen-binding fragment thereof that immunospecifically recognizes human α9 integrin comprises: (i) a heavy chain (H-chain) comprising at least one H-chain FR (FRH) derived from a variable region (V-region) of a human H-chain, and at least one H-chain complementarity determining region (CDRH) derived from at least one of the CDRHs of a non-human antibody K33N that immunospecifically recognizes human α9 integrin; or (ii) a light chain (L-chain) comprising at least one L-chain FR (FRL) derived from a V-region of a human L-chain, and at least one L-chain complementarity determining region (CDRL) derived from at least one of the CDRLs of a non-human antibody K33N that immunospecifically recognizes human α9 integrin; or both (i) and (ii) above. For example, said non-human antibody, from which at least one of the CDRHs and/or at least one of the CDRLs of the humanized antibody of the invention is derived, is a monoclonal antibody produced by a hybridoma of Accession No. FERM BP-10830.

In a preferred specific embodiment, the humanized antibody or an antigen-binding fragment thereof, of the present invention comprises: (i) at least one FRH derived from a human FRH, and at least one CDRH comprising an amino acid sequence selected from the group consisting of the amino acid sequences of SEQ ID NOS:4, 5 and 6; or (ii) at least one FRL derived from a human FRL, and at least one CDRL comprising an amino acid sequence selected from the group consisting of the amino acid sequences of SEQ ID NOS:11, 12 and 13; or (iii) both (i) and (ii) above. Said humanized antibody or an antigen-binding fragment thereof, of the present invention may comprise CDRH1, CDRH2 and CDRH3, which comprise the amino acid sequences of SEQ ID NOS:4, 5 and 6, respectively. In the alternative, said humanized antibody or an antigen-binding fragment thereof, of the present invention comprises CDRL1, CDRL2 and CDRL3, which comprise the amino acid sequences of SEQ ID NOS: 11, 12 and 13, respectively. In a preferred embodiment, said humanized antibody or an antigen-binding fragment thereof, of the present invention comprises CDRH1, CDRH2, CDRH3, CDRL1, CDRL2 and CDRL3, which comprise the amino acid sequences of SEQ ID NOS:4, 5, 6, 11, 12 and 13, respectively. In another alternative, said humanized antibody or an antigen-binding fragment thereof, of the present invention comprises a FRH derived from a variable region of a human H-chain encoded by GenBank™ Accession No. DA980102 (SEQ ID NO:18), or a FRL derived from a variable region of a human κ-L-chain encoded by GenBank™ Accession No. X72441 (SEQ ID NO:23). In a preferred embodiment, the FRH of the humanized antibody of the present invention comprises at least one amino acid sequence selected from the group consisting of the amino acid sequences of SEQ ID NOS:19, 20, 21 and 22 (FRH1, FRH2, FRH3 and FRH4, respectively, encoded by the corresponding portions of DA980102). In another preferred embodiment, the FRL of the humanized antibody of the present invention comprises at least one amino acid sequence selected from the group consisting of the amino acid sequences of SEQ ID NOS:24, 25, 26 and 27 (FRL1, FRL2, FRL3 and FRL4, respectively, encoded by the corresponding portions of X72441). In a more preferred embodiment, the humanized antibody or an antigen-binding fragment thereof, of the present invention comprises: (i) a H-chain variable region (VH region) comprising the amino acid sequence of SEQ ID NO:29; or (ii) a L-chain variable region (VL region) comprising the amino acid sequence of SEQ ID NO:31; or (iii) both (i) and (ii) above. In a most preferred embodiment, the humanized antibody or an antigen-binding fragment thereof, of the present invention comprises: (i) a gamma-1 H-chain comprising the amino acid sequence of SEQ ID NO:37; or (ii) a kappa L-chain comprising the amino acid sequence of SEQ ID NO:39; or (iii) both (i) and (ii) above.

The present invention further provides an isolated nucleic acid molecule comprising a nucleotide sequence encoding the humanized antibody or an antigen-binding fragment thereof of the present invention which immunospecifically recognizes human α9 integrin. Specifically, the present invention provides an isolated nucleic acid molecule comprising a nucleotide sequence encoding a humanized H-chain comprising at least one amino acid sequence selected from the group consisting of SEQ ID NOS:4, 5 and 6, or a humanized L-chain comprising at least one amino acid sequence selected from the group consisting of SEQ ID NOS:11, 12 and 13, or both said humanized H-chain and said humanized L-chain. In a preferred specific embodiment, such an isolated nucleic acid molecule comprises the nucleotide sequence of SEQ ID NO:28, which encodes a VH region, or a nucleotide sequence encoding the amino acid sequence of SEQ ID NO:29. In another preferred specific embodiment, such an isolated nucleic acid molecule comprises the nucleotide sequence of SEQ ID NO:30, which encodes a VL region, or a nucleotide sequence encoding the amino acid sequence of SEQ ID NO:31. In yet another preferred specific embodiment, the isolated nucleic acid molecule of the present invention comprises the nucleotide sequences of both SEQ ID NO:28 and 30. In a preferred specific embodiment, such an isolated nucleic acid molecule comprises the nucleotide sequence of SEQ ID NO:36, which encodes a gamma-1 H-chain, or a nucleotide sequence encoding the amino acid sequence of SEQ ID NO:37. In another preferred specific embodiment, such an isolated nucleic acid molecule comprises the nucleotide sequence of SEQ ID NO:38, which encodes a kappa L-chain, or a nucleotide sequence encoding the amino acid sequence of SEQ ID NO:39. In yet another preferred specific embodiment, the isolated nucleic acid molecule of the present invention comprises the nucleotide sequences of both SEQ ID NO:36 and 38. In yet another preferred specific embodiment, the isolated nucleic acid molecule of the present invention further comprises a nucleotide sequence encoding a signal peptide of donor origin, such as the amino acid sequences of SEQ ID NOS:10 and 17, respectively, or of heterologous origin.

The present invention further provides a vector, e.g., an expression vector, comprising a nucleotide sequence encoding a H-chain or a L-chain, or both, of the humanized antibody or an antigen-binding fragment thereof of the present invention that immunospecifically recognizes human α9 integrin. In such a vector, the nucleotide sequence of the present invention may be operably linked to one or more regulatory elements. The nucleotide sequence of the present invention may include a nucleotide sequence encoding a signal peptide native to a non-human donor antibody from which a CDR is derived, or a signal peptide of heterologous origin.

Furthermore, the present invention provides a host cell comprising the nucleic acid molecule of the present invention, including a vector comprising the nucleic acid molecule of the present invention. In one embodiment, the present invention provides an isolated host cell comprising a first nucleic acid molecule encoding a humanized H-chain of the present invention and a second nucleic acid molecule encoding a humanized L-chain of the present invention, said first and second nucleic acid molecules are each operably linked to a regulatory element in such a way that the biologically functional humanized antibody or antigen-binding fragment thereof of the present invention is expressed.

Accordingly, the present invention further provides a method for preparing the humanized antibody of the present invention, comprising culturing the host cell of the invention under conditions so that the humanized antibody is expressed; and collecting the produced humanized antibody.

The present invention further provides a composition comprising at least one of the humanized antibodies of the present invention. In addition, the present invention provides a pharmaceutical composition for preventing or treating a disorder or disease that is associated with α9 integrin, comprising at least one of the humanized antibodies of the present invention, and a pharmaceutically acceptable carrier. Either of said compositions can further comprise another active compound that can additively or synergistically ameliorate the disorder or disease. Such an active compound includes, but not by way of limitation, anti-inflammatory compounds, chemotherapeutic compounds, and the like, as well as an antibody or an antigen-binding fragment thereof, such as an antibody that can immunospecifically bind human α4 integrin.

In another aspect, the present invention provides a method for preventing or treating a disorder or disease that is associated with or involves α9 integrin, said method comprising administering a prophylactically or therapeutically effective amount of at least one of the humanized antibodies of the present invention to a subject in need thereof. For such uses, the humanized antibody of the present invention may be conjugated to a therapeutic moiety that enhances the biological effect of the humanized antibody. Examples of such a therapeutic moiety include another antibody, such as anti-α4 antibody (e.g., to form a bispecific antibody), cytotoxins that are cytostatic or cytocidal, radioactive elements, and/or other therapeutic agents, including anti-inflammatory agents, antibiotics, and the like.

In yet another aspect, the present invention provides a method for diagnosing a disorder or disease, in a subject, that is associated with or involves α9 integrin, said method comprising administering a diagnostically effective amount of the humanized antibody of the present invention to a subject to be examined. For such diagnostic uses, the humanized antibody of the present invention may be labeled with detectable markers, such as radioactive elements.

3.1. Definitions

As used herein, the term "antibody" refers to an antibody molecule capable of immunospecifically binding to a desired antigen, such as the α9 integrin, and encompasses an antibody molecule as a whole or a fragment thereof, including an antigen-binding fragment.

The term "immunospecifically recognize" used herein refers to an ability of an antibody or an antigen-binding fragment thereof to bind specifically to a target polypeptide or protein, in particular, human α9 integrin. Such an antibody does not non-specifically bind to other polypeptides or proteins. However, an antibody or an antigen-binding fragment thereof that immunospecifically binds to the target polypeptide or protein (e.g., human α9 integrin) may cross-react with other antigens. For example, the humanized antibody or an antigen-binding fragment of the present invention that immunospecifically recognizes human α9 integrin may cross-react with, for example, α9 integrins of other species. Preferably, an antibody or an antigen-binding fragment thereof that immunospecifically binds to human α9 integrin does not cross-react with other antigens.

The term "an antigen-binding fragment" used herein refers to any fragment of an antibody that retains an ability to immunospecifically bind to a target polypeptide or protein, in particular, human α9 integrin and/or non-human α9 integrin, and includes single chain antibodies, Fab fragments, F(ab')$_2$ fragments, disulfide-linked Fvs, and fragments containing either a variable region of a light chain (VL) and/or a variable region of a heavy chain (VH) or even a complementary determining region (CDR) that specifically binds to a target polypeptide or protein. Thus, such antigen-binding fragments of humanized antibody may or may not include partial or full-length human constant regions. Various methods for obtaining the antibody fragments described above are well known in the art.

The term "derived from a human source" or "derived from a non-human source" used herein refers to an antibody portion whose amino acid sequence is derived from a corresponding portion of a human antibody or of a non-human antibody.

The term "an acceptor sequence" used herein refers to a nucleotide sequence or an amino acid sequence of framework regions from a human antibody VH or VL region that serves as an acceptor for CDRs from a donor antibody, which is usually a non-human antibody.

4. BRIEF DESCRIPTION OF THE FIGURES

FIG. 1 shows the result of experiments in which cell-adhesion inhibitory activity of anti-human alpha-9 integrin antibodies (i.e., two clones of the present invention (i.e., K33N and M35A), five other clones (1K11, 21C5, 24I11, 25B6, and 28S1), and Y9A2) was measured with a human alpha-9 integrin expressing cell (human melanoma cell G361) and an OPN alpha-9 integrin binding-site peptide (SV-VYGLR) (SEQ ID NO:64). A monoclonal antibody against human osteopontin (5A1) was used as a negative control.

FIG. 2 shows the result of experiments in which cell-adhesion inhibitory activity of anti-human alpha-9 integrin antibodies (i.e., two clones of the present invention (i.e., K33N and M35A), five other clones (1K11, 21C5, 24I11, 25B6, and 28S1), and Y9A2) was measured with a human alpha-9 integrin expressing cell (human melanoma cell G361) and an alpha-9 integrin binding-site peptide of a tenascin-C fragment. A monoclonal antibody against human osteopontin (5A 1) was used as a negative control.

FIG. 3 shows the nucleotide sequence (SEQ ID NO:7) of mouse K33N VH cDNA along with the deduced amino acid sequence (SEQ ID NO:8). Amino acid residues are shown in single letter code. The signal peptide sequence (SEQ ID NO:10) is in italic. The N-terminal amino acid residue (Q) of the mature VH is double-underlined. CDR sequences according to the definition of Kabat et al. (Sequences of Proteins of Immunological Interests, Fifth edition, NIH Publication No. 91-3242, U.S. Department of Health and Human Services, 1991) are underlined.

FIG. 4 shows the nucleotide sequence (SEQ ID NO:14) of mouse K33N VL cDNA along with the deduced amino acid sequence (SEQ ID NO:15). Amino acid residues are shown in single letter code. The signal peptide sequence (SEQ ID NO:17) is in italic. The N-terminal amino acid residue (D) of the mature VL is double-underlined. CDR sequences according to the definition of Kabat et al. (1991) are underlined.

FIG. 5 shows the nucleotide sequence (SEQ ID NO:32) of the designed K33N VH (ChK33N VH) gene flanked by SpeI and HindIII sites (underlined), along with the deduced amino acid sequence (SEQ ID NO:8). Amino acid residues are shown in single letter code. The signal peptide sequence (SEQ ID NO:10) is in italic. The N-terminal amino acid residue (Q) of the mature VH is double-underlined. CDR sequences according to the definition of Kabat et al. (1991) are underlined. The intron sequence is in italic.

FIG. 6 shows the nucleotide sequence (SEQ ID NO:33) of the designed K33N VL (ChK33N VL) gene flanked by NheI and EcoRI sites (underlined), along with the deduced amino acid sequence (SEQ ID NO:15). Amino acid residues are shown in single letter code. The signal peptide sequence (SEQ ID NO:17) is in italic. The N-terminal amino acid residue (D) of the mature VL is double-underlined. CDR sequences according to the definition of Kabat et al. (1991) are underlined. The intron sequence is in italic.

FIG. 7 shows the schematic structure of pChK33N and pHuK33N (collectively Expression Vector). Proceeding clockwise from the SalI site at the top, the plasmid contains the heavy chain transcription unit starting with the human cytomegalovirus (CMV) major immediate early promoter and enhancer (CMV promoter) to initiate transcription of the antibody heavy chain gene. The CMV promoter is followed by the VH exon, a genomic sequence containing the human gamma-1 heavy chain constant region including the CH1, hinge, CH2 and CH3 exons with the intervening introns, and a polyadenylation site of the gamma-1 gene for mRNA processing following CH3. After the heavy chain gene sequence, the light chain transcription unit begins with the CMV promoter, followed by the VL exon and a genomic sequence containing the human kappa chain constant region exon (CL) with part of the intron preceding it, and a poly A signal of the kappa gene. The light chain gene is then followed by the SV40 early promoter (SV40 promoter), the E. coli xanthine guanine phosphoribosyl transferase gene (gpt), and a segment containing the SV40 polyadenylation site (SV40 poly(A) site). Finally, the plasmid contains a part of the plasmid pUC19, comprising the bacterial origin of replication (pUC ori) and beta-lactamase gene (beta lactamase).

FIG. 8 shows the alignment of the amino acid sequences of K33N VH (SEQ ID NO:9), humanized K33N (HuK33N) VH (SEQ ID NO:29) and FRH1 (SEQ ID NO:19), FRH2 (SEQ ID NO:20), FRH3 (SEQ ID NO:21) and FRH4 (SEQ ID NO:22) of human acceptor sequences, derived from the amino acid sequence encoded by the nucleotide sequence of GenBank™ accession number DA980102. Amino acid residues are shown in single letter code. Numbers above the sequences indicate the locations according to Kabat et al. (1991). CDR sequences defined by Kabat et al. (1991) are underlined. Double-underlined residues were predicted to contact with the CDRs and the mouse residues were retained at these locations in the humanized form. Met at position 82 in DA980102 (underlined), that is atypical at this position in human VH sequences, was replaced with a typical residue Leu to reduce potential immunogenicity. CDR residues in DA980102 are omitted in the figure.

FIG. 9 shows the alignment of the amino acid sequences of K33N VL (SEQ ID NO:16), humanized K33N (HuK33N) VL (SEQ ID NO:31) and FRL1 (SEQ ID NO:24), FRL2 (SEQ ID NO:25), FRL3 (SEQ ID NO:26) and FRL4 (SEQ ID NO:27) of human acceptor sequences, derived from the amino acid sequence encoded by the nucleotide sequence of GenBank™ accession number X72441. Amino acid residues are shown in single letter code. Numbers above the sequences indicate the positions according to Kabat et al. (1991). CDR sequences defined by Kabat et al. (1991) are underlined. Double-underlined residues were predicted to contact with the CDRs and the mouse residues were retained at these locations in the humanized form. CDR residues in X72441 are omitted in the figure.

FIG. 10 shows the oligonucleotides used for construction of the HuK33N VH gene.

FIG. 11 shows the oligonucleotides used for construction of the HuK33N VL gene.

FIG. 12 shows the oligonucleotides used for construction of the HuK33N VH gene. An arrow denotes the position and orientation (5' to 3') of each oligonucleotide. Amino acid residues of the VH region (SEQ ID NO:29) are shown in single letter code.

FIG. 13 shows the oligonucleotides used for construction of the HuK33N VL gene. An arrow denotes the position and orientation (5' to 3') of each oligonucleotide. Amino acid residues of the VL region (SEQ ID NO:31) are shown in single letter code.

FIG. 14 shows the nucleotide sequence of the HuK33N VH gene flanked by SpeI and HindIII sites (underlined) (SEQ ID NO:34) is shown along with the deduced amino acid sequence of the signal peptide (SEQ ID NO:58; shown in italic) and the VH region (SEQ ID NO:29). Amino acid residues are shown in single letter code. The signal peptide sequence is in italic. The N-terminal amino acid residue (Q) of the mature VH is double-underlined. CDR sequences according to the definition of Kabat et al. (1991) are underlined. The intron sequence is in italic.

FIG. 15 shows the nucleotide sequence of the HuK33N VL gene flanked by NheI and EcoRI sites (underlined) (SEQ ID NO:35) is shown along with the deduced amino acid sequence of the signal peptide (SEQ ID NO:59; shown in italic) and the VL region (SEQ ID NO:31). Amino acid residues are shown in single letter code. The signal peptide sequence is in italic. The N-terminal amino acid residue (D) of the mature VL is double-underlined. CDR sequences according to the definition of Kabat et al. (1991) are underlined. The intron sequence is in italic.

Figure 16:
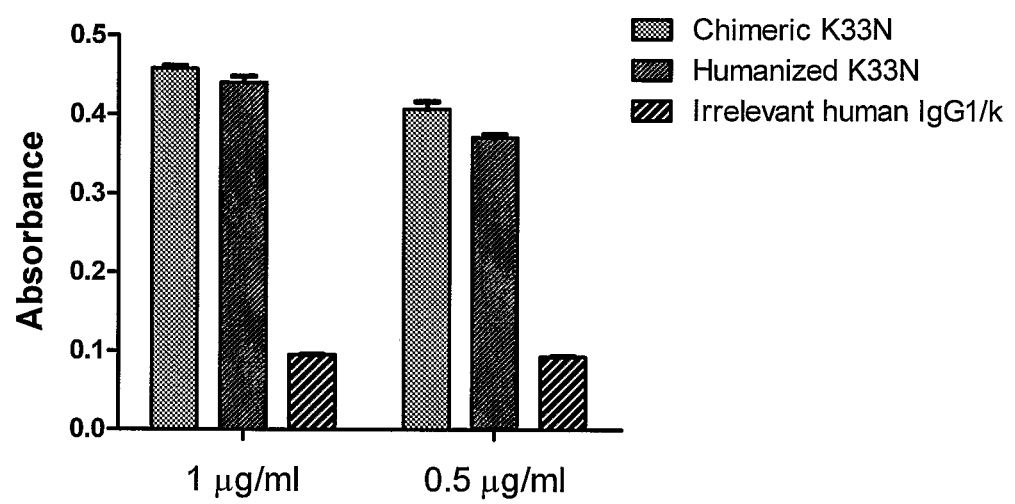

FIG. 16 shows the comparison of the affinity of chimeric and humanized K33N antibodies to human α9 integrin. The binding of chimeric and humanized K33N at 1 and 0.5 μg/ml to CHO/α9 cells was examined by cell ELISA. Experiments were carried out in triplicate. The mean absorbance value with SEM is shown in the figure.

FIG. 17 shows the sequences of oligonucleotides used for PCR amplification and sequencing of HuK33N heavy and light chain cDNA (SEQ ID NO:44-50).

FIG. 18 shows the nucleotide sequence of the coding region of HuK33N gamma-1 heavy chain (SEQ ID NO:36) in pHuK33N is shown along with the deduced amino acid sequence (SEQ ID NO:37). Amino acid residues are shown in single letter code. A termination codon is denoted by "•".

FIG. 19 shows the nucleotide sequence of the coding region of HuK33N kappa light chain (SEQ ID NO:38) in pHuK33N is shown along with the deduced amino acid sequence (SEQ ID NO:39). Amino acid residues are shown in single letter code. A termination codon is denoted by "•".

Figure 20:
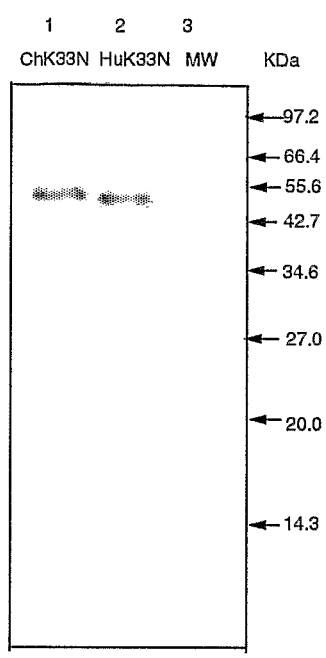

FIG. 20 shows the result of SDS-PAGE analysis of purified antibodies. Six μg of chimeric and humanized IgG1/κ antibodies (ChK33N and HuK33N, respectively) were run on a 10% polyacrylamide gel in the presence of SDS under reducing conditions according to Sambrook et al. (Molecular Cloning, A Laboratory Manual, 2nd ed., 1989, Cold Spring Harbor Laboratory Press, Cold Spring Harbor, N.Y.). Broad Range Protein Marker (MW; New England Biolabs, Ipswich, Mass.) was used as size markers. Numbers shown at the right side denote the size of markers in kilo Dalton (kDa).

Figure 21:
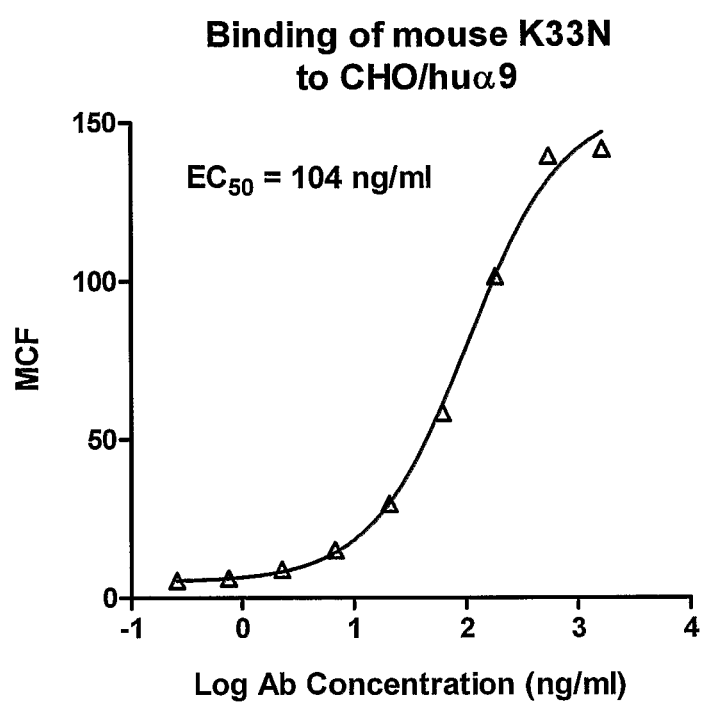

FIG. 21 shows the result of FACS™ (BD Biosciences, Franklin Lakes, N.J.) analysis of the binding of mouse K33N antibody to human α9 integrin. Mouse K33N antibody was tested at various concentrations, starting at 1.67 μg/ml and serial 3-fold dilutions, for binding to CHO/huα9 cells. Geometric mean channel fluorescence values (MCF; Y-axis) are plotted at each antibody concentration tested (X-axis) in the figure. $EC_{50}$ values were calculated using GraphPad Prism® (GraphPad Software, San Diego, Calif.).

Figure 22:
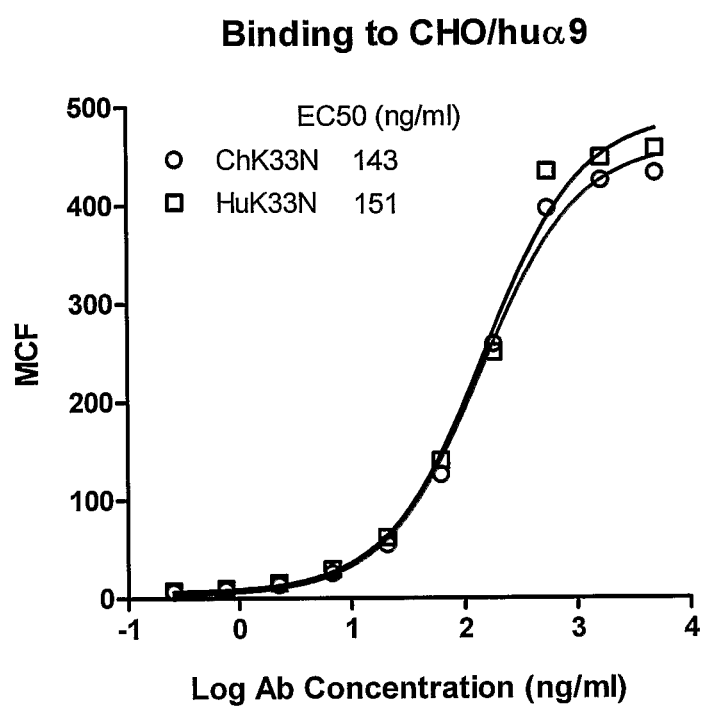

FIG. 22 shows the results of FACS™ analysis of the binding of chimeric and humanized K33N antibodies to human α9 integrin. Each antibody was tested at various concentrations, starting at 5 μg/ml and serial 3-fold dilutions, for binding to CHO/huα9 cells. Geometric mean channel fluorescence values (MCF; Y-axis) are plotted at each antibody concentration tested (X-axis) in the figure. $EC_{50}$ values were calculated using GraphPad Prism® (GraphPad Software, San Diego, Calif.).

Figure 23:
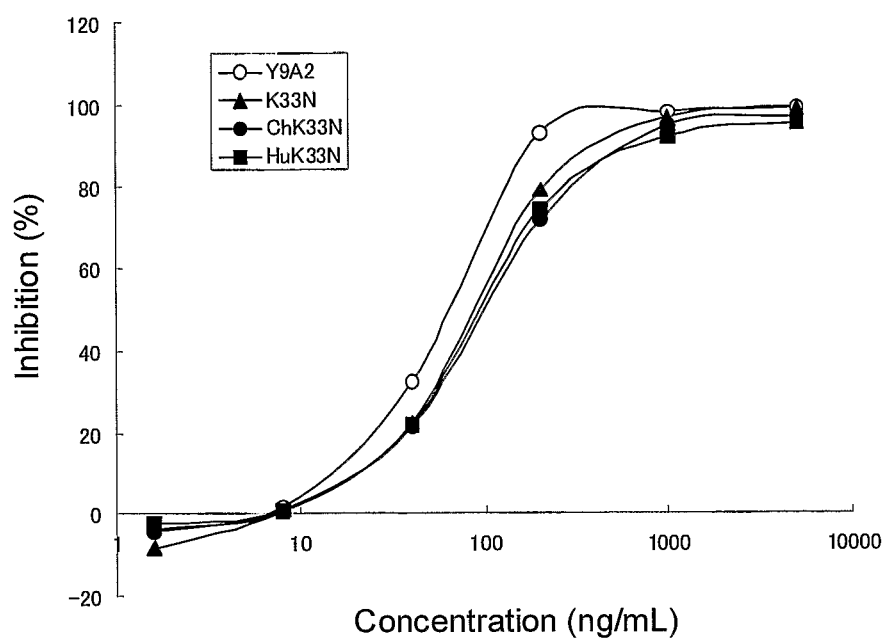

FIG. 23 shows the dose-responsive cell adhesion inhibition rate of mouse, chimeric and humanized K33N antibodies to human α9 integrin and mouse anti human α9 integrin antibody Y9A2. Each antibody was tested at the concentrations of 5, 1, 0.2, 0.04, 0.008 and 0.0016 μg/mL for cell adhesion of human α9 integrin espressed cell line G-361. Experiments were carried out in quartet. The mean inhibition rate value is shown in the figure.

5. MODE FOR CARRYING OUT THE INVENTION 5.1. Preparation of Antibodies Against Human α9 Integrin Antibodies that immunospecifically recognize human α9 integrin or any epitope thereof may be generated by any suitable method known in the art.

The α9 integrin used as an antigen in the present invention may be (1) proteins derived from all cells from human that express α9 integrin, or all tissues where these cells are present, (2) recombinant proteins in which the α9 integrin-encoding gene DNA, preferably cDNA, is transfected into bacteria, yeast, cell lines including animal cells, etc. and expressed, or (3) synthetic proteins.

The α9 integrin includes polypeptides comprising substantially the same amino acid sequences as the amino acid sequences of human α9 integrins (SEQ ID NO:55, wherein 1-29 residues are the signal peptide).

Herein, the term "polypeptides comprising substantially the same amino acid sequence" means variant polypeptides comprising an amino acid sequence, in which multiple amino acids, preferably 1 to 10 amino acids and more preferably 1 to several (e.g., 1 to 5) amino acids are substituted, deleted and/or modified, as long as these variant polypeptides have biological properties substantially equivalent to the naturally occurring human α9 integrin; and variant polypeptides comprising an amino acid sequence, wherein multiple amino acids, preferably 1 to 10 amino acids and more preferably 1 to several (e.g., 1 to 5) amino acids are added to the amino acid sequence of naturally occurring human α9 integrin. Furthermore, the variant polypeptides may be those having a plurality of these substitutions, deletions, modifications and additions of amino acids.

The human α9 integrin as an antigen in the present invention can be produced by methods well known in the art, such as chemical synthesis method, cell culture method, etc., or their modifications, in addition to the gene recombinant techniques.

Examples of the methods for producing variant polypeptides include a synthetic oligonucleotide site-directed mutagenesis (gapped duplex method), a point mutagenesis method which involves introducing a point mutation at random by treatment with nitrite or sulfite, a method which involves preparing a deletion mutant with Bal31 enzyme, or other enzymes, a cassette mutagenesis, a linker scanning method, a miss incorporation method, a mismatch primer method, a DNA segment synthesis method, and the like.

The human α9 integrin to be used as an antigen in the present invention also includes a "part" of said α9 integrin. As used herein, the "part" refers to a part comprising a region required for binding to a ligand of the α9 integrin, for example, OPN, VCAM-1, tenascin-C, etc.; specifically, a part comprising the 14th-980th amino acid residues, and a part comprising the 11th-981st amino acid residues, of the mature human α9 integrin (the 30th-1035th amino acid residues of SEQ ID NO:55). The "part" of said α9 integrin can be produced by gene recombination or chemical synthesis according to methods known in the art described below, or modifications thereof, or can be produced by appropriately digesting the human α9 integrin isolated by the cell culture method with a proteolytic enzyme or the like.

As an antigen, a cell per se that overexpresses the α9 integrin on the cell membrane, or a membrane fraction thereof, can be also used. Cells overexpressing human α9 integrin can be prepared by recombinant DNA technologies well known in the art.

Using appropriate antigens prepared as described above, antibodies specific for human α9 integrin or any epitope thereof may be prepared by various methods well known in the art. Polyclonal antibodies to human α9 integrin can be produced by various procedures well known in the art. For example, an antigen of interest can be administered to various host animals including, but not limited to, rabbits, mice, rats, etc., to induce the production of antisera containing polyclonal antibodies specific for the antigen. Various adjuvants may be used to increase the immunological response, depending on the host species, and include but are not limited to, Freund's (complete and incomplete) adjuvant, mineral gels such as aluminum hydroxide, surface active substances such as lysolecithin, pluronic polyols, polyanions, peptides, oil emulsions, keyhole limpet hemocyanins, dinitrophenol, and potentially useful adjuvants for humans such as BCG (Bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas, pp. 563-681 (Elsevier, N.Y., 1981) (both of which are incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice can be immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well known techniques to any suitable myeloma cells (e.g., P3U1, P3X63-Ag8, P3X63-Ag8-U1, P3NS1-Ag4, SP2/0-Ag14, P3X63-Ag8-653, etc.). Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

Antibody fragments what recognize specific epitopes may be generated by known techniques. For example, Fab and $F(ab')_2$ fragments may be produced by proteolytic cleavage of immunoglobulin molecules, using enzymes such as papain (to produce Fab fragments) or pepsin (to produce $F(ab')_2$ fragments). $F(ab')_2$ fragments contain the complete light chain, and the variable region, the CH1 region and the hinge region of the heavy chain.

The antibodies of the invention or an antigen-binding fragment thereof can be also produced by any method known in the art for the synthesis of antibodies, in particular, by chemical synthesis or preferably, by recombinant expression techniques.

The nucleotide sequence encoding an antibody may be obtained from any information available to those skilled in the art (i.e., from GenBank™, the literature, or by routine cloning and sequence analysis). If a clone containing a nucleic acid encoding a particular antibody or an epitope-binding fragment thereof is not available, but the sequence of the antibody molecule or epitope-binding fragment thereof is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from any tissue or cells expressing the antibody, such as hybridoma cells selected to express an antibody) by PCR amplification using synthetic primers hybridizable to the and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

5.2. Preparation of Recombinant Antibodies

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., supra; and Ausubel et al., eds., 1998, Current Protocols in Molecular Biology, John Wiley & Sons, NY, which are both incorporated by reference herein in their entireties), to generate antibodies having a different amino acid sequence by, for example, introducing amino acid substitutions, deletions, and/or insertions into the epitope-binding domain regions of the antibodies or any portion of antibodies which may enhance or reduce biological activities of the antibodies.

Recombinant expression of an antibody requires construction of an expression vector containing a nucleotide sequence that encodes the antibody. Once a nucleotide sequence encoding an antibody molecule or a heavy or light chain of an antibody, or portion thereof has been obtained, the vector for the production of the antibody molecule may be produced by recombinant DNA technology using techniques well known in the art as discussed in the previous sections. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The nucleotide sequence encoding the heavy-chain variable region, light-chain variable region, both the heavy-chain and light-chain variable regions, an epitope-binding fragment of the heavy- and/or light-chain variable region, or one or more complementarity determining regions (CDRs) of an antibody may be cloned into such a vector for expression. Such a sequence may be fused with a polynucleotide encoding a signal peptide native to the original antibody or a heterologous signal peptide. Thus-prepared expression vector can be then introduced into appropriate host cells for the expression of the antibody. Accordingly, the invention includes host cells containing a polynucleotide encoding a humanized antibody or an antigen-binding fragment thereof that immunospecifically recognizes human α9 integrin.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides or different selectable markers to ensure maintenance of both plasmids. Alternatively, a single vector may be used which encodes, and is capable of expressing, both heavy and light chain polypeptides. The coding sequences for the heavy and light chains may comprise cDNA or genomic DNA.

In another embodiment, antibodies can also be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene I10 or gene VIII protein. Examples of phage display methods that can be used to make the immunoglobulins, or fragments thereof, of the present invention include those disclosed in Brinkman et al., J. Immunol. Methods, 182:41-50, 1995; Ames et al., J. Immunol. Methods, 184:177-186, 1995; Kettleborough et al., Eur. J. Immunol., 24:952-958, 1994; Persic et al., Gene, 187:9-18, 1997; Burton et al., Advances in Immunology, 57:191-280, 1994; PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques, 12(6):864-869, 1992; and Sawai et al., AJR1, 34:26-34, 1995; and Better et al., Science, 240:1041-1043, 1988 (each of which is incorporated by reference in its entirety). Examples of techniques which can be used to produce single-chain Fvs and antibodies include those described in U.S. Pat. Nos. 4,946,778 and 5,258,498; Huston et al., Methods in Enzymology, 203:46-88, 1991; Shu et al., PNAS, 90:7995-7999, 1993; and Skerra et al., Science, 240:1038-1040, 1988.

Once an antibody molecule of the invention has been produced by any methods described above, it may then be purified by any method known in the art for purification of an immunoglobulin molecule, for example, by chromatography (e.g., ion exchange, affinity, particularly by affinity for the specific antigen after Protein A or Protein G purification, and sizing column chromatography), centrifugation, differential solubility, or by any other standard techniques for the purification of proteins. Further, the antibodies of the present invention or fragments thereof may be fused to heterologous polypeptide sequences described herein or otherwise known in the art to facilitate purification.

For some uses, including in vivo use of antibodies in humans and in vitro detection assays, it may be preferable to use chimeric, humanized, or human antibodies. Chimeric antibodies and humanized antibodies are discussed in details in Section 5.3, infra.

Antibodies fused or conjugated to other compounds or heterologous polypeptides may be used in in vitro immunoassays, in purification methods (e.g., affinity chromatography), as well as in vivo therapeutic or diagnostic uses. See e.g., PCT publication Number WO 93/21232; EP 439,095; Naramura et al., Immunol. Lett., 39:91-99, 1994; U.S. Pat. No. 5,474,981; Gillies et al., PNAS, 89:1428-1432, 1992; and Fell et al., J. Immunol., 146:2446-2452, 1991, which are incorporated herein by reference in their entireties. For example, antibodies can be labeled in various ways using a known method or commercially available kit (e.g., biotin labeling, FITC labeling, APC labeling). As another example, antibodies may be conjugated to a therapeutic moiety that enhances the biological effect of the antibodies in vivo. Examples of such a therapeutic moiety include another antibody, cytotoxins that are cytostatic or cytocidal, radioactive element, and/or other therapeutic agents, including anti-inflammatory agents, antibiotics, and the like. In the present invention, the humanized anti-human α9 integrin may be conjugated to another antibody, such as anti-α4 antibody (e.g., to form a bispecific antibody). As another example, the humanized antibody of the present invention may be labeled with detectable markers, such as radioactive elements, for in vivo diagnostic uses.

5.3. Chimeric and Humanized Antibodies

A chimeric antibody is a molecule in which different portions of the antibody are derived from different animal species, such as antibodies having a variable region derived from a murine monoclonal antibody and a constant region derived from a human immunoglobulin. Methods for producing chimeric antibodies are known in the art. See e.g., Morrison, Science, 229:1202, 1985; Oi et al., BioTechniques, 4:214 1986; Gillies et al., J. Immunol. Methods, 125:191-202, 1989; U.S. Pat. Nos. 5,807,715; 4,816,567; and 4,816,397, which are incorporated herein by reference in their entireties.

A humanized antibody is a molecule that binds a desired antigen and comprises a variable region containing one or more complementarity determining regions (CDRs) derived from a non-human species and one or more framework regions derived from a human immunoglobulin molecule. The typical methods for humanizing non-human antibodies have been described in various references, such as those: by Queen et al., 1989, *Proc. Natl. Acad. Sci. USA* 86:10029-10033 and U.S. Pat. Nos. 5,585,089 and 5,693,762; by Riechmann et al., *Nature,* 332:323, 1988; and by Tsurushita et al., *Methods* 36:69-83, 2005, all of which are incorporated herein by reference in their entireties). For example, the reference by Tsurushita et al. (2005, supra; hereafter "Tsurushita") provides a practical and instructive protocol for the humanization of mouse monoclonal antibodies based on the antibody-humanization method originally developed by Queen et al. (1989, supra). The general protocol disclosed in Tsurushita is briefly summarized below.

5.3.1. General Protocol for Preparing Humanized Antibodies

Cloning and Sequencing of Mouse V Genes

Various methods are available for cloning cDNAs encoding the VH and VL regions of a target mouse monoclonal antibody. For example, 5' RACE (rapid amplification of cDNA ends) method using SMART™ RACE cDNA Amplification Kit (BD Biosciences, CA) or the GeneRacer™ Kit (Invitrogen, CA) has been commonly used. A gene-specific primer for 5' RACE can be prepared based on the isotypes of the H-chain and the L-chain of the target monoclonal antibody so that it can bind immediately downstream of the variable region for each of the H-chain and L-chain. Thus, 5' RACE primer may be designed to be specific for each subtype in mouse, such as γ1, γ2a, γ2b or γ3. Alternatively, a common primer for all subtypes may be designed based on the consensus or highly homologous region among the subtypes. In Tsurushita, the following 5' RACE primers are disclosed as examples:

```
(i)     5'-GCCAGTGGATAGACTGATGG-    (SEQ ID NO: 56)
(for cloning of mouse γ1, γ2a, γ2b and
γ3 H-chains)

(ii)    5'-GATGGATACAGTTGGTGCAGC-   (SEQ ID NO: 57)
(for cloning of mouse κ light chains).
```

PCR-amplified V gene fragments can be directly cloned into a plasmid vector, for example, using the Zero Blunt® TOPO® PCR Cloning Kit (Invitrogen), and their DNA sequences determined. The obtained sequences should be confirmed by, for example, comparing their encoding amino acid sequences with those of the target monoclonal antibody determined by the N-terminal amino acid sequencing, using, for example a Model 241 Protein Sequencer (Hewlett-Packard, CA). Typically, the determination of at least 15-20 amino acid residues at the N-terminus of the target antibody, for example, by Edman degradation, is sufficient to confirm the authenticity of the cloned DNA sequences. Tsurushita cautions that when glutamine, which is one of the two most common N-terminal amino acid in mouse, is the N-terminal amino acid, it might have been converted to pyroglutamine and blocks the sequencing at the N-terminus. In that case, it is necessary to deblock the N-terminus to obtain the sequence.

Three-Dimensional Modeling of V Regions

Based on the sequences of the VH and VL regions, the framework residues of the target antibody that are potentially important for maintaining the conformational structure of the CDRs, are first identified by the method, for example, described by R. Levy et al., 1989, *Biochemistry* 28:7168-7175; and by B. Zilber et al., 1990, *Biochemistry* 29:10032-10041. Typically, each of the VH and VL regions is divided into 14 structurally meaningful segments, which are β strands and loop-like structures comprising the domain structure of the immunoglobulin superfamily. The amino acid sequence of each of the segments from the target antibody is aligned with the corresponding segments of antibodies of known structures, in the PDB database (see H. M. Berman et al., 2000, *Nucleic Acids Res.* 28:235-342). By multiple sequence alignment, a corresponding segment having the highest sequence homology to each of the target segment is selected and the three-dimensional model of the V-region is constructed. In order to optimize the structure, the model is subjected to multiple cycles of conjugate gradient energy minimization (e.g., using ENCAD, or as described by Press et al., 1990, in "*Numerical Recipes*, Cambridge University Press, Cambridge; AMBER by Weiner et al., 1981, *J. Comp. Chem.* 2:287-303; 3D-JIG-SAW available at BioMolecular-Modelling or "BMM" web site run by Cancer Research UK; or SWISS-MODEL available at ExPASy Proteomics Server web site run by Swiss Institute of Bioinformatics, Geneva).

Selection of Human Frameworks

In parallel with modeling the structure of the V regions, the amino acid sequences deduced from the cDNA cloning of the mouse VH and VL regions, respectively, are compared to human V region sequences in the databases, for example, the Kabat database (see Johnson et al., 2000, *Nucleic Acids Res.* 28:214-218), GenBank™, and so forth. Human framework regions that have overall sequence identity of at least about 65%, at least about 70%, at least about 75%, at least about 80%, at least about 85%, at least about 90%, or at least 95% identity, with the mouse sequence, can be searched using, for example, the Smith-Waterman algorithm (by Gusfield, 1997, in "*Algorithms on Strings, Trees, and Sequences*", Cambridge University Press, Cambridge), or BLAST (by Karlin et al., 1990, *Proc. Natl. Acad. Sci. USA* 87:2264-2268), and the like. These human sequences may be based on cDNA-based and protein-derived sequences; however, the use of germline is often preferable as it may be useful in eliminating potential immunogenicity associated with somatic hypermutations in cDNA-based, protein-derived sequences. In the alternative, as described in Queen et al. (1989, supra), the use of a consensus framework sequence can also identify and remove such hypermutated residues in the framework obtained from cDNA-based or protein-derived sequences. In the case where a germline VH segment is used as an acceptor framework, VH segments encoded on chromosome 14, rather than 15 and 16, should be used as only those on chromosome 14 produce functional VH regions.

Design of Humanized V Regions

According to Queen et al. (1989, supra), it is necessary to identify framework amino acids within about 4-6 Å of the CDRs as these residues are considered to be potential key framework residues that support the correct CDR structures. Such a process can be achieved using a computer program, such as RASMOL available at Molecular Visualization Freeware web site supported by National Science Foundation (NSF), that calculates interatomic distances from the atomic coordinates or, through manual inspection of a computer model. If amino acids at key framework positions are different between mouse donor and human acceptor sequences, those of mouse donor usually replace the human residues. However, if such residues have minimal contribution to support the CDR structures, the corresponding human residues are typically used. Also, if the selected human acceptor contains "atypical" amino acids, which occur in less than about 10-20% of the V region sequences, they may be the result of somatic hypermutation during affinity maturation and should be replaced with the donor residues in order to avoid potential immunogenicity in humans.

In addition, other factors, such as residues of potential N-linked glycosylation signals, need to be carefully considered in order to design humanized V regions (see Tsurushita for details).

Humanized antibodies may contain a human constant region or a portion thereof from the human κ or λ light chain, and/or the γ1, γ2, γ3, γ4, α1, α2, δ, or ε heavy chain of human antibodies, or variants thereof, depending on the effector functions required or to be eliminated for therapeutic uses. For example, a Fc portion of the constant region containing a mutation may be fused to the variable region of the chimeric or humanized antibody of the present invention so as to reduce the binding of the antibody to Fc receptors and/or to reduce its ability to fix complement (see, for example, Winter et al., GB 2,209,757 B; Morrison et al., WO 89/07142, Morgan et al., WO 94/29351). Such manipulations of antibody molecules can be carried out by recombinant DNA technology as described in Section 5.2.

Preferably the resulting chimeric or humanized antibody has the same specificity as the non-human donor antibody and an affinity similar to or at least about ⅓, at least about ½, or at least about ⅔, of that of the non-human donor antibody. In another aspect, the resulting chimeric or humanized antibody has an affinity constant of at least about $1 \times 10^7$ $M^{-1}$, preferably at least about $1 \times 10^8$ $M^{-1}$, and most preferably at least about $1 \times 10^9$ $M^{-1}$.

In addition to the general protocol described above, antibodies can be humanized using a variety of techniques known in the art including, for example, CDR-grafting (EP 239,400; PCT publication WO 91/09967; U.S. Pat. Nos. 5,225,539; 5,530,101 and 5,585,089), veneering or resurfacing (EP 592, 106; EP 519,596; Padlan, Molecular Immunology, 28(4/5): 489-498, 1991; Studnicka et al., Protein Engineering, 7(6): 805-814, 1994; Roguska et al., Proc Natl. Acad. Sci. USA, 91:969-973, 1994), and chain shuffling (U.S. Pat. No. 5,565, 332), all of which are hereby incorporated by reference in their entireties.

5.3.2. Additional Considerations for Preparing Humanized Antibodies as Pharmaceuticals To offer humanized antibodies as pharmaceuticals, an efficient and consistent production system therefor needs to be prepared. For example, an appropriate expression vector for humanized antibodies is prepared by inserting H- and L-chain sequences, and a high-productivity cell line transfected with the expression vector can be obtained as a seed cell for a master cell bank (MCB), which serves as a stable and semi-permanent source for a working cell bank (WCB). Humanized antibodies can be then prepared by culturing working cells from the WCB and collecting the culture medium.

Various expression vectors with appropriate regulatory genes can be used for the preparation of such a production cell line. As a host cell, those commonly used for expressing mammalian proteins can be used for the expression of humanized antibodies. Examples of such host cells include, but are not limited to, Chinese Hamster Ovary (CHO) cells, SP2/0-Ag14.19 cells, NSO cells, and the like. The productivity of humanized antibodies can be maximized by selecting the best combination of an expression vector and a host cell. Furthermore, the composition of culture media should be explored in order to select suitable media, from various serum-free culture media and supplements, so that the expression of humanized antibodies by the host cell can be optimized.

Based on the efficiency and the final yield, the humanized antibodies produced by the host cell can be purified from the culture supernatant using various methods well known in the art, including affinity chromatography, ion-exchange chromatography, hydrophobic interaction chromatography, and the like.

5.4. Pharmaceutical Composition and Therapeutic Uses

The present invention provides a pharmaceutical composition comprising the humanized antibody or an antigen-binding fragment thereof, described above, that immunospecifically recognizes human $\alpha 9$ integrin. The pharmaceutical composition comprising the humanized antibody of the present invention as an active ingredient can be used as an agent for preventing and/or treating a disorder or disease that is associated with $\alpha 9$ integrin, including, but not limited to, cancer, e.g., the growth or metastasis of cancer cells, and an inflammatory disease, e.g., rheumatoid arthritis, osteoarthritis, hepatitis, bronchial asthma, fibrosis, diabetes mellitus, arteriosclerosis, multiple sclerosis, granuloma, an inflammatory bowel disease (ulcerative colitis and Crohn's disease), an autoimmune disease, and the like.

The pharmaceutical composition comprising the humanized antibody of the present invention can also be used to treat chronic rejection after organ transplantation, and an autoimmune disease such as systemic autoimmune disease, erythematosus, uveitis, Behcet's disease, polymyositis, glomerular proliferative nephritis, sarcoidosis, disease conditions induced by $\alpha 9$ integrin, and the like.

The preventive and/or therapeutic agent for preventing or treating the disorders or diseases described above, comprising the humanized antibody of the present invention, has low toxicity and can be administered to humans orally or parenterally, directly as a liquid preparation by mixing in a suitable solvent, or as a pharmaceutical composition in an appropriate dosage form.

The pharmaceutical composition used for the administration described above contains the aforesaid antibody or salts thereof and pharmaceutically acceptable carriers, diluents or excipients. Such a composition is provided in a dosage form suitable for oral or parenteral administration.

The dose may vary depending upon the age and the size of a subject to be administered, target disease, conditions, route of administration, and the like. When the antibody is used for preventing and/or treating, for example, rheumatoid arthritis in an adult patient, it is advantageous to intravenously administer the antibody of the present invention normally at a single dose of about 0.01 to about 20 mg/kg body weight, preferably about 0.1 to about 10 mg/kg body weight, and more preferably about 0.1 to about 5 mg/kg body weight, approximately 1 to 5 times per day, preferably approximately 1 to 3 times per day. In other parenteral administration and oral administration, the antibody can be administered in a dose corresponding to the dose given above. When the condition is especially severe, the dose may be increased according to the condition.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu and Wu, 1987, J. Biol. Chem. 262:4429 4432). Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, by means of nasal spray, or by means of an implant, said implant being of a porous, non porous, or gelatinous material, including membranes, such as sialastic membranes, or fibers. In one embodiment, administration can be by direct injection at the site (or former site) infected tissues.

In another embodiment, the pharmaceutical composition can be delivered in a vesicle, in particular a liposome (see Langer, 1990, Science 249:1527-1533; Treat et al., in Liposomes in the Therapy of Infectious Disease and Cancer, Lopez Berestein and Fidler (eds.), Liss, New York, pp. 353-365 (1989); Lopez-Berestein, ibid., pp. 317-327; see generally ibid.).

In yet another embodiment, the pharmaceutical composition can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; and Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the composition's target, thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

Examples of the composition for oral administration include solid or liquid dosage forms, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or an excipient conventionally used in the field of pharmaceutical preparations. Examples of the vehicle or excipient for tablets are lactose, starch, sucrose, magnesium stearate, and the like.

The injectable preparations may include dosage forms for intravenous, subcutaneous, intracutaneous and intramuscular injections, drip infusions, etc. These injectable preparations may be prepared by methods publicly known. The injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule. The suppository used for rectal administration may be prepared by blending the aforesaid antibody or its salt with conventional bases for suppositories.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to 500 mg per dosage form in a unit dose; especially in the form of injection, it is preferred that the aforesaid antibody is contained in about 5 to 100 mg and in about 10 to 250 mg for the other dosage forms.

Each composition described above may further contain other active components unless formulation causes any adverse interaction with the antibodies described above.

The present invention also relates to an inhibitor and/or promoter for cell and/or tissue remodeling, which comprises an α9 integrin-binding functional molecule (e.g., OPN, VCAM-1, tenascin-C, fibronectin, pp-vWF, tTG, etc.) as an active ingredient; and a method for inhibiting and/or promoting cell and/or tissue remodeling, which comprises contacting the α9 integrin-expressing cell and/or tissue (e.g., a tumor cell, neutrophil, smooth muscle, etc.) with the α9 integrin-binding functional molecule. The dose, method for administration, pharmaceutical preparation, etc. of the active ingredient in such a therapeutic agent can be appropriately determined by referring to the foregoing description of medicaments comprising the humanized antibodies of the present invention.

As described above, the present invention further provides a method for preventing or treating a disorder or disease that is associated with or involves α9 integrin, said method comprising administering an effective amount of at least one of the humanized antibodies of the present invention to a subject in need thereof.

5.5. Diagnostic Uses

The pharmaceutical composition comprising the humanized antibody of the present invention can be used as a diagnostic agent for cancer, e.g., the growth or metastasis of cancer cells, and an inflammatory disease, e.g., rheumatoid arthritis, osteoarthritis, hepatitis, bronchial asthma, fibrosis, diabetes mellitus, cancer metastasis, arteriosclerosis, multiple sclerosis, granuloma, etc., or as a diagnostic agent for chronic rejection after organ transplantation, an autoimmune disease such as systemic autoimmune disease, erythematosus, uveitis, Behcet's disease, polymyositis, glomerular proliferative nephritis, sarcoidosis, disease conditions induced by α9 integrin, and so forth. The humanized antibodies of the present invention are capable of specifically recognizing the α9 integrin and hence can be used to quantify the α9 integrin in a test fluid, especially for quantification by the sandwich immunoassay, competitive assay, immunometry, nephrometry, etc., immunostaining, or the like. In applying these immunological methods to the assay methods of the present invention, it is not required to set forth any particular conditions, procedures, etc. It is sufficient to construct assay systems by adding ordinary technical consideration in the art to conventional conditions and procedures. For details of these general technical means, reference can be made to reviews, texts or the like.

As described above, the α9 integrin can be quantified with high sensitivity by using the antibodies of the present invention. The humanized antibodies of the present inventions are particularly useful for diagnosing various diseases associated with the α9 integrin by applying the method for quantifying the α9 integrin in vivo. For instance, where an increase or decrease in the expression level of the α9 integrin is detected, it can be diagnosed that it is highly likely that one now suffers from diseases associated with the α9 integrin, e.g., cancer or an inflammatory disease, or it is highly likely that one will suffer from these diseases in the future. Thus, the present invention also provides a method for diagnosing a disorder or disease associated with or involve α9 integrin in a subject, said method comprising administering an effective amount of at least one of the humanized antibodies of the present invention or both to a subject in need thereof. Required dosages for such an in vivo diagnosis may be less than those required for therapeutic uses and can be determined by one skilled in the art according to routine procedures.

The humanized antibodies of the present invention can also be used for specifically detecting the α9 integrin present in a test fluid such as a body fluid, a tissue, etc. The humanized antibodies can also be used for preparation of antibody columns for purification of the α9 integrin, for detection of the α9 integrin contained in each fraction upon purification or for analysis of behaviors of the α9 integrin in cells to be tested.

6. EXAMPLES

The following examples illustrate the preparation of monoclonal antibodies that immunospecifically recognize human and/or mouse α9 integrin, the sequencing of the variable regions of the monoclonal antibodies and other characterization of the antibodies and the chimerization and the humanization of such antibodies, as well as the characterization of the resulting chimeric and humanized antibodies. These examples should not be construed as limiting.

6.1. Preparation of Mouse Antibody Against Human α9 Integrin

Mouse monoclonal antibodies against human α9 integrin were prepared according to the subtractive immunization method (by Williams C. V., et al., 1992, *Biotechniques* 12:842-847). Briefly, three Balb/c mice were injected intraperitoneally with NIH-3T3 cells expressing human α9 integrin (Human α9/NIH-3T3 cells) at $3 \times 10^6$ per mouse. At one and two weeks after the injection, the mice were injected intraperitoneally with $3 \times 10^6$ cells/mouse of Human α9/NIH-3T3 cells, followed by another intravenous injection of the same cells at 2×10⁶ cell/mouse one week later. Hybridomas were prepared by the methods well known in the art (see, for example, Harlow et al., Antibodies: A Laboratory Manual, (Cold Spring Harbor Laboratory Press, 2nd ed. 1988); Hammerling, et al., in: Monoclonal Antibodies and T-Cell Hybridomas, pp. 563-681 (Elsevier, N.Y., 1981). Hybridoma clones producing monoclonal antibodies that were immunospecifically reactive with Human α9/CHO-K1 cells expressing human α9 integrin and with human melanoma cells endogenously expressing human α9 integrin but not with CHO K1 cells expressing human α4 integrin were established and a hybridoma clone (i.e., K33N) producing monoclonal antibody immunospecifically recognizing human α9 integrin were isolated.

6.2. CDR Analysis of Anti-Human α9 Integrin Antibody

The amino acid sequences of CDRs of the monoclonal antibody (i.e., K33N) were determined by reverse transcription of the mRNA extracted from the corresponding hybridoma to prepare cDNAs. Using the cDNAs as templates, the variable regions of the H-chains and L-chains were extended and amplified by PCR using ScFv-cloning primers (Light Primer Mix and Heavy Primer Mix; by Amersham Biosciences Corp., IL). The PCR products were cloned into pCRII TOPO vector, sequenced and the amino acid sequences were determined. This process was repeated three times. The results are shown in Table 1.

TABLE 1

| CDRs | Amino Acid Sequence | SEQ ID NO: |
|---|---|---|
| CDRH1 | SYYMN | 4 |
| CDRH2 | WIFPGSGNTKYNEKFKG | 5 |
| CDRH3 | SWVSYERGYYFDY | 6 |
| CDRL1 | RASENIYYSLA | 11 |
| CDRL2 | NANSLED | 12 |
| CDRL3 | KQAYDVPYT | 13 |

6.3. Cell Adhesion Inhibitory Activity (1) Since it is known that cell adhesion involves the binding of α9 integrin to its ligands, i.e., various ECMs, including OPN, fibronectin, Tenascin-C, VCAM-1, and the like, the isolated anti-human α9 integrin antibody was examined for its cell adhesion inhibitory activity by using of binding of cells expressing human α9 integrin (human melanoma G361 cells) to ligands.

Briefly, OPN peptide was prepared as a bovine serum albumin (BSA)-fusion SVVYGLR (SEQ ID NO:2) peptide. TN-C fn3 (RAA) is prepared as the third region of Fibronectin Type I10 repeat in human Tenascin-C in which the GRD sequences of the peptides have been replaced with the RAA sequence by expressing in E. coli host cells.

OPN peptide and Tenascin-C fragment (TN-C fn3 (RAA)) were added to a 96-well plate at 5 μg/mL and incubated at 37° C. for 1 hour to coat the plate and then the plate was blocked with a blocking solution (0.5% BSA/PBS). The human melanoma G361 cells were suspended in 0.25% BSA/DMEM (1×10⁵ cells/mL) and each concentration of anti human α9 integrin antibodies were added to the cell suspension. The mixture of human melanoma G361 cells (1×10⁵ cells/mL) and the antibodies in 0.25% BSA/DMEM was added to the 96-well plate at 200 μL/well and incubated at 37° C. for 1 hour under 5% CO₂. Non-adherent cells were rinsed off with PBS and adherent cells were fixed and stained with 0.5% Crystal Violet (by WAKO, Osaka, Japan)/20% methanol. The stained cells were washed with distilled water three times and then 20% acetic acid solution was added thereto to effect dissolution. The adhesion activity was quantified by measuring OD at 590 nm wavelength. Anti-human OPN monoclonal antibody (5A1) as negative control and prebiously prepared anti-human α9 integrin antibodies (1K11, 21C5, 24I11, 25B6 and 28S1) as positive control were used.

Figure 1:
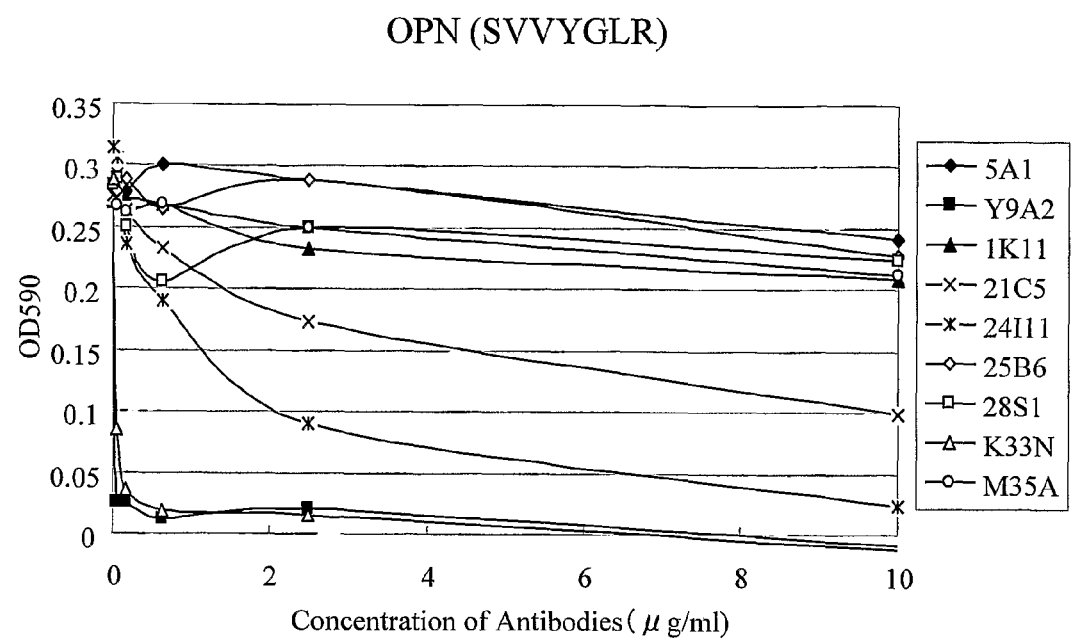
Figure 2:
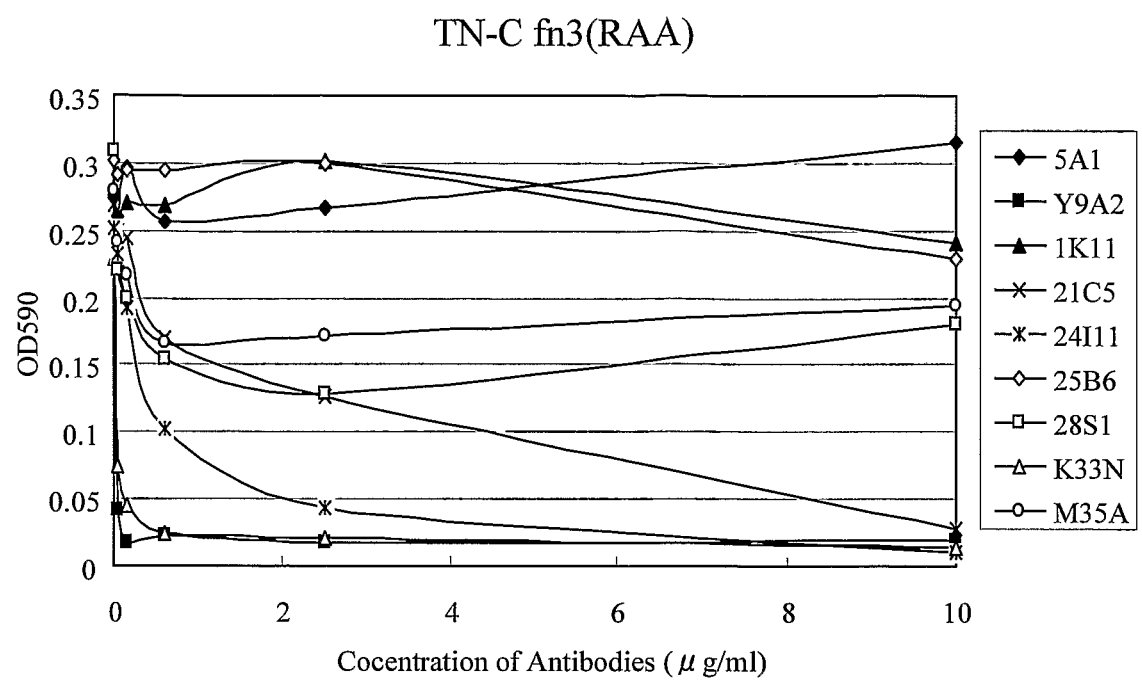

Effect of anti human α9 integrin antibodies to the binding of G361 cells to OPN peptides is shown in FIG. 1, and to Tenascin-C fragment is shown in FIG. 2. As shown in FIG. 1, the cell adhesion involving OPN was inhibited by K33N at low concentration as compared with positive controls 21C5 and 24I11 and at the same concentration of Y9A2. The cell adhesion involving Tenascin-C was inhibited by K33N at low concentration, and, the same as Y9A2, the inhibitory effect was markedly stronger than the positive controls 21C5 and 24I11.

6.4. Humanization of Non-Human Antibodies 6.4.1. Cloning and Sequencing of Mouse K33N V Genes Mouse K33N hybridoma cells were grown in TIL Media I (Immuno-Biological Laboratories, Gunma, Japan) containing 10% fetal bovine serum (FBS; HyClone, Logan, Utah) at 37° C. in a 7.5% CO₂ incubator. Total RNA was extracted from approximately 10⁷ hybridoma cells using TRIzol® reagent (Invitrogen, Carlsbad, Calif.) according to the supplier's protocol. Oligo dT-primed cDNA was synthesized using the GeneRacer™ Kit (Invitrogen) following the supplier's protocol. The variable region cDNAs for K33N heavy and light chains were amplified by polymerase chain reaction (PCR) with Phusion® DNA polymerase (New England Biolabs, Beverly, Mass.) using 3' primers that anneal respectively to the mouse gamma-1 and kappa chain constant regions, and a GeneRacer™ 5' primer (5'-CGACTGGAG-CACGAGGACACTGA-3') (SEQ ID NO:51) provided in the GeneRacer™ Kit. For PCR amplification of heavy chain variable region (VH), the 3' primer has the sequence 5'-GC-CAGTGGATAGACAGATGG-3'(SEQ ID NO:52). For PCR amplification of light chain variable region (VL), the 3' primer has the sequence 5'-GATGGATACAGTTGGTG-CAGC-3'(SEQ ID NO:53). The amplified VH and VL cDNAs were subcloned into the pCR4Blunt-TOPO vector (Invitrogen) for sequence determination. DNA sequencing of the variable regions was carried out at Tocore (Menlo Park, Calif.). Several heavy and light chain clones were sequenced and unique sequences homologous to typical mouse heavy and light chain variable regions were identified. The consensus cDNA sequences along with deduced amino acid sequences of K33N VH and VL are shown in FIGS. 3 and 4, respectively.

6.4.2. Construction of Chimeric K33N IgG1/κ Antibody

Figure 7:
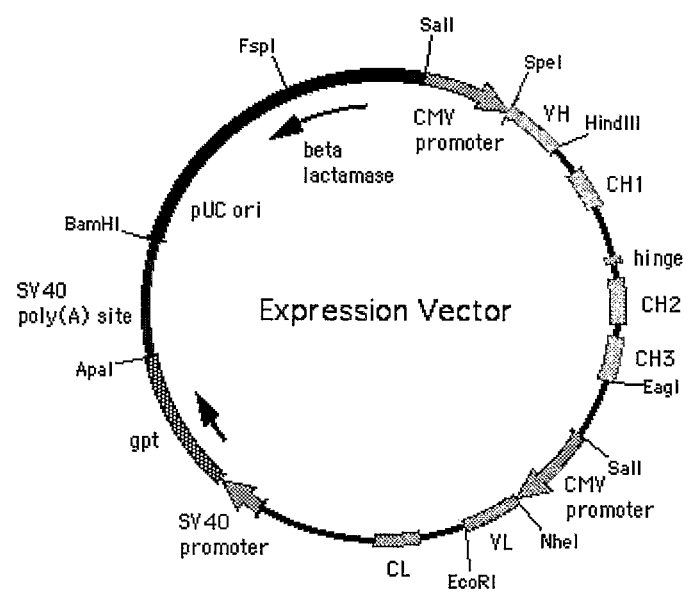

A gene encoding K33N VH was generated as an exon including a splice donor signal and appropriate flanking restriction enzyme sites by PCR using K33N VH cDNA as a template, 5'-GGG ACTAGTACCACCATGGGATGGAGCTGGATCTTTC TC-3'(SpeI site is underlined) (SEQ ID NO:40) as a 5' primer, and 5'-GGG AAGCTTGTTTTAAGGACTCACCTGAGGAGACTCTG AGACTGGTGCC-3' (SEQ ID NO:41) (HindIII site is underlined) as a 3' primer (FIG. 5). Likewise, a gene encoding K33N VL was generated as an exon including a splice donor signal and appropriate flanking restriction enzyme sites by PCR using K33N VL cDNA as a template, 5'-GGG GCTAGCACCACCATGAGTGTGCCCACTCAACTCC TG-3' (SEQ ID NO:42) (NheI site is underlined) as a 5' primer, and 5'-GGG GAATTCTGAGAAGACTACTTACGTTTTATTTCCAGC TTGGTCCCCCC-3' (SEQ ID NO:43) (EcoRI site is underlined) as a 3' primer (FIG. 6). The splice donor signals of the K33N VH and VL exons were derived from the mouse germline JH4 and Jκ2 sequences, respectively. PCR-amplified fragments were gel-purified using QIAquick Gel Extraction Kit (Qiagen, Valencia, Calif.), digested with SpeI and HindIII (for VH) or NheI and EcoRI (for VL), and cloned into a mammalian expression vector carrying human gamma-1 and kappa constant regions for production of chimeric K33N IgG1/κ antibody. The schematic structure of the resulting expression vector, pChK33N, is shown in FIG. 7.

6.4.3. Generation of Humanized K33N V Genes

Humanization of the K33N variable regions was carried out as outlined by Queen et al. (Proc. Natl. Acad. Sci. USA 86: 10029-10033, 1989). First, a molecular model of the K33N variable regions was constructed with the aid of computer programs. Next, based on a homology search against human variable region sequences, the human amino acid sequence derived from DA980102 (accession number), which has a high homology to K33N VH, was chosen as an acceptor to provide the frameworks for humanized K33N VH. The amino acid identity in the frameworks between the mouse K33N and DA980102 VH regions is 74.7% (65/87) Likewise, the human amino acid sequence of X72441 (GenBank™ accession number) was chosen as an acceptor for humanization of K33N VL. The amino acid identity in the frameworks between the mouse K33N and X72441 VL regions is 76.3% (61/80).

At framework positions where the computer model suggested significant contact with the complementarity determining regions (CDRs), the amino acids from the K33N variable regions were substituted for the human framework amino acids. This was done at positions 28, 48, 66, 67 and 71 to generate humanized K33N (HuK33N) VH (FIG. 8). In addition, Met at position 82 of the human DA980102 acceptor was found be atypical in the same subgroup of human VH sequences and therefore replaced by the most common amino acid residue (Leu) to reduce potential immunogenicity. For the light chain, replacements were made at residues 70 and 71 to generate HuK33N VL (FIG. 9). The alignments of K33N, designed HuK33N, and the human acceptor amino acid sequence are shown for VH in FIG. 8 and for VL in FIG. 9.

A gene encoding each of HuK33N VH and VL was designed as an exon including a signal peptide, a splice donor signal, and appropriate restriction enzyme sites for subsequent cloning into a mammalian expression vector. The splice donor signals of the HuK33N VH and VL exons were derived from the human germline JH4 and Jκ1 sequences, respectively. The signal peptide sequence of the mouse K33N VH gene was indicated to be suboptimal for precise cleavage by the SIG-Pred signal peptide prediction software (http://bmbpcu36.leeds.ac.uk/prot_analysis/Signal.html). Therefore, the signal peptide sequence of the VH gene of the mouse anti-human α9 integrin monoclonal antibody 24I11 (Gene Techno Science), which was predicted to be cleaved efficiently and precisely by the SIG-Pred software, was used in the HuK33N VH gene. The signal peptide sequence in the humanized K33N VL exon was derived from the corresponding mouse K33N VL sequence. The SIG-Pred software indicated that the signal peptide of the HuK33N VL gene is cleaved efficiently and precisely.

The HuK33N VH and VL genes were constructed by extension and PCR amplification of several overlapping synthetic oligonucleotide primers using ThermalAce DNA polymerase (Invitrogen) as outlined by He et al. (J. Immunol. 160: 1029-1035, 1998). The oligonucleotides used for construction of HuK33N VH and VL genes are listed in FIGS. 10 and 11, respectively. The location of the oligonucleotides in the HuK33N VH and VL genes is shown in FIGS. 12 and 13, respectively.

PCR-amplified fragments were gel-purified using QIAquick Gel Extraction Kit (Qiagen) and cloned into pCR4Blunt-TOPO vector for sequence determination. After digestion with SpeI and HindIII (for VH) or NheI and EcoRI (for VL), HuK33N VH and VL genes were subcloned into corresponding sites in a mammalian expression vector for production in the human IgG1/κ form. The schematic structure of the resulting expression vector, pHuK33N, is shown in FIG. 7. The nucleotide sequences of the obtained HuK33N VH and VL genes along with deduced amino acid sequences are shown in FIGS. 14 and 15, respectively.

6.4.4. Transient Expression of Chimeric and Humanized K33N IgG1/κ

Chimeric and humanized K33N IgG1/κ antibodies were transiently expressed by transfecting pChK33N and pHuK33N plasmid DNA, respectively, to HEK293 cells using polyethylenimine according to Durocher et al. (Nucl. Acids Res. 30: e9, 2002). Transiently transfected HEK293 cells were maintained for four days in DMEM containing 10% FBS at 37° C. in a 7.5% $CO_2$ incubator. The expression level of each of ChK33N and HuK33N IgG1/κ antibodies in culture supernatant was measured by sandwich ELISA. An ELISA plate was coated overnight at 4° C. with 100 μl/well of 1/2,000-diluted goat anti-human IgG Fcγ-chain-specific polyclonal antibodies (SouthernBiotech, Birmingham, Ala.) in PBS, washed with Wash Buffer (PBS containing 0.05% Tween 20), and blocked for 1 hr at room temperature with 300 μl/well of Blocking Buffer (PBS containing 2% Skim Milk and 0.05% Tween 20). After washing with Wash Buffer, 100 μl/well of samples appropriately diluted in ELISA Buffer (PBS containing 1% Skim Milk and 0.025% Tween 20) were applied to the ELISA plate. Human IgG1/κ antibody purified from human myeloma serum (SouthernBiotech) was used as a standard. After incubating the ELISA plate for 2 hr at room temperature and washing with Wash Buffer, bound antibodies were detected using 100 μl/well of 1/2,000-diluted HRP-conjugated goat anti-human kappa chain polyclonal antibodies (SouthernBiotech). After incubating for 1 hr at room temperature and washing with Wash Buffer, color development was performed by adding 100 μl/well of ABTS substrate (bio-WORLD, Dublin, Ohio). Color development was stopped by adding 100 μl/well of 2% oxalic acid. Absorbance was read at 405 nm.

Binding of transiently expressed ChK33N and HuK33N antibodies to human α9 integrin was examined by cell ELISA. CHO-K1 stable transfectants expressing recombinant human α9 integrin on the surface (CHO/huα9; provided by Gene Techno Science) were seeded at 2×10⁵ cells/well in 50 μl of F12/DMEM (HyClone) containing 10% FBS in a 96-well tissue culture plate and grown overnight at 37° C. in a 7.5% $CO_2$ incubator. For testing of binding to human α9 integrin, 50 μl of ChK33N, HuK33N or irrelevant human IgG1/κ myeloma antibody (SouthernBiotech) in F12/DMEM containing 10% FBS was added to each well. After incubating for 1 hr at 4° C. and washing cells twice with ice-cold PBS, 100 μl of 1/1,000-diluted HRP-conjugated goat anti-human IgG polyclonal antibodies (SouthernBiotech) was added to each well. After incubating for 1 hr at 4° C., cells were washed three times with ice-cold PBS. For color development, 100 μl of ABTS substrate was added. Color development was stopped by adding 100 μl of 2% oxalic acid. Absorbance was read at 405 nm. The result showed that the binding of ChK33N antibody to human α9 integrin was almost same as that of HuK33N antibody at both 0.5 and 1 μg/ml (FIG. 16).

6.4.5. Generation of NS0 Stable Transfectants Producing Each of ChK33N and HuK33N IgG1/κ Antibodies To obtain cell lines stably producing ChK33N and HuK33N IgG1/κ antibodies, the expression vectors pChK33N and pHuK33N, respectively, were introduced into the chromosome of a mouse myeloma cell line NS0 (European Collection of Animal Cell Cultures, Salisbury, Wiltshire, UK). NS0 cells were grown in DME medium containing 10% FBS at 37° C. in a 7.5% $CO_2$ incubator. Stable transfection into NS0 was carried out by electroporation as described in Bebbington et al. (Bio/Technology 10: 169-175, 1992). Before transfection, expression vector was linearized using FspI. Approximately $10^7$ cells were transfected with 10 μg of linearized plasmid, suspended in DME medium containing 10% FBS, and plated into several 96-well plates. After 24 hr, selection media (DME medium containing 10% FBS, HT media supplement (Sigma, St. Louis, Mo.), 0.25 mg/ml xanthine and 1 μg/ml mycophenolic acid) was applied. Approximately 10 days after the initiation of selection, culture supernatants were assayed for antibody production.

Expression of ChK33N and HuK33N IgG1/κ antibodies was measured by sandwich ELISA essentially according to the procedure described in Section 6.4.3. An NS0 stable transfectant producing a high level of ChK33N antibody (NS0-ChK33N 3D11) was adapted to growth in serum-free media using Hybridoma SFM (Invitrogen). An NS0 stable transfectant producing a high level of HuK33N antibody was further subcloned in a 96-well plate by limiting dilution. One of the subclones (NS0-HuK33N 8G8-11) was adapted to growth in Hybridoma-SFM. Testing with the PCR Mycoplasma Detection Set (Takara Bio USA, Madison, Wis.) indicated that both NS0-ChK33N 3D11 and NS0-HuK33N 8G8-11 were negative for the presence of mycoplasma.

The authenticity of HuK33N heavy and light chains produced in NS0-HuK33N 6D5-11 was confirmed by cDNA sequencing. Total RNA was extracted from NS0-HuK33N 6D5-11 cells using TRIzol® reagent (Invitrogen) and oligo dT-primed cDNA was synthesized using the GeneRacer™ Kit (Invitrogen) following suppliers' protocols. The coding region of gamma-1 heavy chain was amplified by PCR using CMV2 and JNT098 as primers (FIG. 17) and Phusion® polymerase (New England Biolabs). PCR fragments were gel-purified and subjected to sequencing with CMV2, JNT082, JNT097 and JNT098 as primers (FIG. 17). Similarly, the coding region of kappa light chain was amplified using CMV2 and JNT026 (FIG. 17). Gel-purified DNA fragments were subjected to sequencing with CMV2, JNT026, JNT080 and JNT084 as primers (FIG. 17). The obtained nucleotide sequence of the coding region for each of HuK33N heavy and light chains matched perfectly with the corresponding sequence in the pHuK33N vector (FIGS. 18 and 19, respectively).

6.4.6. Purification and ChK33N and HuK33N Antibodies

NS0-ChK33N 3D11 and NS0-HuK33N 8G8-11 cells were grown to exhaustion in Hybridoma-SFM in roller bottles. After centrifugation and filtration, culture supernatant was loaded onto a protein-A Sepharose column (GE Healthcare, Piscataway, N.J.). The column was washed with PBS before the antibody was eluted with 0.1 M glycine-HCl (pH 3.0). After neutralization with 1 M Tris-HCl (pH 8), the buffer of eluted antibody was changed to PBS by dialysis. Antibody concentration was determined by measuring absorbance at 280 nm (1 mg/ml=1.4 OD). The antibody expression level was 50 μg/ml for NS0-ChK33N 3D11 cells and 12 μg/ml for NS0-HuK33N 8G8-11 cells.

Purified ChK33N and HuK33N antibodies were characterized by SDS-PAGE according to standard procedures. Analysis under reducing conditions indicated that each of ChK33N and HuK33N antibodies is comprised of a heavy chain with a molecular weight of about 50 kDa and a light chain with a molecular weight of about 25 kDa (FIG. 20). The purity of each antibody appeared to be more than 95%.

6.4.7. Characterization of ChK33N and HuK33N Antibodies

Binding of mouse, chimeric and humanized K33N antibodies to human α9 integrin was examined in a FACS™ binding assay with CHO/huα9 cells. Approximately $5 \times 10^5$ CHO/huα9 cells/test were washed with FACS™ Binding Buffer (PBS containing 0.5% BSA and 0.05% $NaN_3$) and suspended in 200 μl of FACS™ Binding Buffer containing various amounts of test antibody. After 30 min on ice, the cells were washed with FACS™ Binding Buffer. The cells stained with mouse K33N were then suspended in 100 μl of 1/200-diluted FITC-labeled goat anti-mouse IgG polyclonal antibody (SouthernBiotech) in FACS™ Binding Buffer. The cells stained with chimeric or humanized K33N were suspended in 100 μl of 1/200-diluted FITC-labeled goat anti-human IgG polyclonal antibody (SouthernBiotech) in FACS FACS™ Binding Buffer. After 30 min on ice, the cells were washed with FACS™ Binding Buffer, suspended in 200 μl of FACS™ Binding Buffer, and analyzed using a FACScan™ flow cytometer (BD Biosciences, Franklin Lakes, N.J.). The EC50 value of mouse K33N antibody for binding to CHO/huα9 cells was 104 ng/ml (FIG. 21). Between ChK33N and HuK33N antibodies, the binding pattern was very similar to each other (FIG. 22). In addition, the $EC_{50}$ values of ChK33N and HuK33N antibodies were nearly identical to each other (143 ng/ml for ChK33N antibody and 151 ng/ml for HuK33N antibody). This result indicates that mouse K33N antibody was successfully humanized without losing the antigen binding affinity.

6.4.8. Cell Adhesion Assay 96-well flat-bottomed microtiter plates (Nunc) were coated with 50 μL of 5 μg/mL hTNC (AEIDGIEL)-BSA solution for 1 hour at 37° C. in $CO_2$ incubator. Control wells were coated with 50 μL of 5 μg/mL BSA solution. After coating reaction, solution in wells were replaced with 200 μL of 0.5 w/v % BSA (blocking) solution and incubated for 1 hour at room temperature. After blocking reaction, wells were washed with PBS. 150 μL of $2.5 \times 10^5$ cells/mL G-361 cells suspended in TIL media containing 0.25 w/v % BSA and 50 μL of test antibody solution (0.25 w/v % BSA/TIL) were plated in the wells and incubated for 1 hour in a $CO_2$ incubator at 37° C. After incubation, each well was carefully washed three times with PBS solution in order to remove the non-adherent cells. 50 μL of 0.5 w/v % Crystal Violet solution was added to fix and stain the adherent cells. Thirty minutes later, excess dye was removed by washing with tub of water three times, and dye in the wells were solubilized with 50 μL of 20 v/v % acetic acid. The absorbance of each well at 595 nm was measured using absorption spectrometer. Cell adhesion inhibition rate was calculated by the formula as follows; $(1-(A-B)/(C-B)) \times 100(\%)$. A: Absorbance of the wells coated with hTNC-BSA in the presence of antibodies, B: Absorbance of the wells coated with BSA in the absence of any test antibodies, C: Absorbance of the wells coated with hTNC-BSA in the presence of Normal human IgG (negative control) (FIG. 23).

Results $IC_{50}$ of Y9A2 was 0.053 μg/ml (95% CI: 0.032-0.089). $IC_{50}$ of K33N, ChK33N and HuK33N were 0.075 μM (0.053-0.106), 0.090 μg/ml (0.063-0.128), 0.084 μg/ml (0.055-

0.129), respectively, indicating $IC_{50}$ values of test antibodies were as on the same level as that of Y9A2.

7. DEPOSITION

The hybridomas designated herein as K33N producing mouse anti-human α9 integrin monoclonal antibodies were deposited on May 29, 2007 with International Patent Organisms Depository, National Institute of Advanced Industrial Science and Technology, located at Central 6, 1-1-1 Higashi, Tsukuba, Ibaraki (postal code: 305-8566) in accordance with the Budapest Treaty on the Deposit of Microorganisms, and accorded Accession Nos. FERM BP-10830 which is incorporated herein by reference in their entireties.

8. INDUSTRIAL APPLICABILITY

The humanized monoclonal antibodies of the present invention inhibit the function of α9 integrin to exhibit therapeutic effects on cancer, e.g., the growth or metastasis of cancer cells, and an inflammatory disease, e.g., rheumatoid arthritis, osteoarthritis, hepatitis, bronchial asthma, fibrosis, diabetes mellitus, cancer metastasis, arteriosclerosis, multiple sclerosis, granuloma, an inflammatory bowel disease (ulcerative colitis and Crohn's disease), an autoimmune disease, and the like.

9. LIST OF SEQUENCES

The sequences referenced throughout the specification are summarized below.

| SEQ ID NO. | TYPE | DESCRIPTION | SEQUENCE |
|---|---|---|---|
| 1 | AA | OPN adhesion sequence | GRGDS |
| 2 | AA | HuOPN's α4β1/α9β1-binding site | SVVYGLR |
| 3 | AA | MuOPN's α4β1/α9β1-binding site | SLAYGLR |
| 4 | AA | CDRH1 of K33N (FERM BP-10830) | SYYMN |
| 5 | AA | CDRH2 of K33N (FERM BP-10830) | WIFPGSGNTKYNEKFKG |
| 6 | AA | CDRH3 of K33N (FERM BP-10830) | SWVSYERGYYFDY |
| 7 | DNA | VH of K33N (FERM BP-10830) including sequence encoding signal peptide (1-57) FIG. 3 | ATGGGATGGAGCTGGATCTTTCTCTTCCTC CTGTCAGGAACTGCAGGTGTCCATTGCCAG GTCCAACTGCAGCAGTCTGGACCTGAGCTG GTGAAGCCTGGGGCTTCAGTGAAGATATCC TGCAAGGCTTCTGGCTACAGCTTTACAAGT TACTATATGAATTGGGTGAAGAAGAGGCCT GGACAGGGACTTGAGTGGATTGGTTGGATC TTTCCTGGAAGTGGTAATACTAAGTACAAT GAGAAGTTCAAGGGCAAGGCCACACTGACG GCAGACACATCCTCCAGTACAGCCTACATG CAGGTCAGCAGCCTGACATCTGAGGACTCT GCAGTCTATTTCTGTGCAAGATCGTGGGTT AGCTACGAGAGGGGGTATTATTTTGACTAC TGGGGTCAAGGCACCAGTCTCACAGTCTCC TCA |
| 8 | AA | VH of K33N (FERM BP-10830) including signal peptide (1-19) FIG. 3 | MGWSWIFLFLLSGTAGVHCQVQLQQSGPEL VKPGASVKISCKASGYSFTSYYMNWVKKRP GQGLEWIGWIFPGSGNTKYNEKFKGKATLT ADTSSSTAYMQVSSLTSEDSAVYFCARSWV SYERGYYFDYWGQGTSLTVSS |
| 9 | AA | Mature VH of K33N (FERM BP-10830) | QVQLQQSGPELVKPGASVKISCKASGYSFT SYYMNWVKKRPGQGLEWIGWIFPGSGNTKY NEKFKGKATLTADTSSSTAYMQVSSLTSED SAVYFCARSWVSYERGYYFDYWGQGTSLTV SS |
| 10 | AA | Signal peptide of K33N H-chain | MGWSWIFLFLLSGTAGVHC |
| 11 | AA | CDRL1 of K33N (FERM BP-10830) | RASENIYYSLA |
| 12 | AA | CDRL2 of K33N (FERM BP-10830) | NANSLED |
| 13 | AA | CDRL3 of K33N (FERM BP-10830) | KQAYDVPYT |
| 14 | DNA | VL of K33N (FERM BP-10830) including sequence encoding signal peptide (1-60) FIG. 4 | ATGAGTGTGCCCACTCAACTCCTGGGGTTG CTGCTGCTGTGGCTTACAGACGCAGGATGT GACATCCAGATGACTCAGTCTCCAGCCTCC CTGGCTGCATCTGTGGGAGAAACTGTCACC CTCACATGTCGAGCAAGTGAGAACATTTAC TACAGTTTAGCATGGTATCAGCAGAAGCAA GGGAAATCTCCTCAGCTCCTGATCTATAAT GCAAACAGCTTGGAAGATGGTGTCCCATCG TAGGTCAGTGGCAGTGGATCTGGGACACAG TATTCTATGAAGATCAACAGCATGCAGCCT GAAGATACCGCAACTTATTTCTGTAAACAG AAGCAAGCTTATGACGTTCCGTACACGTTCGGAGGG GGGACCAAGCTGGAAATAAAA |
| 15 | AA | VL of K33N (FERM BP-10830) including signal peptide (1-20) FIG. 4 | MSVPTQLLGLLLLWLTDAGCDIQMTQSPAS LAASVGETVTLTCRASENIYYSLAWYQQKQ GKSPQLLIYNANSLEDGVPSRFSGSGSGTQ YSMKINSMQPEDTATYFCKQAYDVPYTFGG GTKLEIK |
| 16 | AA | Mature VL of K33N (FERM BP-10830) | DIQMTQSPASLAASVGETVTLTCRASENIY YSLAWYQQKQGKSPQLLIYNANSLEDGVPS RFSGSGSGTQYSMKINSMQPEDTATYFCKQ AYDVPYTFGGGTKLEIK |
| 17 | AA | Signal peptide of K33N L-chain | MSVPTQLLGLLLLWLTDAGC |
| 18 | DNA | DA980102 | AACCACATCCCTCCTCAGAAGCCCCCAGAG CACAACTCCTTACCATGGACTGGACCTGGA GGATCCTCTTTTTGGTGGCAGCAGCCACAG GTGCCCACTCCCAGGTCCAGCTTGTGCAGT CTGGGGCTGAGGTGAAGAAGCCTGGGGCCT CAGTGAAGGTTTCCTGCAAGGCTTCTGGAT ACACCTTCACTAACTATGCTCTGCATTGGG TGCGCCAGGCCCCCGGACAAAGGCTTGAGT |

| SEQ ID NO. | TYPE | DESCRIPTION | SEQUENCE |
|---|---|---|---|
| | | | GGATGGGATGGATCAACACTGGCAATGGTA ACACAAAATATTCACAGAAGTTCCAGGGCA GAGTCACCCTTACCAGTGACACATCCGCGA GCACAGCCTACATGGAGATGAGCAGCCTGA GATCTGAAGACACGGCTGTGTATTACTGTG CGAGGAGCAGTGGCTGGTACGTTTGGTTCG ACCCCTGGGGCCAGGGAACCCTGGTCACCG TCTCCTCAGCTTCCACCAAGGGCCCATCGG TTTTCCCCCTGGCGCCCTGCTCCAGGAGCA CCTCTGGGGGCACAGCGGCCCTGGGCTGCC TGGTCAAGGACTACTTCCCCGAA |
| 19 | AA | FRH1 of DA980102 | QVQLVQSGAEVKKPGASVKVSCKASGYTFT |
| 20 | AA | FRH2 of DA980102 | WVRQAPGQRLEWMG |
| 21 | AA | FRH3 of DA980102 | RVTLTSDTSASTAYMEMSSLRSEDTAVYYC AR |
| 22 | AA | FRH4 of DA980102 | WGQGTLV TVSS |
| 23 | DNA | X72441 | CGCTCAGCTCCTGGGGCTCCTGCTACTCTG GCTCCGAGGTGCCAGATGTGACATCCAGAT GACCCAGTCTCCATCCTCCCTGTCTGCATC TGTAGGAGACAGAGTCACCATCACTTGCCG GGCAAGTCAGAGCATTAGCAGCTATTTAAA TTGGTATCAGCAGAAACCAGGGAAAGCCCC TAAGCTCCTGATCTATGCTGCATCCAGTTT GCAAAGTGGGGTCCCATCAAGGTTCAGTGG CAGTGGATCTGGGACAGATTTCACTCTCAC CATCAGCAGTCTGCAACCTGAAGATTTTGC AACTTACTACTGTCAACAGAGTTACAGTAC CCCTCGGACGTTCGGCCAAGGGACCAAGGT GGAAATCAAA |
| 24 | AA | FRL1 of X72441 | DIQMTQSPSSLSASVGDRVTITC |
| 25 | AA | FRL2 of X72441 | WYQQKPGKAPKLLIY |
| 26 | AA | FRL3 of X72441 | GVPSRFSGSGSGTDFTLTISSLQPEDFATY YC |
| 27 | AA | FRL4 of X72441 | FGQGTKVEIK |
| 28 | DNA | VH of HuK33N including signal peptide (16-72) FIG. 12 | GGGACTAGTACCACCATGAAATGCAGCTGG GTTATCTTCTTCCTGATGGCAGTGGTTACA GGGTGCAATTCACAGGTCCAACTGGTGCAG TCTGGAGCTGAGGTTAAGAAGCCTGGGGCT TCAGTGAAGGTTTCCTGCAAGGCTTCTGGC TACAGCTTTACAAGTTACTATATGAATTGG GTGCGCCAGGCCCCTGGACAGAGGCTTGAG TGGATTGGTTGGATCTTTCCTGGAAGTGGT AATACTAAGTACAATGAAGTTCAAGGGC AAGGCCACACTGACGGCAGACACATCCGCG AGCACAGCCTACATGGAGCTCAGCAGCCTG AGATCTGAGGACACTGCCGTCTATTACTGT GCAAGATCGTGGGTTAGCTACGAGAGGGGG TATTATTTTGACTACTGGGGTCAAGGAACC CTGGTCACCGTCTCCTCAGGTGAGTCCTCA CAAAAGCTTCCC |
| 29 | AA | VH of HuK33N including signal peptide (1-19) FIG. 12 | *MKCSWVIFFLMAVVTGVNS*QVQLVQSGAEV KKPGASVKVSCKASGYSFT<u>SYYMN</u>WVRQAP GQRLEWIG<u>WIFPGSGNTKYNEKFKG</u>KATLT ADTSASTAYMELSSLRSEDTAVYYCAR<u>SWV SYERGYYFDY</u>WGQGTLVTVSS |
| 30 | DNA | VL of HuK33N including signal peptide (16-75) FIG. 13 | GGGGCTAGCACCACCATGAGTGTGCCCACT CAACTCCTGGGGTTGCTGCTGCTGTGGCTT ACAGAGCGACGATGTGACATCCAGATGACT CAGTCTCCATCCTCCCTGTCTGCATCTGTG GGAGACAGAGTCACCATCACATGTCGAGCA AGTGAGAACATTTACTACGTTTAGCATGG TATCAGCAGAAGCCAGGGAAAGCCCCTAAG CTCCTGATCTATAATGCAAACAGCTTGGAA GATGGTGTCCCATCGAGGTTCAGTGGCAGT GGATCTGGGACACAGTATACTCTCACCATC AGCAGCCTGCAGCCTGAAGATTTTGCAACT TATTACTGTAAACAGGCTTATGACGTTCCG TACACGTTCGGACAAGGGACCAAGGTGGAA ATCAAACGTGAGTAGAATTTAAAGAATTCC CC |
| 31 | AA | VL of HuK33N including signal peptide (1-20) FIG. 13 | *MSVPTQLLGLLLLWLTDARC*DIQMTQSPSS LSASVGDRVTITC<u>RASENIYYSLA</u>WYQQKP GKAPKLLIY<u>NANSLED</u>GVPSRFSGSGSGTQ YTLTISSLQPEDFATYYC<u>KQAYDVPYT</u>FGQ GTKVEIK |
| 32 | DNA | ChK33N VH gene flanked by SpeI and HindIII sites including sequence encoding signal peptide (1-57), flanked by SpeI and HindIII sites FIG. 5 | <u>ACTAGT</u>ACCACCATGGGATGGAGCTGGATC TTTCTCTTCCTCCTGTCAGGAACTGCAGGT GTCCATTGCCAGGTCCAACTGCAGCAGTCT GGACCTGAGCTGGTGAAGCCTGGGGCTTCA GTGAAGATATCCTGCAAGGCTTCTGGCTAC AGCTTTACAAGTTACTATATGAATTGGGTG AAGAAGAGGCCTGGACAGGGACTTGAGTGG ATTGGTTGGATCTTTCCTGGAAGTGGTAAT ACTAAGTACAATGAAGTTCAAGGGCAAG GCCACACTGACGGCAGACACATCCTCCAGT ACAGCCTACATGCAGGTCAGCAGCCTGACA TCTGAGGACTCTGCAGTCTATTTCTGTGCA AGTCGTGGGTTAGCTACGAGAGGGGGTAT TATTTTGACTACTGGGGTCAAGGCACCAGT CTCACAGTCTCCTCAG<i>GTGAGTCCTTAAAA</i><u>CAAGCTT</u> |
| 33 | DNA | ChK33N VL gene flanked by NheI and EcoRI sites including sequence encoding signal peptide (1-60), flanked by NheI and EcoRI sites FIG. 6 | <u>GCTAGC</u>ACCACCATGAGTGTGCCCACTCAA CTCCTGGGGTTGCTGCTGCTGTGGCTTACA GACGCAGGATGTGACATCCAGATGACTCAG TCTCCAGCCTCCCTGGCTGCATCTGTGGGA GAAACTGTCACCCTCACATGTCGAGCAAGT GAGAACATTTACAGTTTAGCATGGTAT CAGCAGAAGCAAGGGAAATCTCCTCAGCTC CTGATCTATAATGCAAACAGCTTGGAAGAT GGTGTCCCATCGAGGTTCAGTGGCAGTGGA TCTGGGACACAGTATTCTATGAAGATCAAC AGCATGCAGCCTGAAGATACCGCAACTTAT TTCTGTAAACAGGCTTATGACGTTCCGTAC ACGTTCGGAGGGGGGACCAAGCTGGAAATA AAACGTAAGTAGTCTTCTCA<u>GAATTC</u> |
| 34 | DNA | HuK33N VH gene flanked by SpeI and HindIII sites FIG. 14 | <u>ACTAGT</u>ACCACCATGAAATGCAGCTGGGTT ATCTTCTTCCTGATGGCAGTGGTTACAGGG TCAATTCACGGTCCAACTGGTGCAGTCT GGAGCTGAGGTTAAGAAGCCTGGGGCTTCA GTGAAGGTTTCCTGCAAGGCTTCTGGCTAC AGCTTTACAAGTTACTATATGAATTGGGTG CGCCAGGCCCCTGGACAGAGGCTTGAGTGG ATTGGTTGGATCTTTCCTGGAAGTGGTAAT ACTAAGTACAATGAAGTTCAAGGGCAAG GCCACACTGACGGCAGACACATCCGCGAGT ACAGCCTACATGGAGCTCAGCAGCCTGAGA TCTGAGGACACTGCCGTCTATTACTGTGCA AGATCGTGGGTTAGCTACGAGAGGGGGTAT TATTTTGACTACTGGGGTCAAGGAACCCTG GTCACCGTCTCCTCAG<i>GTGAGTCCTCACAA</i><u>AAGCTT</u> |
| 35 | DNA | HuK33N VL gene flanked | <u>GCTAGC</u>ACCACCATGAGTGTGCCCACTCAA CTCCTGGGGTTGCTGCTGCTGTGGCTTACA |

| SEQ ID NO. | TYPE | DESCRIPTION | SEQUENCE |
|---|---|---|---|
| | | by NheI and EcoRI sites FIG. 15 | GACGCACGATGTGACATCCAGATGACTCAG TCTCCATCCTCCCTGTCTGCATCTGTGGGA GACAGAGTCACCATCACATGTCGAGCAAGT GAGAACATTTACTACAGTTTAGCATGGTAT CAGCAGAAGCCAGGGAAAGCCCCTAAGCTC CTGATCTATAATGCAAACAGCTTGGAAGAT GGTGTCCCATCGAGGTTCAGTGGCAGTGGA TCTGGGACACAGTATACTCTCACCATCAGC AGCCTGCAGCCTGAAGATTTTGCAACTTAT TACTGTAAACAGGCTTATGACGTTCCGTAC ACGTTCGGACAAGGGACCAAGGTGGAAATC AAACGTGAGTAGAATTTAAA<u>GAATTC</u> |
| 36 | DNA | HuK33N gamma-1 heavy chain in pHuK33N FIG. 18 | ATGAAATGCAGCTGGGTTATCTTCTTCCTG ATGGCAGTGGTTACAGGGGTCAATTCACAG GTCCAACTGGTGCAGTCTGGAGCTGAGGTT AAGAAGCCTGGGGCTTCAGTGAAGGTTTCC TGCAAGGCTTCTGGCTACAGCTTTACAAGT TACTATATGAATTGGGTGCGCCAGGCCCCT GGACAGAGGCTTGAGTGGATTGGTTGGATC TTTCCTGGAAGTGGTAATACTAAGTACAAT GAGAAGTTCAAGGGCAAGGCCACACTGACG GCAGATACATCCGCCAGTACAGCCTACATG GAGCTCAGCAGCCTGAGATCTGAGGACACT GCCGTCTATTACTGTGCAAGATCGTGGGTT AGCTACGAGAGGGGGTATTATTTTGACTAC TGGGGTCAAGGAACCCTGGTCACCGTCTCC TCAGCCTCCACCAAGGGCCCATCGGTCTTC CCCCTGGCACCCTCCTCCAAGAGCACCTCT GGGGGCACAGCGGCCCTGGGCTGCCTGGTC AAGGACTACTTCCCCGAACCGGTGACGGTG TCGTGGAACTCAGGCGCCCTGACCAGCGGC GTGCACACCTTCCCGGCTGTCCTACAGTCC TCAGGACTCTACTCCCTCAGCAGCGTGGTG ACCGTGCCCTCCAGCAGCTTGGGCACCCAG ACCTACATCTGCAACGTGAATCACAAGCCC AGCAACACCAAGGTGGACAAGAAAGTTGAG CCCAAATCTTGTGACAAAACTCACACATGC CCACCGTGCCCAGCACCTGAACTCCTGGGG GGACCGTCAGTCTTCCTCTTCCCCCCAAAA CCCAAGGACACCCTCATGATCTCCCGGACC CCTGAGGTCACATGCGTGGTGGTGGACGTG AGCCACGAAGACCCTGAGGTCAAGTTCAAC TGGTACGTGGACGGCGTGGAGGTGCATAAT GCCAAGACAAAGCCGCGGGAGGAGCAGTAC AACAGCACGTACCGTGTGGTCAGCGTCCTC ACCGTCCTGCACCAGGACTGGCTGAATGGC AAGGAGTACAAGTGCAAGGTCTCCAACAAA GCCCTCCCAGCCCCCATCGAGAAAACCATC TCCAAAGCCAAAGGGCAGCCCCGAGAACCA CAGGTGTACACCCTGCCCCCATCCCGGGAT GAGCTGACCAAGAACCAGGTCAGCCTGACC TGCCTGGTCAAAGGCTTCTATCCCAGCGAC ATCGCCGTGGAGTGGGAGAGCAATGGGCAG CCGGAGAACAACTACAAGACCACGCCTCCC GTGCTGGACTCCGACGGCTCCTTCTTCCTC TACAGCAAGCTCACCGTGGACAAGAGCAGG TGGCAGCAGGGGAACGTCTTCTCATGCTCC GTGATGCATGAGGCTCTGCACAACCACTAC ACGCAGAAGAGCCTCTCCCTGTCTCCGGGT AAATGA |
| 37 | AA | HuK33N gamma-1 heavy chain FIG. 18 | MKCSWVIFFLMAVVTGVNSQVQLVQSGAEV KKPGASVKVSCKASGYSFTSYYMNWVRQAP GQRLEWIGWIFPGSGNTKYNEKFKGKATLT ADTSASTAYMELSSLRSEDTAVYYCARSWV SYERGYYFDYWGQGTLVTVSSASTKGPSVF PLAPSSKSTSGGTAALGCLVKDYFPEPVTV SWNSGALTSGVHTFPAVLQSSGLYSLSSVV TVPSSSLGTQTYICNVNHKPSNTKVDKKVE PKSCDKTHTCPPCPAPELLGGPSVFLFPPK PKDTLMISRTPEVTCVVVDVSHEDPEVKFN WYVDGVEVHNAKTKPREEQYNSTYRVVSVL TVLHQDWLNGKEYKCKVSNKALPAPIEKTI SKAKGQPREPQVYTLPPSRDELTKNQVSLT CLVKGFYPSDIAVEWESNGQPENNYKTTPP VLDSDGSFFLYSKLTVDKSRWQQGNVFSCS VMHEALHNHYTQKSLSLSPGK |
| 38 | DNA | HuK33N kappa light chain in pHuK33N FIG. 19 | ATGAGTGTGCCCACTCAACTCCTGGGGTTG CTGCTGCTGTGGCTTACAGACGCACGATGT GACATCCAGATGACTCAGTCTCCATCCTCC CTGTCTGCATCTGTGGGAGACAGAGTCACC ATCACATGTCGAGCAAGTGAGAACATTTAC TACAGTTTAGCATGGTATCAGCAGAAGCCA GGGAAAGCCCCTAAGCTCCTGATCTATAAT GCAAACAGCTTGGAAGATGGTGTCCCATCG AGGTTCAGTGGCAGTGGATCTGGGACACAG TATACTCTCACCATCAGCAGCCTGCAGCCT GAAGATTTTGCAACTTATTACTGTAAACAG GCTTATGACGTTCCGTACACGTTCGGACAA GGGACCAAGGTGGAAATCAAACGAACTGTG GCTGCACCATCTGTCTTCATCTTCCCGCCA TCTGATGAGCAGTTGAAATCTGGAACTGCC TCTGTTGTGTGCCTGCTGAATAACTTCTAT CCCAGAGAGGCCAAAGTACAGTGGAAGGTG GATAACGCCCTCCAATCGGGTAACTCCCAG GAGAGTGTCACAGAGCAGGACAGCAAGGAC AGCACCTACAGCCTCAGCAGCACCCTGACG CTGAGCAAAGCAGACTACGAGAAACACAAA GTCTACGCCTGCGAAGTCACCCATCAGGGC CTGAGCTCGCCCGTCACAAAGAGCTTCAAC AGGGGAGAGTGTTAG |
| 39 | AA | HuK33N kappa light chain FIG. 19 | MSVPTQLLGLLLLWLTDARCDIQMTQSPSS LSASVGDRVTITCRASENIYYSLAWYQQKP GKAPKLLIYNANSLEDGVPSRFSGSGSGTQ YTLTISSLQPEDFATYYCKQAYDVPYTFGQ GTKVEIKRTVAAPSVFIFPPSDEQLKSGTA SVVCLLNNFYPREAKVQWKVDNALQSGNSQ ESVTEQDSKDSTYSLSSTLTLSKADYEKHK VYACEVTHQGLSSPVTKSFNRGEC |
| 40 | DNA | 5' primer for K33N VH with SpeI site | GGG<u>ACTAGT</u>ACCACCATGGGATGGAGCTGG ATCTTTCTC |
| 41 | DNA | 3' primer for K33N VH with HindIII site | GGG<u>AAGCTT</u>GTTTTAAGGACTCACCTGAGG AGACTCTGAGACTGGTGCC |
| 42 | DNA | 5' primer for K33N VL with NheI site | GGGG<u>CTAGC</u>ACCACCATGAGTGTGCCCACT CCAACTCTG |
| 43 | DNA | 3' primer for K33N VL with EcoRI site | GGGG<u>AATTC</u>TGAGAAGACTACTTACGTTTT ATTTCCAGCTTGGTCCCCCC |
| 44 | DNA | CMV2 | GAACCGTCAGATCGCCTGGAGACG |
| 45 | DNA | JNT026 | TGAAAGATGAGCTGGAGGAC |
| 46 | DNA | JNT080 | GAACTGTGGCTGCACCATC |
| 47 | DNA | JNT082 | CTTTCTTGTCCACCTTGGTG |
| 48 | DNA | JNT084 | GTTGAAGCTCTTTGTGACGG |
| 49 | DNA | JNT097 | GCTGTCCTACAGTCCTCAG |
| 50 | DNA | JNT098 | ACGTGCCAAGCATCCTCG |
| 51 | DNA | GeneRacer™ 5'primer | CGACTGGAGCACGAGGACACTGA |
| 52 | DNA | 3' primer for PCR | GCCAGTGGATAGACAGATGG |

| SEQ ID NO. | TYPE | DESCRIPTION | SEQUENCE |
|---|---|---|---|
| | | amplification of heavy chain variable region (VH) | |
| 53 | DNA | 3' primer for PCR amplification of light chain variable region (VL) | GATGGATACAGTTGGTGCAGC |
| 54 | AA | Tenascin-C 33-35 | AEIDGIEL |
| 55 | AA | Human α9 integrin (signal peptide; 1-29 residues; in italic) | *MGGPAAPRGAGRLRALLLALVVAGIPAGAY* NLDPQRPVHFQGPADSFFGYAVLEHFHDNT RWVLVGAPKADSKYSPSVKSPGAVFKCRVH TNPDRRCTELDMARGKNRGTSCGKTCREDR DDEWMGVSLARQPKADGRVLACAHRWKNIY YEADHILPHGFCYIIPSNLQAKGRTLIPCY EEYKKKYGEEHGSCQAGIAGFFTEELVVMG APGSFYWAGTIKVLNLTDNTYLKLNDEVIM NRRYTYLGYAVTAGHFSHPSTIDVVGGAPQ DKGIGKVYIFRADRRSGTLIKIFQASGKKM VGSYFGSSLCAVDLNGDGLSDLLGAPMFSE IRDEGQVTVYINRGNGALEEQLALTGDGAY NAHFGESIASLDDLDNDGFPDVAIGAPKED DFAGAVYIYHGDAGGIVPQYSMKLSGQKIN PVLRMFGQSISGGIDMDGNGYPDVTVGAFM SDSVVLLRARPVITVDVSIFLPGSINITAP QCHDGQQPVNCLNVTTCFSFHGKHVPGEIG LNYVLMADVAKKEKGQMPRVYFVLLGETMG QVTEKLQLTYMEETCRHYVAHVKRRVQDVI SPIVFEAAYSLSEHVTGEEERELPPLTPVL RWKKGQKIAQKNQTVFERNCRSEDCAADLQ LQGKLLLSSMDEKTLYLALGAVKNISLNIS FISNLGDDAYDANVSFNVSRELFINMWQKE EMGISCELLESDFLKCSVGFPFMRSKSKYE FSVIFDTSHLSGEEEVLSPIVTAQSGNTER SESLHDNTLVLMVPLMHEVDTSITGIMSPT SFVYGESVDAANFIQLDDLECHFQPINITL QVYNTGPSTLPGSSVSISFPNRLSSGGAEM FHVQEMVVGQEKGNCSFQKNPTPCIIPQEQ ENIFHTIFAFFTKSGRKVLDCEKPGISCLT FAHCNSALAKEESRTIDIYMLLNTEILKKD SSSVIQFMSRAKVKVDPALRVVEIAHGNPE EVTVVFEALHNLEPRGYVVGWITAISLLVG ILIFLLLAVLLWKMGFFRRRYKEHEAEKNR KENEDSWDWVQKNQ |
| 56 | DNA | 5' RACE primer | GCCAGTGGATAGACTGATGG |
| 57 | DNA | 5' RACE primer | GATGGATACAGTTGGTGCAGC |
| 58 | AA | Signal peptide of HuK33N H-chain | *MKCSWVIFFLMAVVTGVNS* |
| 59 | AA | Signal peptide of HuK33N L-chain | *MSVPTQLLGLLLLWLTDARC* |
| 60 | AA | Mature VH of HuK33N | QVQLVQSGAEVKKPGASVKVSCKASGYSFT SYYMNWVRQAPGQRLEWIG<u>WIFPGSGNTKY NEKFKG</u>KATLTADTSASTAYMELSSLRSED TAVYYCAR<u>SWVSYERGYYFDY</u>WGQGTLVTV SS |
| 61 | AA | Mature VL of HuK33N | DIQMTQSPSSLSASVGDRVTITC<u>RASENIY YSLA</u>WYQQKPGKAPKLLIY<u>NANSLED</u>GVPS RFSGSGSGTQYTLTISSLQPEDFATYYC<u>KQ AYDVPYT</u>FGQGTKVEIK |
| 62 | DNA | HuK33N VH gene | CAGGTCCAACTGGTGCAGTCTGGAGCTGAG GTTAAGAAGCCTGGGGCTTCAGTGAAGGTT TCCTGCAAGGCTTCTGGCTACAGCTTTACA AGTTACTATATGAATTGGGTGCGCCAGGCC CCTGGACAGAGGCTTGAGTGGATTGGTTGG ATCTTTCCTGGAAGTGGTAATACTAAGTAC AATGAGAAGTTCAAGGGCAAGGCCACACTG ACGGCAGACACATCCGCCAGTACAGCCTAC ATGGAGCTCAGCAGCCTGAGATCTGAGGAC ACTGCCGTCTATTACTGTGCAAGATCGTGG GTTAGCTACGAGAGGGGGTATTATTTTGAC TACTGGGGTCAAGGAACCCTGGTCACCGTC TCCTCA |
| 63 | DNA | HuK33N VL gene | GACATCCAGATGACTCAGTCTCCATCCTCC CTGTCTGCATCTGTGGGAGACAGAGTCACC ATCACATGTCGAGCAAGTGAGAACATTTAC TACAGTTTAGCATGGTATCAGCAGAAGCCA GGGAAAGCCCCTAAGCTCCTGATCTATAAT GCAAACAGCTTGGAAGATGGTGTCCCATCG AGGTTCAGTGGCAGTGGATCTGGGACACAG TATACTCTCACCATCAGCAGCCTGCAGCCT GAAGATTTTGCAACTTATTACTGTAAACAG GCTTATGACGTTCCGTACACGTTCGGACAA GGGACCAAGGTGGAAATCAAA |

The invention claimed is:

1. A humanized antibody or an antigen-binding fragment thereof that immunospecifically recognizes human α9 integrin, comprising an H-chain that comprises the amino acid sequence of SEQ ID NO:60 and an L-chain that comprises the amino acid sequence of SEQ ID NO:61.

2. A pharmaceutical composition comprising the humanized antibody or an antigen-binding fragment thereof of claim 1, and a pharmaceutically acceptable carrier.

* * * * *

UNITED STATES PATENT AND TRADEMARK OFFICE
CERTIFICATE OF CORRECTION

PATENT NO.          : 8,735,552 B2
APPLICATION NO.     : 13/201847
DATED               : May 27, 2014
INVENTOR(S)         : Shankar Kumar et al.

It is certified that error appears in the above-identified patent and that said Letters Patent is hereby corrected as shown below:

On the title page, item (73) the following Assignees information should be deleted:

"(73)    Assignees:    Gene Techno Science Co., Ltd.,
                       Hokkaido (JP); Kaken Pharmaceutical
                       Co., Tokyo (JP)"

On the title page, item (73) the following Assignees information should be inserted:

-- (73)  Assignees:    Gene Techno Science Co., Ltd.,
                       Hokkaido (JP); Kaken Pharmaceutical
                       Co., Ltd., Tokyo (JP) --

Signed and Sealed this
Twenty-third Day of December, 2014

Michelle K. Lee
*Deputy Director of the United States Patent and Trademark Office*

SEQUENCE LISTING

<160> NUMBER OF SEQ ID NOS: 64

<210> SEQ ID NO 1
<211> LENGTH: 5
<212> TYPE: PRT
<213> ORGANISM: Unknown
<220> FEATURE:
<223> OTHER INFORMATION: OPN adhesion sequence

<400> SEQUENCE: 1

Gly Arg Gly Asp Ser

<210> SEQ ID NO 2
<211> LENGTH: 7
<212> TYPE: PRT
<213> ORGANISM: Homo sapiens

<400> SEQUENCE: 2

Ser Val Val Tyr Gly Leu Arg
1               5

<210> SEQ ID NO 3
<211> LENGTH: 7
<212> TYPE: PRT
<213> ORGANISM: Mus musculus

<400> SEQUENCE: 3

Ser Leu Ala Tyr Gly Leu Arg
1               5

<210> SEQ ID NO 4
<211> LENGTH: 5
<212> TYPE: PRT
<213> ORGANISM: Mus musculus

<400> SEQUENCE: 4

Ser Tyr Tyr Met Asn
1               5

<210> SEQ ID NO 5
<211> LENGTH: 17
<212> TYPE: PRT
<213> ORGANISM: Mus musculus

<400> SEQUENCE: 5

Trp Ile Phe Pro Gly Ser Gly Asn Thr Lys Tyr Asn Glu Lys Phe Lys
1               5                   10                  15

Gly

<210> SEQ ID NO 6
<211> LENGTH: 13
<212> TYPE: PRT
<213> ORGANISM: Mus musculus

<400> SEQUENCE: 6

Ser Trp Val Ser Tyr Glu Arg Gly Tyr Tyr Phe Asp Tyr
1               5                   10

<210> SEQ ID NO 7
<211> LENGTH: 423
<212> TYPE: DNA
<213> ORGANISM: Mus musculus

<400> SEQUENCE: 7
atgggatgga gctggatctt tctcttcctc ctgtcaggaa ctgcaggtgt ccattgccag      60
gtccaactgc agcagtctgg acctgagctg gtgaagcctg ggcttcagt gaagatatcc     120 tgcaaggctt ctggctacag ctttacaagt tactatatga attgggtgaa gaagaggcct     180 ggacaggac ttgagtggat tggttggatc tttcctggaa gtggtaatac taagtacaat     240
gagaagttca aggcaaggc cacactgacg gcagacacat cctccagtac agcctacatg     300
caggtcagca gcctgacatc tgaggactct gcagtctatt tctgtgcaag atcgtgggtt     360
agctacgaga gggggtatta ttttgactac tggggtcaag gcaccagtct cacagtctcc     420
tca                                                                 423

<210> SEQ ID NO 8
<211> LENGTH: 141
<212> TYPE: PRT
<213> ORGANISM: Mus musculus

<400> SEQUENCE: 8

Met Gly Trp Ser Trp Ile Phe Leu Phe Leu Leu Ser Gly Thr Ala Gly
1               5                   10                  15

Val His Cys Gln Val Gln Leu Gln Gln Ser Gly Pro Glu Leu Val Lys
            20                  25                  30

Pro Gly Ala Ser Val Lys Ile Ser Cys Lys Ala Ser Gly Tyr Ser Phe
        35                  40                  45

Thr Ser Tyr Tyr Met Asn Trp Val Lys Lys Arg Pro Gly Gln Gly Leu
    50                  55                  60

Glu Trp Ile Gly Trp Ile Phe Pro Gly Ser Gly Asn Thr Lys Tyr Asn
65                  70                  75                  80

Glu Lys Phe Lys Gly Lys Ala Thr Leu Thr Ala Asp Thr Ser Ser Ser
                85                  90                  95

Thr Ala Tyr Met Gln Val Ser Ser Leu Thr Ser Glu Asp Ser Ala Val
            100                 105                 110

Tyr Phe Cys Ala Arg Ser Trp Val Ser Tyr Glu Arg Gly Tyr Tyr Phe
        115                 120                 125

Asp Tyr Trp Gly Gln Gly Thr Ser Leu Thr Val Ser Ser
    130                 135                 140

<210> SEQ ID NO 9
<211> LENGTH: 122
<212> TYPE: PRT
<213> ORGANISM: Mus musculus

<400> SEQUENCE: 9

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
            20                  25                  30

Tyr Met Asn Trp Val Lys Lys Arg Pro Gly Gln Gly Leu Glu Trp Ile
        35                  40                  45

Gly Trp Ile Phe Pro Gly Ser Gly Asn Thr Lys Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Val Ser Ser Leu Thr Ser Glu Asp Ser Ala Val Tyr Phe Cys
                85                  90                  95

Ala Arg Ser Trp Val Ser Tyr Glu Arg Gly Tyr Tyr Phe Asp Tyr Trp
            100                 105                 110

Gly Gln Gly Thr Ser Leu Thr Val Ser Ser
        115                 120

<210> SEQ ID NO 10
<211> LENGTH: 19
<212> TYPE: PRT
<213> ORGANISM: Mus musculus

<400> SEQUENCE: 10

Met Gly Trp Ser Trp Ile Phe Leu Phe Leu Leu Ser Gly Thr Ala Gly
1               5                   10                  15

Val His Cys

<210> SEQ ID NO 11
<211> LENGTH: 11
<212> TYPE: PRT
<213> ORGANISM: Mus musculus

<400> SEQUENCE: 11

Arg Ala Ser Glu Asn Ile Tyr Tyr Ser Leu Ala
1               5                   10

<210> SEQ ID NO 12
<211> LENGTH: 7
<212> TYPE: PRT
<213> ORGANISM: Mus musculus

<400> SEQUENCE: 12

Asn Ala Asn Ser Leu Glu Asp
1               5

<210> SEQ ID NO 13
<211> LENGTH: 9
<212> TYPE: PRT
<213> ORGANISM: Mus musculus

<400> SEQUENCE: 13

Lys Gln Ala Tyr Asp Val Pro Tyr Thr
1               5

<210> SEQ ID NO 14
<211> LENGTH: 381
<212> TYPE: DNA
<213> ORGANISM: Mus musculus

<400> SEQUENCE: 14

```
atgagtgtgc ccactcaact cctggggttg ctgctgctgt ggcttacaga cgcaggatgt    60
gacatccaga tgactcagtc tccagcctcc ctggctgcat ctgtgggaga aactgtcacc   120
ctcacatgtc gagcaagtga gaacatttac tacagtttag catggtatca gcagaagcaa   180
gggaaatctc ctcagctcct gatctataat gcaaacagct tggaagatgg tgtcccatcg   240
aggttcagtg gcagtggatc tgggacacag tattctatga agatcaacag catgcagcct   300
gaagataccg caacttattt ctgtaaacag gcttatgacg ttccgtacac gttcggaggg   360
gggaccaagc tggaaataaa a                                              381
```

<210> SEQ ID NO 15
<211> LENGTH: 127
<212> TYPE: PRT
<213> ORGANISM: Mus musculus

<400> SEQUENCE: 15

Met Ser Val Pro Thr Gln Leu Leu Gly Leu Leu Leu Leu Trp Leu Thr
1               5                   10                  15

Asp Ala Gly Cys Asp Ile Gln Met Thr Gln Ser Pro Ala Ser Leu Ala
            20                  25                  30

Ala Ser Val Gly Glu Thr Val Thr Leu Thr Cys Arg Ala Ser Glu Asn
        35                  40                  45

Ile Tyr Tyr Ser Leu Ala Trp Tyr Gln Gln Lys Gln Gly Lys Ser Pro
    50                  55                  60

Gln Leu Leu Ile Tyr Asn Ala Asn Ser Leu Glu Asp Gly Val Pro Ser
65                  70                  75                  80

```
Arg Phe Ser Gly Ser Gly Ser Gly Thr Gln Tyr Ser Met Lys Ile Asn
                85                  90                  95

Ser Met Gln Pro Glu Asp Thr Ala Thr Tyr Phe Cys Lys Gln Ala Tyr
            100                 105                 110

Asp Val Pro Tyr Thr Phe Gly Gly Gly Thr Lys Leu Glu Ile Lys
        115                 120                 125

<210> SEQ ID NO 16
<211> LENGTH: 107
<212> TYPE: PRT
<213> ORGANISM: Mus musculus

<400> SEQUENCE: 16

Asp Ile Gln Met Thr Gln Ser Pro Ala Ser Leu Ala Ala Ser Val Gly
1               5                   10                  15

Glu Thr Val Thr Leu Thr Cys Arg Ala Ser Glu Asn Ile Tyr Tyr Ser
            20                  25                  30

Leu Ala Trp Tyr Gln Gln Lys Gln Gly Lys Ser Pro Gln Leu Leu Ile
        35                  40                  45

Tyr Asn Ala Asn Ser Leu Glu Asp Gly Val Pro Ser Arg Phe Ser Gly
    50                  55                  60

Ser Gly Ser Gly Thr Gln Tyr Ser Met Lys Ile Asn Ser Met Gln Pro
65                  70                  75                  80

Glu Asp Thr Ala Thr Tyr Phe Cys Lys Gln Ala Tyr Asp Val Pro Tyr
                85                  90                  95

Thr Phe Gly Gly Gly Thr Lys Leu Glu Ile Lys
            100                 105

<210> SEQ ID NO 17
<211> LENGTH: 20
<212> TYPE: PRT
<213> ORGANISM: Mus musculus

<400> SEQUENCE: 17

Met Ser Val Pro Thr Gln Leu Leu Gly Leu Leu Leu Leu Trp Leu Thr
1               5                   10                  15

Asp Ala Gly Cys
            20

<210> SEQ ID NO 18
<211> LENGTH: 563
<212> TYPE: DNA
<213> ORGANISM: Homo sapiens

<400> SEQUENCE: 18
aaccacatcc ctcctcagaa gccccagag cacaactcct taccatggac tggacctgga    60
ggatcctctt tttggtggca gcagccacag gtgcccactc ccaggtccag cttgtgcagt   120
ctggggctga ggtgaagaag cctggggcct cagtgaaggt ttcctgcaag gcttctggat   180
acaccttcac taactatgct ctgcattggg tgcgccaggc ccccggacaa aggcttgagt   240
ggatgggatg gatcaacact ggcaatggta acacaaaata ttcacagaag ttccagggca   300
gagtcaccct taccagtgac acatccgcga gcacagccta catggagatg agcagcctga   360
gatctgaaga cacggctgtg tattactgtg cgaggagcag tggctggtac gtttggttcg   420
accctggggg ccagggaacc ctggtcaccg tctcctcagc ttccaccaag ggcccatcgg   480
tcttccccct ggcgccctgc tccaggagca cctctggggg cacagcggcc ctgggctgcc   540
tggtcaagga ctacttcccc gaa                                          563
```

<210> SEQ ID NO 19
<211> LENGTH: 30
<212> TYPE: PRT
<213> ORGANISM: Homo sapiens

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 20
<211> LENGTH: 14
<212> TYPE: PRT
<213> ORGANISM: Homo sapiens

<400> SEQUENCE: 20

Trp Val Arg Gln Ala Pro Gly Gln Arg Leu Glu Trp Met Gly
1               5                   10

<210> SEQ ID NO 21
<211> LENGTH: 32
<212> TYPE: PRT
<213> ORGANISM: Homo sapiens

<400> SEQUENCE: 21

Arg Val Thr Leu Thr Ser Asp Thr Ser Ala Ser Thr Ala Tyr Met Glu
1               5                   10                  15

Met Ser Ser Leu Arg Ser Glu Asp Thr Ala Val Tyr Tyr Cys Ala Arg
            20                  25                  30

<210> SEQ ID NO 22
<211> LENGTH: 11
<212> TYPE: PRT
<213> ORGANISM: Homo sapiens

<400> SEQUENCE: 22

Trp Gly Gln Gly Thr Leu Val Thr Val Ser Ser
1               5                   10

<210> SEQ ID NO 23
<211> LENGTH: 370
<212> TYPE: DNA
<213> ORGANISM: Homo sapiens

<400> SEQUENCE: 23
cgctcagctc ctggggctcc tgctactctg gctccgaggt gccagatgtg acatccagat      60
gacccagtct ccatcctccc tgtctgcatc tgtaggagac agagtcacca tcacttgccg     120
ggcaagtcag agcattagca gctatttaaa ttggtatcag cagaaaccag ggaaagcccc     180
taagctcctg atctatgctg catccagttt gcaaagtggg gtcccatcaa ggttcagtgg     240
cagtggatct gggacagatt tcactctcac catcagcagt ctgcaacctg aagattttgc     300
aacttactac tgtcaacaga gttacagtac ccctcggacg ttcggccaag gaccaaggt     360 ggaaatcaaa                                                            370

<210> SEQ ID NO 24
<211> LENGTH: 23
<212> TYPE: PRT
<213> ORGANISM: Homo sapiens

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 25
<211> LENGTH: 15
<212> TYPE: PRT
<213> ORGANISM: Homo sapiens

<400> SEQUENCE: 25

Trp Tyr Gln Gln Lys Pro Gly Lys Ala Pro Lys Leu Leu Ile Tyr
1               5                   10                  15

<210> SEQ ID NO 26
<211> LENGTH: 32
<212> TYPE: PRT
<213> ORGANISM: Homo sapiens

<400> SEQUENCE: 26

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 27
<211> LENGTH: 10
<212> TYPE: PRT
<213> ORGANISM: Homo sapiens

<400> SEQUENCE: 27

Phe Gly Gln Gly Thr Lys Val Glu Ile Lys
1               5                   10

<210> SEQ ID NO 28
<211> LENGTH: 462
<212> TYPE: DNA
<213> ORGANISM: Unknown
<220> FEATURE:
<223> OTHER INFORMATION: VH of HuK33N including signal peptide

<400> SEQUENCE: 28
gggactagta ccaccatgaa atgcagctgg gttatcttct tcctgatggc agtggttaca      60
ggggtcaatt cacaggtcca actggtgcag tctggagctg aggttaagaa gcctggggct     120
tcagtgaagg tttcctgcaa ggcttctggc tacagcttta caagttacta tatgaattgg     180
gtgcgccagg cccctggaca gaggcttgag tggattggtt ggatctttcc tggaagtggt     240
aatactaagt acaatgagaa gttcaagggc aaggccacac tgacggcaga cacatccgcg     300
agcacagcct acatggagct cagcagcctg agatctgagg acactgccgt ctattactgt     360
gcaagatcgt gggttagcta cgagagggggg tattattttg actactgggg tcaaggaacc     420
ctggtcaccg tctcctcagg tgagtcctca caaaagcttc cc                         462

<210> SEQ ID NO 29
<211> LENGTH: 141
<212> TYPE: PRT
<213> ORGANISM: Unknown
<220> FEATURE:
<223> OTHER INFORMATION: VH of HuK33N including signal peptide

<400> SEQUENCE: 29

Met Lys Cys Ser Trp Val Ile Phe Phe Leu Met Ala Val Val Thr Gly

```
                1               5              10              15
        Val Asn Ser Gln Val Gln Leu Val Gln Ser Gly Ala Glu Val Lys Lys
                        20                  25                  30

Pro Gly Ala Ser Val Lys Val Ser Cys Lys Ala Ser Gly Tyr Ser Phe
                        35                  40                  45

Thr Ser Tyr Tyr Met Asn Trp Val Arg Gln Ala Pro Gly Gln Arg Leu
                        50                  55                  60

Glu Trp Ile Gly Trp Ile Phe Pro Gly Ser Gly Asn Thr Lys Tyr Asn
         65                  70                  75                  80

Glu Lys Phe Lys Gly Lys Ala Thr Leu Thr Ala Asp Thr Ser Ala Ser
                        85                  90                  95

Thr Ala Tyr Met Glu Leu Ser Ser Leu Arg Ser Glu Asp Thr Ala Val
                        100                 105                 110

Tyr Tyr Cys Ala Arg Ser Trp Val Ser Tyr Glu Arg Gly Tyr Tyr Phe
                        115                 120                 125

Asp Tyr Trp Gly Gln Gly Thr Leu Val Thr Val Ser Ser
                        130                 135                 140

<210> SEQ ID NO 30
<211> LENGTH: 422
<212> TYPE: DNA
<213> ORGANISM: Unknown
<220> FEATURE:
<223> OTHER INFORMATION: VL of HuK33N including signal peptide

<400> SEQUENCE: 30
ggggctagca ccaccatgag tgtgcccact caactcctgg ggttgctgct gctgtggctt      60
acagacgcac gatgtgacat ccagatgact cagtctccat cctccctgtc tgcatctgtg     120
ggagacagag tcaccatcac atgtcgagca agtgagaaca tttactacag tttagcatgg     180
tatcagcaga agccagggaa agcccctaag ctcctgatct ataatgcaaa cagcttggaa     240
gatggtgtcc catcgaggtt cagtggcagt ggatctggga cacagtatac tctcaccatc     300
agcagcctgc agcctgaaga ttttgcaact tattactgta aacaggctta tgacgttccg     360
tacacgttcg gacaagggac caaggtggaa atcaaacgtg agtagaattt aaagaattcc     420
cc                                                                    422

<210> SEQ ID NO 31
<211> LENGTH: 127
<212> TYPE: PRT
<213> ORGANISM: Unknown
<220> FEATURE:
<223> OTHER INFORMATION: VL of HuK33N including signal peptide

<400> SEQUENCE: 31

Met Ser Val Pro Thr Gln Leu Leu Gly Leu Leu Leu Leu Trp Leu Thr
          1               5                  10                  15

Asp Ala Arg Cys Asp Ile Gln Met Thr Gln Ser Pro Ser Ser Leu Ser
                        20                  25                  30

Ala Ser Val Gly Asp Arg Val Thr Ile Thr Cys Arg Ala Ser Glu Asn
                        35                  40                  45

Ile Tyr Tyr Ser Leu Ala Trp Tyr Gln Gln Lys Pro Gly Lys Ala Pro
                        50                  55                  60

Lys Leu Leu Ile Tyr Asn Ala Asn Ser Leu Glu Asp Gly Val Pro Ser
         65                  70                  75                  80

Arg Phe Ser Gly Ser Gly Ser Gly Thr Gln Tyr Thr Leu Thr Ile Ser
                        85                  90                  95
```

```
Ser Leu Gln Pro Glu Asp Phe Ala Thr Tyr Tyr Cys Lys Gln Ala Tyr
        100                 105                 110

Asp Val Pro Tyr Thr Phe Gly Gln Gly Thr Lys Val Glu Ile Lys
        115                 120                 125
```

<210> SEQ ID NO 32
<211> LENGTH: 457
<212> TYPE: DNA
<213> ORGANISM: Unknown
<220> FEATURE:
<223> OTHER INFORMATION: ChK33N VH gene flanked by SpeI and HindIII
      sites including sequence encoding signal peptide 1-57, flanked by
      SpeI and HindIII sites

<400> SEQUENCE: 32

```
actagtacca ccatgggatg agctggatc tttctcttcc tcctgtcagg aactgcaggt      60
gtccattgcc aggtccaact gcagcagtct ggacctgagc tggtgaagcc tggggcttca    120
gtgaagatat cctgcaaggc ttctggctac agctttacaa gttactatat gaattgggtg    180
aagaagaggc ctggacaggg acttgagtgg attggttgga tctttcctgg aagtggtaat    240
actaagtaca atgagaagtt caagggcaag gccacactga cggcagacac atcctccagt    300
acagcctaca tgcaggtcag cagcctgaca tctgaggact ctgcagtcta tttctgtgca    360
agatcgtggg ttagctacga gaggggtat tattttgact actggggtca aggcaccagt    420
ctcacagtct cctcaggtga gtccttaaaa caagctt                             457
```

<210> SEQ ID NO 33
<211> LENGTH: 416
<212> TYPE: DNA
<213> ORGANISM: Unknown
<220> FEATURE:
<223> OTHER INFORMATION: ChK33N VL gene flanked by NheI and EcoRI sites
      including sequence encoding signal peptide 1-60, flanked by NheI
      and EcoRI sites

<400> SEQUENCE: 33

```
gctagcacca ccatgagtgt gcccactcaa ctcctggggt tgctgctgct gtggcttaca     60
gacgcaggat gtgacatcca gatgactcag tctccagcct ccctggctgc atctgtggga    120
gaaactgtca ccctcacatg tcgagcaagt gagaacattt actacagttt agcatggtat    180
cagcagaagc aagggaaatc tcctcagctc ctgatctata tgcaaacag cttggaagat    240 ggtgtcccat cgaggttcag tggcagtgga tctgggacac agtattctat gaagatcaac    300
agcatgcagc ctgaagatac cgcaacttat ttctgtaaac aggcttatga cgttccgtac    360
acgttcggag gggggaccaa gctggaaata aaacgtaagt agtcttctca gaattc        416
```

<210> SEQ ID NO 34
<211> LENGTH: 456
<212> TYPE: DNA
<213> ORGANISM: Unknown
<220> FEATURE:
<223> OTHER INFORMATION: HuK33N VH gene flanked by SpeI and HindIII
      sites

<400> SEQUENCE: 34

```
actagtacca ccatgaaatg cagctgggtt atcttcttcc tgatggcagt ggttacaggg     60
gtcaattcac aggtccaact ggtgcagtct ggagctgagg ttaagaagcc tggggcttca    120
gtgaaggttt cctgcaaggc ttctggctac agctttacaa gttactatat gaattgggtg    180
cgccaggccc ctggacagag gcttgagtgg attggttgga tctttcctgg aagtggtaat    240
actaagtaca atgagaagtt caagggcaag gccacactga cggcagacac atccgccagt    300
```

```
acagcctaca tggagctcag cagcctgaga tctgaggaca ctgccgtcta ttactgtgca      360
agatcgtggg ttagctacga gaggggggtat tatttttgact actggggtca aggaaccctg   420
```

```
acagcctaca tggagctcag cagcctgaga tctgaggaca ctgccgtcta ttactgtgca      360
agatcgtggg ttagctacga gaggggtat tattttgact actggggtca aggaaccctg      420
gtcaccgtct cctcaggtga gtcctcacaa aagctt                                456
```

<210> SEQ ID NO 35
<211> LENGTH: 416
<212> TYPE: DNA
<213> ORGANISM: Unknown
<220> FEATURE:
<223> OTHER INFORMATION: HuK33N VL gene flanked by NheI and EcoRI sites

<400> SEQUENCE: 35

```
gctagcacca ccatgagtgt gcccactcaa ctcctggggt tgctgctgct gtggcttaca      60
gacgcacgat gtgacatcca gatgactcag tctccatcct ccctgtctgc atctgtggga    120
gacagagtca ccatcacatg tcgagcaagt gagaacattt actacagttt agcatggtat    180
cagcagaagc cagggaaagc ccctaagctc ctgatctata atgcaaacag cttggaagat    240
ggtgtcccat cgaggttcag tggcagtgga tctgggacac agtatactct caccatcagc    300
agcctgcagc ctgaagattt tgcaacttat tactgtaaac aggcttatga cgttccgtac    360
acgttcggac aagggaccaa ggtggaaatc aaacgtgagt agaatttaaa gaattc        416
```

<210> SEQ ID NO 36
<211> LENGTH: 1416
<212> TYPE: DNA
<213> ORGANISM: Unknown
<220> FEATURE:
<223> OTHER INFORMATION: HuK33N gamma-1 heavy chain in pHuK33N

<400> SEQUENCE: 36

```
atgaaatgca gctgggttat cttcttcctg atggcagtgg ttacagggt caattcacag       60 gtccaactgg tgcagtctgg agctgaggtt aagaagcctg ggcttcagt gaaggtttcc     120 tgcaaggctt ctggctacag cttttacaagt tactatatga attgggtgcg ccaggcccct    180
ggacagaggc ttgagtggat tggttggatc ttttcctggaa gtggtaatac taagtacaat    240
gagaagttca agggcaaggc cacactgacg gcagacacat ccgccagtac agcctacatg    300
gagctcagca gcctgagatc tgaggacact gccgtctatt actgtgcaag atcgtgggtt    360
agctacgaga gggggtatta ttttgactac tggggtcaag gaaccctggt caccgtctcc    420
tcagcctcca ccaagggccc atcggtcttc cccctggcac cctcctccaa gagcacctct    480
gggggcacag cggccctggg ctgcctggtc aaggactact tccccgaacc ggtgacggtg    540
tcgtggaact caggcgccct gaccagcggc gtgcacacct tcccggctgt cctacagtcc    600
tcaggactct actccctcag cagcgtggtg accgtgccct ccagcagctt gggcacccag    660
acctacatct gcaacgtgaa tcacaagccc agcaacacca aggtggacaa gaaagttgag    720
cccaaatctt gtgacaaaac tcacacatgc ccaccgtgcc cagcacctga actcctgggg    780
ggaccgtcag tcttcctctt cccccccaaaa cccaaggaca cctcatgat ctcccggacc    840 cctgaggtca catgcgtggt ggtggacgtg agccacgaag accctgaggt caagttcaac    900
tggtacgtgg acggcgtgga ggtgcataat gccaagacaa agccgcggga ggagcagtac    960
aacagcacgt accgtgtggt cagcgtcctc accgtcctgc accaggactg gctgaatggc   1020
aaggagtaca agtgcaaggt ctccaacaaa gccctcccag cccccatcga gaaaaccatc   1080
tccaaagcca aagggcagcc ccgagaacca caggtgtaca ccctgccccc atcccgggat   1140
gagctgacca agaaccaggt cagcctgacc tgcctggtca aaggcttcta tcccagcgac   1200
```

-continued

```
atcgccgtgg agtgggagag caatgggcag ccggagaaca actacaagac cacgcctccc    1260
gtgctggact ccgacggctc cttcttcctc tacagcaagc tcaccgtgga caagagcagg    1320
tggcagcagg ggaacgtctt ctcatgctcc gtgatgcatg aggctctgca caaccactac    1380
acgcagaaga gcctctccct gtctccgggt aaatga                              1416
```

<210> SEQ ID NO 37
<211> LENGTH: 471
<212> TYPE: PRT
<213> ORGANISM: Unknown
<220> FEATURE:
<223> OTHER INFORMATION: HuK33N gamma-1 heavy chain

<400> SEQUENCE: 37

```
Met Lys Cys Ser Trp Val Ile Phe Phe Leu Met Ala Val Val Thr Gly
1               5                   10                  15

Val Asn Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Ser Phe
        35                  40                  45

Thr Ser Tyr Tyr Met Asn Trp Val Arg Gln Ala Pro Gly Gln Arg Leu
    50                  55                  60

Glu Trp Ile Gly Trp Ile Phe Pro Gly Ser Gly Asn Thr Lys Tyr Asn
65                  70                  75                  80

Glu Lys Phe Lys Gly Lys Ala Thr Leu Thr Ala Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Ser Trp Val Ser Tyr Glu Arg Gly Tyr Tyr Phe
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
```

```
                    325                 330                 335
Trp Leu Asn Gly Lys Glu Tyr Lys Cys Lys Val Ser Asn Lys Ala Leu
                340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Asp Glu Leu Thr Lys
        370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 38
<211> LENGTH: 705
<212> TYPE: DNA
<213> ORGANISM: Unknown
<220> FEATURE:
<223> OTHER INFORMATION: HuK33N kappa light chain in pHuK33N

<400> SEQUENCE: 38
atgagtgtgc ccactcaact cctggggttg ctgctgctgt ggcttacaga cgcacgatgt      60
gacatccaga tgactcagtc tccatcctcc ctgtctgcat ctgtgggaga cagagtcacc     120
atcacatgtc gagcaagtga gaacatttac tacagtttag catggtatca gcagaagcca     180
gggaaagccc ctaagctcct gatctataat gcaaacagct tggaagatgg tgtcccatcg     240
aggttcagtg gcagtggatc tgggacacag tatactctca ccatcagcag cctgcagcct     300
gaagattttg caacttatta ctgtaaacag gcttatgacg ttccgtacac gttcggacaa     360
gggaccaagg tggaaatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
ctgagcaaag cagactacga gaaacacaaa gtctacgcct gcgaagtcac ccatcagggc     660
ctgagctcgc ccgtcacaaa gagcttcaac aggggagagt gttag                     705

<210> SEQ ID NO 39
<211> LENGTH: 234
<212> TYPE: PRT
<213> ORGANISM: Unknown
<220> FEATURE:
<223> OTHER INFORMATION: HuK33N kappa light chain

<400> SEQUENCE: 39

Met Ser Val Pro Thr Gln Leu Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Glu Asn
```

```
                35                  40                  45
Ile Tyr Tyr Ser Leu Ala Trp Tyr Gln Gln Lys Pro Gly Lys Ala Pro
 50                  55                  60

Lys Leu Leu Ile Tyr Asn Ala Asn Ser Leu Glu Asp Gly Val Pro Ser
 65                  70                  75                  80

Arg Phe Ser Gly Ser Gly Ser Gly Thr Gln Tyr Thr Leu Thr Ile Ser
                 85                  90                  95

Ser Leu Gln Pro Glu Asp Phe Ala Thr Tyr Tyr Cys Lys Gln Ala Tyr
                100                 105                 110

Asp Val Pro Tyr Thr Phe Gly Gln Gly Thr Lys Val Glu Ile Lys Arg
                115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
                195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230
```

<210> SEQ ID NO 40
<211> LENGTH: 39
<212> TYPE: DNA
<213> ORGANISM: Artificial Sequence
<220> FEATURE:
<223> OTHER INFORMATION: 5 primer for K33N VH with SpeI site

<400> SEQUENCE: 40
gggactagta ccaccatggg atggagctgg atctttctc                            39

<210> SEQ ID NO 41
<211> LENGTH: 49
<212> TYPE: DNA
<213> ORGANISM: Artificial Sequence
<220> FEATURE:
<223> OTHER INFORMATION: 3 primer for K33N VH with HindIII site

<400> SEQUENCE: 41
gggaagcttg ttttaaggac tcacctgagg agactctgag actggtgcc                 49

<210> SEQ ID NO 42
<211> LENGTH: 39
<212> TYPE: DNA
<213> ORGANISM: Artificial Sequence
<220> FEATURE:
<223> OTHER INFORMATION: 5 f primer for K33N VL with NheI site

<400> SEQUENCE: 42
ggggctagca ccaccatgag tgtgcccact caactcctg                            39

<210> SEQ ID NO 43
<211> LENGTH: 50
<212> TYPE: DNA
<213> ORGANISM: Artificial Sequence
<220> FEATURE:

<223> OTHER INFORMATION: 3 f primer for K33N VL with EcoRI site

<400> SEQUENCE: 43
ggggaattct gagaagacta cttacgtttt atttccagct tggtcccccc    50

<210> SEQ ID NO 44
<211> LENGTH: 24
<212> TYPE: DNA
<213> ORGANISM: Artificial Sequence
<220> FEATURE:
<223> OTHER INFORMATION: Primer CMV2

<400> SEQUENCE: 44
gaaccgtcag atcgcctgga gacg    24

<210> SEQ ID NO 45
<211> LENGTH: 20
<212> TYPE: DNA
<213> ORGANISM: Artificial Sequence
<220> FEATURE:
<223> OTHER INFORMATION: Primer JNT026

<400> SEQUENCE: 45
tgaaagatga gctggaggac    20

<210> SEQ ID NO 46
<211> LENGTH: 19
<212> TYPE: DNA
<213> ORGANISM: Artificial Sequence
<220> FEATURE:
<223> OTHER INFORMATION: Primer JNT080

<400> SEQUENCE: 46
gaactgtggc tgcaccatc    19

<210> SEQ ID NO 47
<211> LENGTH: 20
<212> TYPE: DNA
<213> ORGANISM: Artificial Sequence
<220> FEATURE:
<223> OTHER INFORMATION: Primer JNT082

<400> SEQUENCE: 47
ctttcttgtc caccttggtg    20

<210> SEQ ID NO 48
<211> LENGTH: 20
<212> TYPE: DNA
<213> ORGANISM: Artificial Sequence
<220> FEATURE:
<223> OTHER INFORMATION: Primer JNT084

<400> SEQUENCE: 48
gttgaagctc tttgtgacgg    20

<210> SEQ ID NO 49
<211> LENGTH: 19
<212> TYPE: DNA
<213> ORGANISM: Artificial Sequence
<220> FEATURE:
<223> OTHER INFORMATION: Primer JNT097

<400> SEQUENCE: 49
gctgtcctac agtcctcag    19

<210> SEQ ID NO 50

```
<211> LENGTH: 18
<212> TYPE: DNA
<213> ORGANISM: Artificial Sequence
<220> FEATURE:
<223> OTHER INFORMATION: Primer JNT098

<400> SEQUENCE: 50
acgtgccaag catcctcg                                                    18

<210> SEQ ID NO 51
<211> LENGTH: 23
<212> TYPE: DNA
<213> ORGANISM: Artificial Sequence
<220> FEATURE:
<223> OTHER INFORMATION: GeneRacer 5 primer

<400> SEQUENCE: 51
cgactggagc acgaggacac tga                                              23

<210> SEQ ID NO 52
<211> LENGTH: 20
<212> TYPE: DNA
<213> ORGANISM: Artificial Sequence
<220> FEATURE:
<223> OTHER INFORMATION: 3 primer for PCR amplification of heavy chain
      variable region VH

<400> SEQUENCE: 52
gccagtggat agacagatgg                                                  20

<210> SEQ ID NO 53
<211> LENGTH: 21
<212> TYPE: DNA
<213> ORGANISM: Artificial Sequence
<220> FEATURE:
<223> OTHER INFORMATION: 3 primer for PCR amplification of light chain
      variable region VL

<400> SEQUENCE: 53
gatggataca gttggtgcag c                                                21

<210> SEQ ID NO 54
<211> LENGTH: 8
<212> TYPE: PRT
<213> ORGANISM: Unknown
<220> FEATURE:
<223> OTHER INFORMATION: Tenascin-C 33-35

<400> SEQUENCE: 54

Ala Glu Ile Asp Gly Ile Glu Leu
1               5

<210> SEQ ID NO 55
<211> LENGTH: 1035
<212> TYPE: PRT
<213> ORGANISM: Homo sapiens

<400> SEQUENCE: 55

Met Gly Gly Pro Ala Ala Pro Arg Gly Ala Gly Arg Leu Arg Ala Leu
1               5                   10                  15

Leu Leu Ala Leu Val Val Ala Gly Ile Pro Ala Gly Ala Tyr Asn Leu
                20                  25                  30

Asp Pro Gln Arg Pro Val His Phe Gln Gly Pro Ala Asp Ser Phe Phe
            35                  40                  45

Gly Tyr Ala Val Leu Glu His Phe His Asp Asn Thr Arg Trp Val Leu
        50                  55                  60
```

```
Val Gly Ala Pro Lys Ala Asp Ser Lys Tyr Ser Pro Ser Val Lys Ser
 65                  70                  75                  80

Pro Gly Ala Val Phe Lys Cys Arg Val His Thr Asn Pro Asp Arg Arg
                 85                  90                  95

Cys Thr Glu Leu Asp Met Ala Arg Gly Lys Asn Arg Gly Thr Ser Cys
            100                 105                 110

Gly Lys Thr Cys Arg Glu Asp Arg Asp Asp Glu Trp Met Gly Val Ser
        115                 120                 125

Leu Ala Arg Gln Pro Lys Ala Asp Gly Arg Val Leu Ala Cys Ala His
    130                 135                 140

Arg Trp Lys Asn Ile Tyr Tyr Glu Ala Asp His Ile Leu Pro His Gly
145                 150                 155                 160

Phe Cys Tyr Ile Ile Pro Ser Asn Leu Gln Ala Lys Gly Arg Thr Leu
                165                 170                 175

Ile Pro Cys Tyr Glu Glu Tyr Lys Lys Lys Tyr Gly Glu Glu His Gly
            180                 185                 190

Ser Cys Gln Ala Gly Ile Ala Gly Phe Phe Thr Glu Glu Leu Val Val
        195                 200                 205

Met Gly Ala Pro Gly Ser Phe Tyr Trp Ala Gly Thr Ile Lys Val Leu
    210                 215                 220

Asn Leu Thr Asp Asn Thr Tyr Leu Lys Leu Asn Asp Glu Val Ile Met
225                 230                 235                 240

Asn Arg Arg Tyr Thr Tyr Leu Gly Tyr Ala Val Thr Ala Gly His Phe
                245                 250                 255

Ser His Pro Ser Thr Ile Asp Val Val Gly Gly Ala Pro Gln Asp Lys
            260                 265                 270

Gly Ile Gly Lys Val Tyr Ile Phe Arg Ala Asp Arg Arg Ser Gly Thr
        275                 280                 285

Leu Ile Lys Ile Phe Gln Ala Ser Gly Lys Lys Met Gly Ser Tyr Phe
    290                 295                 300

Gly Ser Ser Leu Cys Ala Val Asp Leu Asn Gly Asp Gly Leu Ser Asp
305                 310                 315                 320

Leu Leu Val Gly Ala Pro Met Phe Ser Glu Ile Arg Asp Glu Gly Gln
                325                 330                 335

Val Thr Val Tyr Ile Asn Arg Gly Asn Gly Ala Leu Glu Glu Gln Leu
            340                 345                 350

Ala Leu Thr Gly Asp Gly Ala Tyr Asn Ala His Phe Gly Glu Ser Ile
        355                 360                 365

Ala Ser Leu Asp Asp Leu Asp Asn Asp Gly Phe Pro Asp Val Ala Ile
    370                 375                 380

Gly Ala Pro Lys Glu Asp Asp Phe Ala Gly Ala Val Tyr Ile Tyr His
385                 390                 395                 400

Gly Asp Ala Gly Gly Ile Val Pro Gln Tyr Ser Met Lys Leu Ser Gly
                405                 410                 415

Gln Lys Ile Asn Pro Val Leu Arg Met Phe Gly Gln Ser Ile Ser Gly
            420                 425                 430

Gly Ile Asp Met Asp Gly Asn Gly Tyr Pro Asp Val Thr Val Gly Ala
        435                 440                 445

Phe Met Ser Asp Ser Val Val Leu Leu Arg Ala Arg Pro Val Ile Thr
    450                 455                 460

Val Asp Val Ser Ile Phe Leu Pro Gly Ser Ile Asn Ile Thr Ala Pro
465                 470                 475                 480

Gln Cys His Asp Gly Gln Gln Pro Val Asn Cys Leu Asn Val Thr Thr
```

```
                    485                 490                 495
Cys Phe Ser Phe His Gly Lys His Val Pro Gly Glu Ile Gly Leu Asn
                500                 505                 510

Tyr Val Leu Met Ala Asp Val Ala Lys Lys Glu Lys Gly Gln Met Pro
            515                 520                 525

Arg Val Tyr Phe Val Leu Leu Gly Glu Thr Met Gly Gln Val Thr Glu
        530                 535                 540

Lys Leu Gln Leu Thr Tyr Met Glu Glu Thr Cys Arg His Tyr Val Ala
545                 550                 555                 560

His Val Lys Arg Arg Val Gln Asp Val Ile Ser Pro Ile Val Phe Glu
                565                 570                 575

Ala Ala Tyr Ser Leu Ser Glu His Val Thr Gly Glu Glu Arg Glu
                580                 585                 590

Leu Pro Pro Leu Thr Pro Val Leu Arg Trp Lys Lys Gly Gln Lys Ile
            595                 600                 605

Ala Gln Lys Asn Gln Thr Val Phe Glu Arg Asn Cys Arg Ser Glu Asp
        610                 615                 620

Cys Ala Ala Asp Leu Gln Leu Gln Gly Lys Leu Leu Leu Ser Ser Met
625                 630                 635                 640

Asp Glu Lys Thr Leu Tyr Leu Ala Leu Gly Ala Val Lys Asn Ile Ser
                645                 650                 655

Leu Asn Ile Ser Ile Ser Asn Leu Gly Asp Asp Ala Tyr Asp Ala Asn
            660                 665                 670

Val Ser Phe Asn Val Ser Arg Glu Leu Phe Phe Ile Asn Met Trp Gln
        675                 680                 685

Lys Glu Glu Met Gly Ile Ser Cys Glu Leu Leu Glu Ser Asp Phe Leu
690                 695                 700

Lys Cys Ser Val Gly Phe Pro Phe Met Arg Ser Lys Ser Lys Tyr Glu
705                 710                 715                 720

Phe Ser Val Ile Phe Asp Thr Ser His Leu Ser Gly Glu Glu Val
                725                 730                 735

Leu Ser Phe Ile Val Thr Ala Gln Ser Gly Asn Thr Glu Arg Ser Glu
            740                 745                 750

Ser Leu His Asp Asn Thr Leu Val Leu Met Val Pro Leu Met His Glu
        755                 760                 765

Val Asp Thr Ser Ile Thr Gly Ile Met Ser Pro Thr Ser Phe Val Tyr
770                 775                 780

Gly Glu Ser Val Asp Ala Ala Asn Phe Ile Gln Leu Asp Asp Leu Glu
785                 790                 795                 800

Cys His Phe Gln Pro Ile Asn Ile Thr Leu Gln Val Tyr Asn Thr Gly
                805                 810                 815

Pro Ser Thr Leu Pro Gly Ser Ser Val Ser Ile Ser Phe Pro Asn Arg
            820                 825                 830

Leu Ser Ser Gly Gly Ala Glu Met Phe His Val Gln Glu Met Val Val
        835                 840                 845

Gly Gln Glu Lys Gly Asn Cys Ser Phe Gln Lys Asn Pro Thr Pro Cys
850                 855                 860

Ile Ile Pro Gln Glu Gln Glu Asn Ile Phe His Thr Ile Phe Ala Phe
865                 870                 875                 880

Phe Thr Lys Ser Gly Arg Lys Val Leu Asp Cys Glu Lys Pro Gly Ile
                885                 890                 895

Ser Cys Leu Thr Ala His Cys Asn Phe Ser Ala Leu Ala Lys Glu Glu
            900                 905                 910
```

```
Ser Arg Thr Ile Asp Ile Tyr Met Leu Leu Asn Thr Glu Ile Leu Lys
    915                 920                 925

Lys Asp Ser Ser Val Ile Gln Phe Met Ser Arg Ala Lys Val Lys
    930                 935                 940

Val Asp Pro Ala Leu Arg Val Val Glu Ile Ala His Gly Asn Pro Glu
945                 950                 955                 960

Glu Val Thr Val Val Phe Glu Ala Leu His Asn Leu Glu Pro Arg Gly
                965                 970                 975

Tyr Val Val Gly Trp Ile Ile Ala Ile Ser Leu Leu Val Gly Ile Leu
            980                 985                 990

Ile Phe Leu Leu Leu Ala Val Leu  Leu Trp Lys Met Gly  Phe Phe Arg
        995                 1000                1005

Arg Arg  Tyr Lys Glu Ile Ile  Glu Ala Glu Lys Asn  Arg Lys Glu
    1010                1015                1020

Asn Glu  Asp Ser Trp Asp Trp  Val Gln Lys Asn Gln
    1025                1030                1035

<210> SEQ ID NO 56
<211> LENGTH: 20
<212> TYPE: DNA
<213> ORGANISM: Artificial Sequence
<220> FEATURE:
<223> OTHER INFORMATION: 5 f RACE primer

<400> SEQUENCE: 56
gccagtggat agactgatgg                                                   20

<210> SEQ ID NO 57
<211> LENGTH: 21
<212> TYPE: DNA
<213> ORGANISM: Artificial Sequence
<220> FEATURE:
<223> OTHER INFORMATION: 5 f RACE primer

<400> SEQUENCE: 57
gatggataca gttggtgcag c                                                 21

<210> SEQ ID NO 58
<211> LENGTH: 19
<212> TYPE: PRT
<213> ORGANISM: Unknown
<220> FEATURE:
<223> OTHER INFORMATION: Signal peptide of HuK33N H-chain

<400> SEQUENCE: 58

Met Lys Cys Ser Trp Val Ile Phe Phe Leu Met Ala Val Val Thr Gly
1               5                   10                  15

Val Asn Ser

<210> SEQ ID NO 59
<211> LENGTH: 20
<212> TYPE: PRT
<213> ORGANISM: Unknown
<220> FEATURE:
<223> OTHER INFORMATION: Signal peptide of HuK33N L-chain

<400> SEQUENCE: 59

Met Ser Val Pro Thr Gln Leu Leu Gly Leu Leu Leu Leu Trp Leu Thr
1               5                   10                  15

Asp Ala Arg Cys
            20
```

```
<210> SEQ ID NO 60
<211> LENGTH: 122
<212> TYPE: PRT
<213> ORGANISM: Unknown
<220> FEATURE:
<223> OTHER INFORMATION: Mature VH of HuK33N

<400> SEQUENCE: 60
```

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Thr Ser Tyr
            20                  25                  30

Tyr Met Asn Trp Val Arg Gln Ala Pro Gly Gln Arg Leu Glu Trp Ile
        35                  40                  45

Gly Trp Ile Phe Pro Gly Ser Gly Asn Thr Lys Tyr Asn Glu Lys Phe
    50                  55                  60

Lys Gly Lys Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Val Ser Tyr Glu Arg Gly Tyr Phe Asp Tyr Trp
            100                 105                 110

Gly Gln Gly Thr Leu Val Thr Val Ser Ser
        115                 120

```
<210> SEQ ID NO 61
<211> LENGTH: 107
<212> TYPE: PRT
<213> ORGANISM: Unknown
<220> FEATURE:
<223> OTHER INFORMATION: Mature VL of HuK33N

<400> SEQUENCE: 61
```

Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Asn Ile Tyr Tyr Ser
            20                  25                  30

Leu Ala Trp Tyr Gln Gln Lys Pro Gly Lys Ala Pro Lys Leu Leu Ile
        35                  40                  45

Tyr Asn Ala Asn Ser Leu Glu Asp Gly Val Pro Ser Arg Phe Ser Gly
    50                  55                  60

Ser Gly Ser Gly Thr Gln Tyr Thr Leu Thr Ile Ser Ser Leu Gln Pro
65                  70                  75                  80

Glu Asp Phe Ala Thr Tyr Tyr Cys Lys Gln Ala Tyr Asp Val Pro Tyr
                85                  90                  95

Thr Phe Gly Gln Gly Thr Lys Val Glu Ile Lys
            100                 105

```
<210> SEQ ID NO 62
<211> LENGTH: 366
<212> TYPE: DNA
<213> ORGANISM: Unknown
<220> FEATURE:
<223> OTHER INFORMATION: HuK33N VH gene

<400> SEQUENCE: 62
caggtccaac tggtgcagtc tggagctgag gttaagaagc ctggggcttc agtgaaggtt     60
tcctgcaagg cttctggcta cagctttaca agttactata tgaattgggt gcgccaggcc    120
cctggacaga ggcttgagtg gattggttgg atctttcctg gaagtggtaa tactaagtac    180
```

```
aatgagaagt tcaagggcaa ggccacactg acggcagaca catccgccag tacagcctac    240
atggagctca gcagcctgag atctgaggac actgccgtct attactgtgc aagatcgtgg    300
gttagctacg agaggggta ttattttgac tactggggtc aaggaaccct ggtcaccgtc    360
tcctca                                                                366

<210> SEQ ID NO 63
<211> LENGTH: 321
<212> TYPE: DNA
<213> ORGANISM: Unknown
<220> FEATURE:
<223> OTHER INFORMATION: HuK33N VL gene

<400> SEQUENCE: 63
gacatccaga tgactcagtc tccatcctcc ctgtctgcat ctgtgggaga cagagtcacc     60
atcacatgtc gagcaagtga gaacatttac tacagtttag catggtatca gcagaagcca    120
gggaaagccc ctaagctcct gatctataat gcaaacagct tggaagatgg tgtcccatcg    180
aggttcagtg gcagtggatc tgggacacag tatactctca ccatcagcag cctgcagcct    240
gaagattttg caacttatta ctgtaaacag gcttatgacg ttccgtacac gttcggacaa    300
gggaccaagg tggaaatcaa a                                              321

<210> SEQ ID NO 64
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(7)
<223> OTHER INFORMATION: OPN alpha-9 integrin binding-site peptide

<400> SEQUENCE: 64

Ser Val Val Tyr Gly Leu Arg
1               5
```